(12) United States Patent
Mutalik et al.

(10) Patent No.: US 12,054,852 B2
(45) Date of Patent: Aug. 6, 2024

(54) MULTIPLEX CHARACTERIZATION OF MICROBIAL TRAITS USING DUAL BARCODED NUCLEIC ACID FRAGMENT EXPRESSION LIBRARY

(71) Applicant: The Regents of the University of California, Oakland, CA (US)

(72) Inventors: Vivek K. Mutalik, Albany, CA (US); Adam Deutschbauer, Berkeley, CA (US); Adam P. Arkin, San Francisco, CA (US); Pavel Novichkov, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 1075 days.

(21) Appl. No.: 15/665,226

(22) Filed: Jul. 31, 2017

(65) Prior Publication Data
US 2018/0030435 A1    Feb. 1, 2018

Related U.S. Application Data

(60) Provisional application No. 62/369,699, filed on Aug. 1, 2016.

(51) Int. Cl.
C40B 30/06     (2006.01)
C12N 15/10     (2006.01)

(52) U.S. Cl.
CPC .......... *C40B 30/06* (2013.01); *C12N 15/1065* (2013.01)

(58) Field of Classification Search
CPC .................. C12N 15/1065; C12N 15/1086
See application file for complete search history.

(56) References Cited

U.S. PATENT DOCUMENTS

| 7,405,282 B2* | 7/2008 | Duvick ........................ 536/22.1 |
| 2007/0059768 A1* | 3/2007 | Gill et al. .............. C12N 15/66 |
| 2012/0178635 A1* | 7/2012 | Dutta et al. ..................... 506/4 |
| 2017/0267997 A1* | 9/2017 | Nicol et al. ........ C12N 15/1065 |

OTHER PUBLICATIONS

Lynch et al. "SCALEs: multiscale analysis of library enrichment" Nature Methods 4(1):87-93, 2006 DOI: 10.1038/NMETH946 (Year: 2006).*
Smith et al. "Quantitative phenotyping via deep barcode sequencing" Genome Research 19:1836-1842, 2009 at http://www.genome.org/cgi/doi/10.1101/gr.093955.109 (Year: 2009).*
Bikard et al., Programmable repression and activation of bacterial gene expression using an engineered CRISPR-Cas system, Nucleic Acids Research, Aug. 2013, 41(15): 7429-7437.

(Continued)

*Primary Examiner* — Christian C Boesen
(74) *Attorney, Agent, or Firm* — Sheppard, Mullin, Richter & Hampton LLP

(57) ABSTRACT

Disclosed herein are barcoded expression libraries comprising a plurality of expression vectors, wherein each expression vector comprises a nucleic acid fragment flanked by a first barcode and a second barcode. Further disclosed herein are methods of making the barcoded expression libraries and methods of conducting functional analysis using the barcoded expression libraries.

14 Claims, 32 Drawing Sheets

Specification includes a Sequence Listing.

(56) References Cited

OTHER PUBLICATIONS

Dharmacon, http://dharmacon.gelifesciences.com/cdnas-and-orfs/cdna-and-orf-libraries/, accessed Oct. 26, 2017, 3 pp.
Deutschbauer et al., Evidence-based annotation of gene function in Shewanella oneidensis MR-1 using genome-wide fitness profiling across 121 conditions, PLoS Genetics, Nov. 2011, 7(11):e1002385.
Deutschbauer et al., Towards an informative mutant phenotype for every bacterial gene, Journal of Bacteriology, Oct. 2014, 196(20):3643-3655.
Kazakov et al., New family of tungstate-responsive transcriptional regulators in sulfate-reducing bacteria, Journal of Bacteriology, Oct. 2013, 195(19):4466-4475.
Kazakov et al., σ54-dependent regulome in Desulfovibrio vulgaris Hildenborough. BMC Genomics, Nov. 2015, 16(919), DOI 10.1186/s12864-015-2176-y.
Kitagawa et al., Complete set of ORF clones of *Escherichia coli* ASKA library (a complete set of *E. coli* K-12 ORFarchive): unique resources for biological research, DNA Research, Jan. 2005, 12(5):291-299.
Kuehl et al., Functional genomics with a comprehensive library of transposon mutants for the sulfate-reducing bacterium Desulfovibrio alaskensis G20, mBio, May 2014, 5(3): e01041-14, doi:10.1128/mBio.01041-14.
Lale et al., Broad-host-range plasmid vectors for gene expression in bacteria, Strain Engineering: Methods and Protocols, Methods in Molecular Biology, (Ed., James Williams), Humana Press, Jun. 2011, vol. 756, Chapter 19, pp. 327-343.
Leis et al., Screening and expression of genes from metagenomes, Advances in Applied Microbiology, May 2013, vol. 83, Chapter 1, pp. 1-68.
Mutalik et al., Promoter strength properties of the complete sigma-E regulon of *Escherichia coli* and *Salmonella enterica*, Journal of Bacteriology, Dec. 2009, 191(23):7279-7287.
Mutalik et al., Rationally designed families of orthogonal RNA regulators of translation, Nature Chemical Biology, May 2012, 8(5):447-454.
Mutalik et al., Precise and reliable gene expression via standard transcription and translation initiation elements, Nature Methods, Apr. 2013, 10(4):354-360.
Mutalik et al., Quantitative estimation of activity and quality for collections of functional genetic elements, Nature Methods, Apr. 2013, 10(4):347-353.
Neufeld et al., Open resource metagenomics: a model for sharing metagenomic libraries, Standards in Genomic Sciences, Nov. 2011, 5(2):203-210.
Novichkov et al., RegPredict: an integrated system for regulon inference in prokaryotes by comparative genomics approach, Nucleic Acids Research, Jun. 2010, 38 (Web Server issue): W299-307, doi: 10.1093/nar/gkq531.
Novichkov et al., RegPrecise 3.0—a resource for genome-scale exploration of transcriptional regulation in bacteria, BMC Genomics, Nov. 2013, 14:745.
Novichkov et al., Control of methionine metabolism by the SahR transcriptional regulator in Proteobacteria, Environmental Microbiology, Jan. 2014, 16(1):1-8.
Opijnen et al., Tn-seq: high-throughput parallel sequencing for fitness and genetic interaction studies in microorganisms, Nat Methods, Oct. 2009, 6(10):767-772.
Price et al., Evidence-based annotation of transcripts and proteins in the sulfate-reducing bacterium desulfovibrio vulgaris hildenborough, Journal of Bacteriology, Oct. 2011, 193(20):5716-5727.
Price et al., Indirect and suboptimal control of gene expression is widespread in bacteria, Molecular Systems Biology, Apr. 2013, 9(660) doi:10.1038/msb.2013.16.
Price et al., The genetic basis of energy conservation in the sulfate-reducing bacterium Desulfovibrio alaskensis G20, Frontiers in Microbiology, Oct. 2014, 5(577), doi: 10.3389/fmicb.2014.00577.
Rhodius et al., Predicting strength and function for promoters of the *Escherichia coli* alternative sigma factor, σE, Proceedings of the National Academy of Sciences, Feb. 2010, 107(7):2854-2859.
Rhodius et al., Predicting the strength of UP-elements and full-length *E coli* σE promoters, Nucleic Acids Research, 40(7):2907-2924 Dec. 2011.
Shao et al., Conservation of transcription start sites within genes across a bacterial genus, mBio, Jul. 2014,5(4):e01398-14, doi: 10.1128/mBio.01398-14.
Simon et al., Construction of small-insert and large-insert metagenomics libraries, Metagenomics: Methods and Protocols, Methods in Molecular Biology, Wolfgang Streit and Rolf Daniel (Eds.), Humana Press, Sep. 2010, vol. 668, Chapter 2, pp. 39-50.
Sun et al., Comparative genomics of metaolic capacities of regulons controlled by cis-regulatory RNA motifs in bacteria, BMC Genomics, Sep. 2013; 14:597.
Wetmore et al., Rapid quantification of mutant fitness in diverse bacteria by sequencing randomly bar-coded transposons, mBio, May 2015, 6(3):e00306-15.
Dharmacon, http://dharmacon.gelifesciences.com/cdnas-and-orfs/non-mammalian-cdnas-and-orfs/yeast/yeast-orf-collection/, accessed Oct. 26, 2017, 4 pp.
Berkeley Lab, "Dub-seq Wins 2017 R&D100 Award," BioSciences 2017, in 1 page. https://biosciences.lbl.gov/2017/11/20/dub-seq-wins-2017-rd100-award/.
Encyclopedia Britannica, "Stress" 2022, in 1 page. https://www.britannica.com/science/stress-psychology-and-biology.
Mutalik et al., "Dual-barcoded shotgun expression library sequencing for high-throughput characterization of functional traits in bacteria," Nature Communication 2019, 10(308), 1-14.
Wikipedia, "Stress (biology)," 2022, in 1 page. https://en.wikipedia.org/wiki/Stress_(biology).

* cited by examiner

Primer Forward:   Tnseq for uptag_module; Nspacer_barseq_universal; Flow cell P5

Seq ID No. 22  5'  *ATGATACGGCGACCACCGA*AGATCTACACTCTTTCCCTACACGACGCTCTTCCGATCTNNNNNNgATGTCCACGAGGTCT  3'
                   Italics region binds to Flow Cell P5, entire underlined is a TruSeq Universal Adapter    Binds to UP barcode Primer1

Primer Reverse binds to adaptor; P7_MOD_TS_index1 to index16,

Seq ID No. 23  5'  *CAAGCAGAAGACGGCATACGAGAT*CGGTGATGTGACTGGAGTTCAGACGTGTGCTCTTCCGATCT  3'

(b)

UP barcode Primer1                              UP barcode                         UP barcode Primer2

Seq ID  5'  Gatgtccacgaggtctctnnnnnnnnnnnnnnncgtacgctgcaggtcgaccac(*GenomeFragment*)  3'
No. 24

Primer Forward:   Tnseq for Down tag_module; Nspacer_barseq_universal; Flow cell P5

Seq ID No: 43   5' *ATGATAAGGCGACCACCGAGATCTACACTCTTTCCCTACACGACGCTCTTCCGATCT*NNNNNN:cgtcgtcgtcgta 3'
                   Italics region binds to Flow Cell P5, entire underlined is a TruSeq Universal Adapter   Binds to Down barcode Primer1

Primer Reverse binds to adaptor: P7_MOD_TS_index1 to index16,

Seq ID No: 23   CAAGCAGAAGACGGCATACGAGATCGGTGATGTGACTGGAGTTCAGACGTGTGCTCTTCCGATCT (b)
                        DOWN barcode Primer2              DOWN barcode              DOWN barcode Primer1
Seq ID   3' *GenomeFragment*. gtg taagtaagtaaGaaaacgagctcgaa) catcgnnnnnnnnnnnnnnnctagagacgaacg 5'
No: 44

(c)

VM Tnseq for Down tag module'
        Flowcell P5 primer
                    ↗              ↘
                                    Flow cell P7 primer
                                    P7_MOD_TS_index1 to index16

BAGseq 2: Reads down tag first
(and then genomic fragment)

*FIG. 9*

*(a)* Good library prep
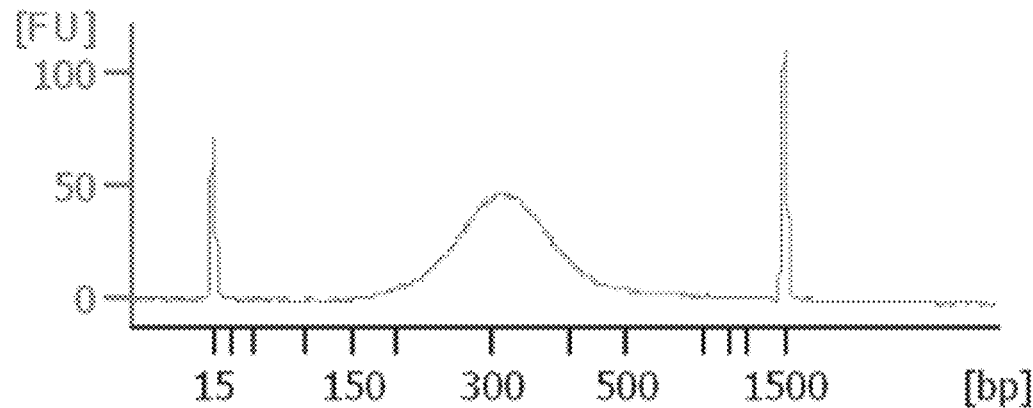
*(b)* Bad prep - too much adapter dimer on the left
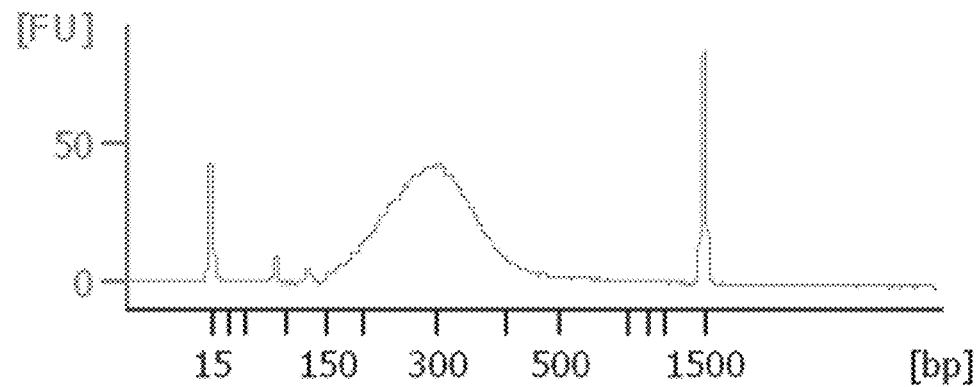
*FIG. 10*

(a)

(b) FEBA_Barseq_P1_BSP_RV = Reverse primer anneals to UP tag common priming site; Flow Cell P5

Seq ID No. 45  AATGATACGGCGACCACCGAGATCTACACTCTTTCCCTACACGACGCTCTTCCGATCTNNNNNGTCGACCTGCAGCGTACG
Italics region binds to Flow Cell P5, entire underlined is a TruSeq Universal Adapter    Binds to UP barcode Primer2 region Barseq_P2_IT001 (Barseq Forward primer with index 1 to 96) = anneals to UP tag comon primming site; Flow cell P7

Seq ID No. 4  CAAGCAGAAGACGGCATACGAGAT CGTGAT GTGACTGGAGTTCAGACGTGTGCTCTTCCGATCT GATGTCACGAAGTCGT
Italics region binds to Flow Cell P7    Rev compl of Index 1: ATCACG    Binds to UP barcode Primer1 region (c) 5'— Barseq_P2_IT001 ———————————————3'
        UP barcode Primer 1

Seq ID No: 24  Gatgtccacgaggtctcnnnnnnnnnnnnnnnnnngtacgctgcaggtcgaccac-GenomeFragment-
                                           UP barcode                                     UP barcode Primer2
                                                                                                    5'
                                                                                                    region binds to
                                                                                                    Flow Cell P5
                                                                                            FEBA_Barseq_P1_BSP_RV Barseq: Up tag is read in reverse

FIG. 11

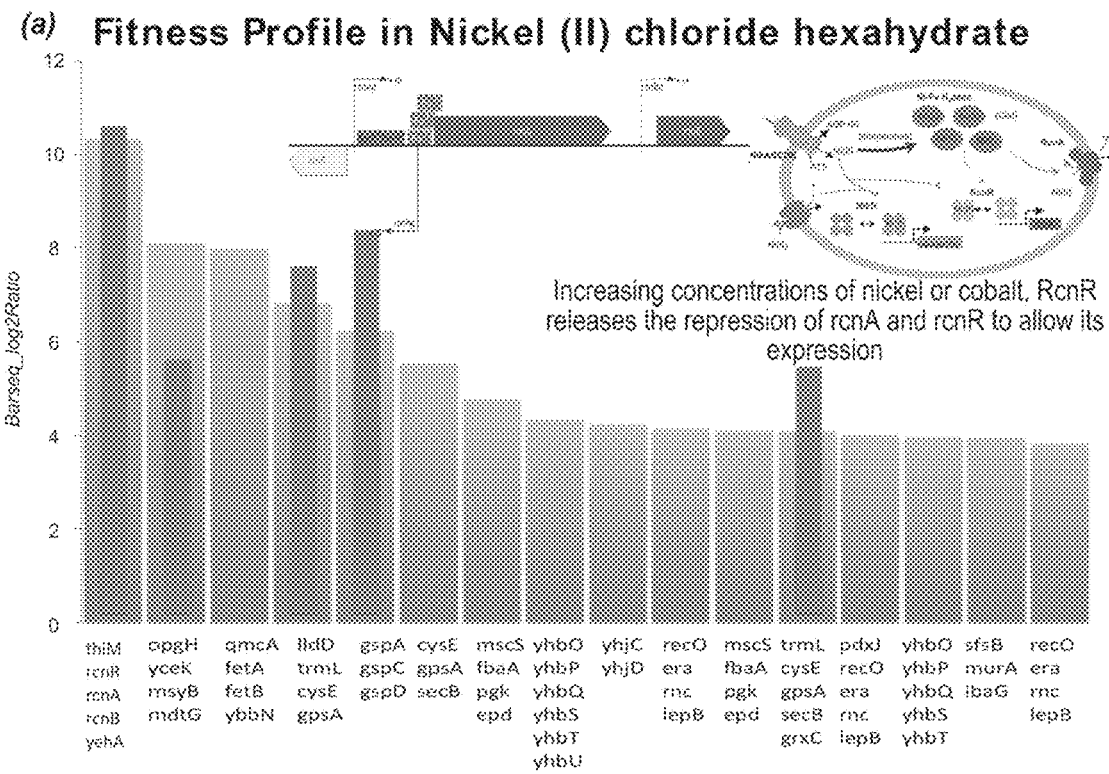
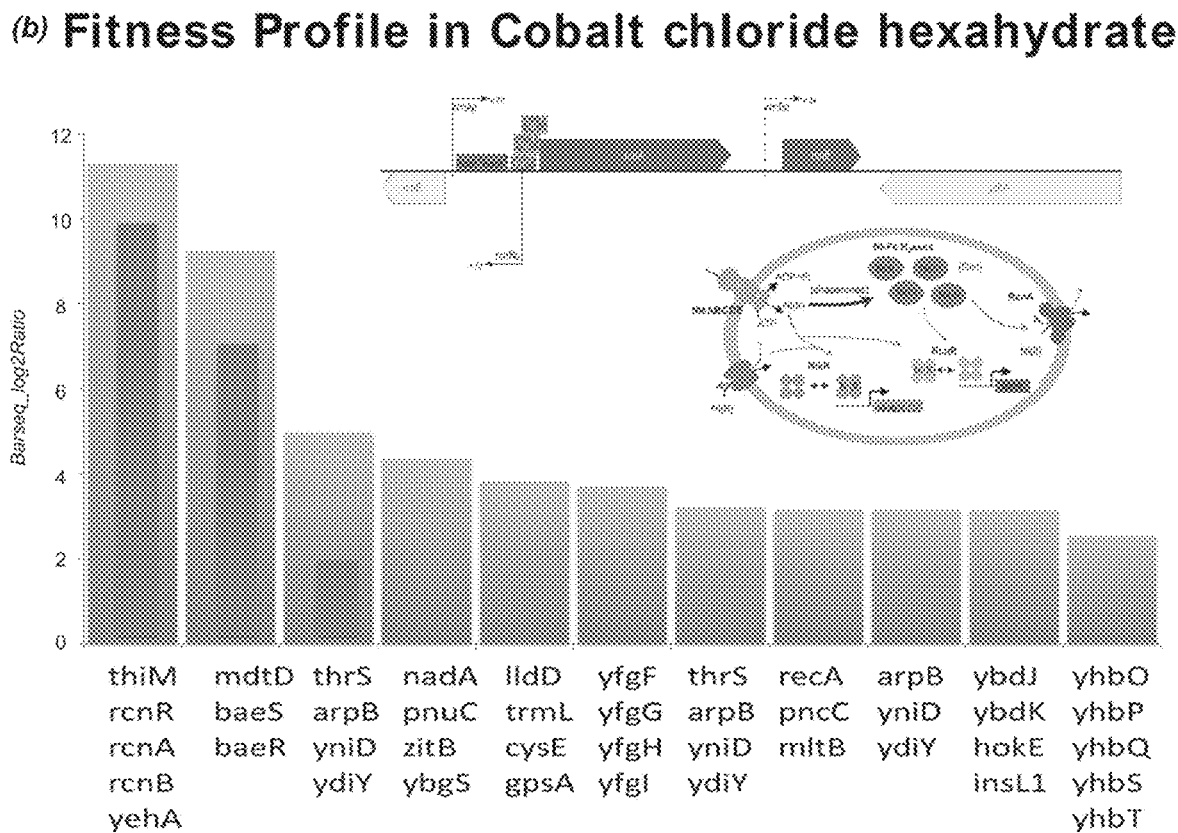
FIG. 14

(c) Fitness Profile in Copper (II) chloride dihydrate
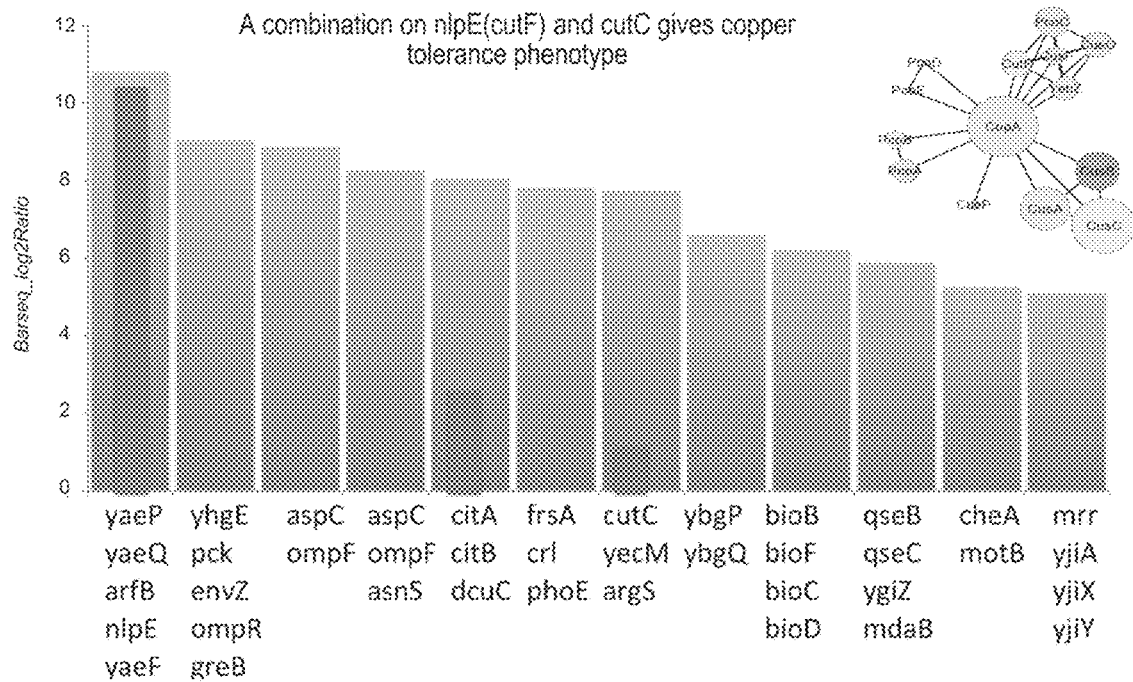
(d) Fitness Profile in Polymyxin B
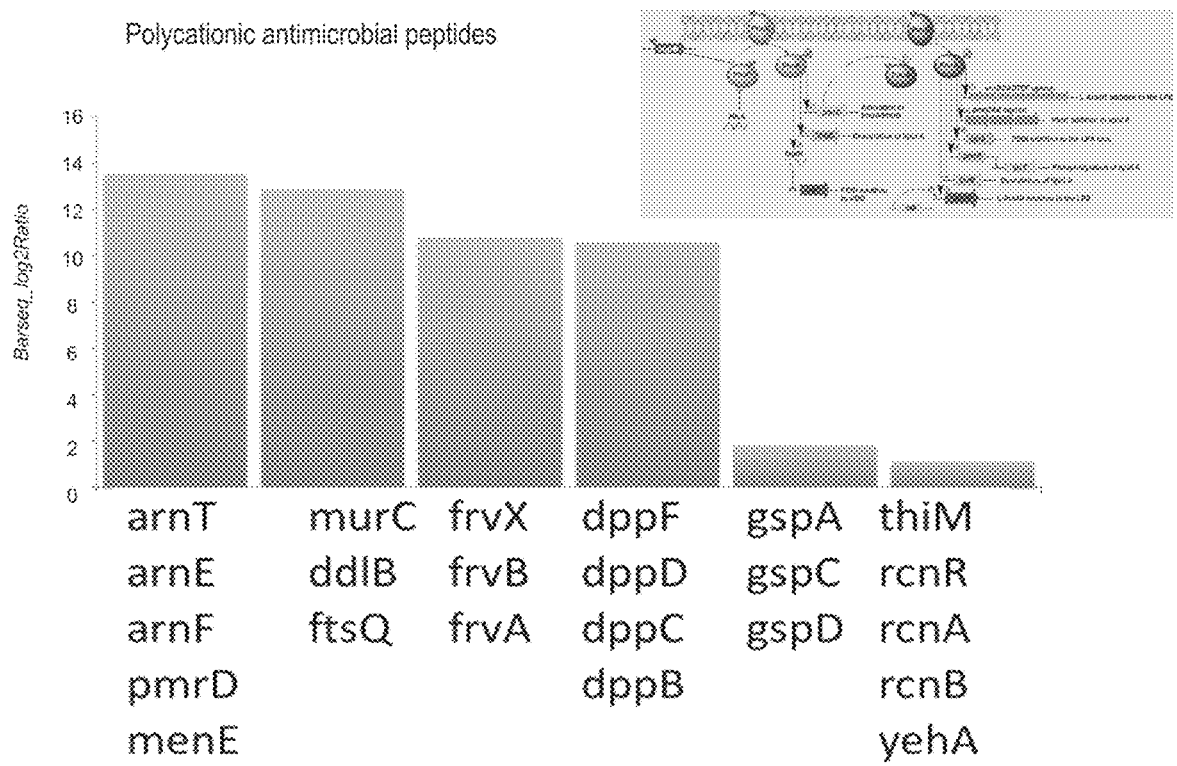
*FIG. 14 (Continued)*

(e) Fitness Profile in Benzalkonium Chloride
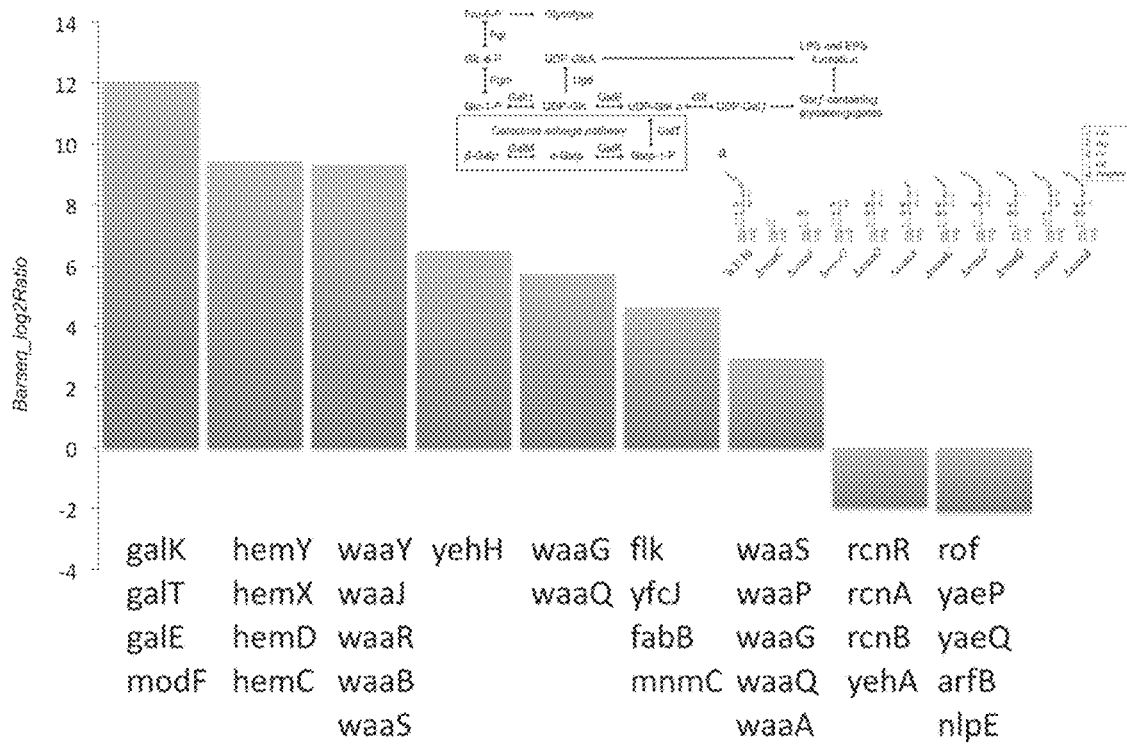
(f) Fitness Profile in Spectinomycin
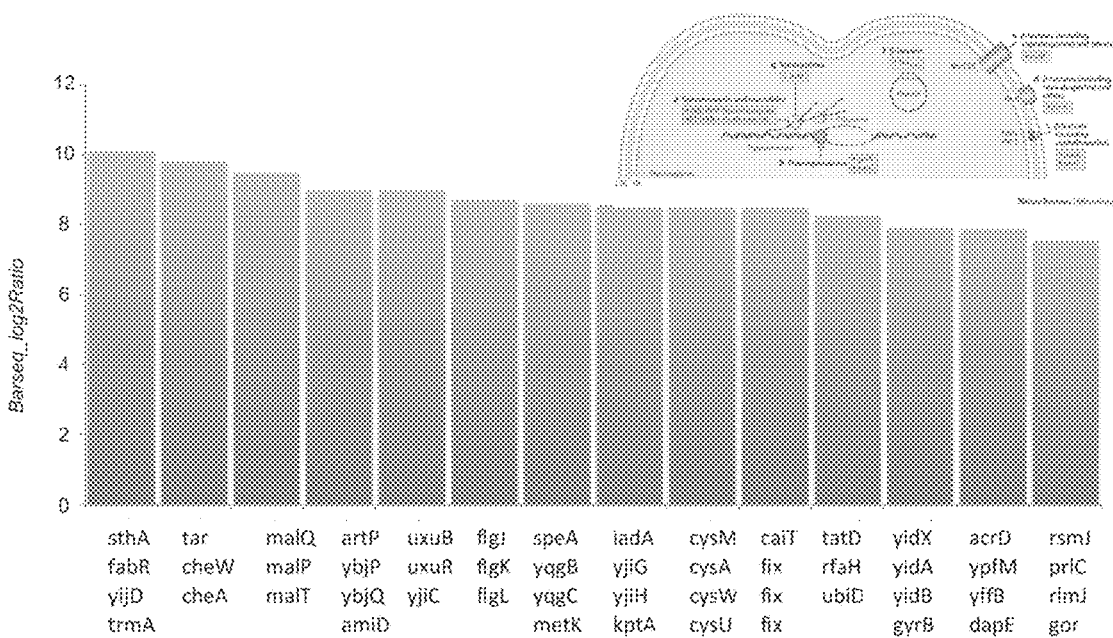
*FIG. 14 (Continued)* ical Traits Using Dual

SEQUENCE LISTING

```
<160> NUMBER OF SEQ ID NOS: 53

<210> SEQ ID NO 1
<211> LENGTH: 132
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (19)..(38)
<223> OTHER INFORMATION: n is a, c, g, or t
<220> FEATURE:
<221> NAME/KEY: misc_feature
<222> LOCATION: (96)..(115)
<223> OTHER INFORMATION: n is a, c, g, or t

<400> SEQUENCE: 1
gatgtccacg aggtctctnn nnnnnnnnnn nnnnnnnncg tacgctgcag gtcgaccacg      60
tgtaagtaag taagaaaacg agctcgaatt catcgnnnnn nnnnnnnnnn nnnnctacg     120 agaccgacac cg                                                        132

<210> SEQ ID NO 2
<211> LENGTH: 130
<212> TYPE: DNA
<213> ORGANISM: Artificial Sequence
```

```
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (19)..(38)
<223> OTHER INFORMATION: n is a, c, g, or t
<220> FEATURE:
<221> NAME/KEY: misc_feature
<222> LOCATION: (94)..(113)
<223> OTHER INFORMATION: n is a, c, g, or t

<400> SEQUENCE: 2
gatgtccacg aggtctctnn nnnnnnnnnn nnnnnnnncg tacgctgcag gtcgaccacg    60
tgtaagtaag taagaaaacg agctcgaaca tcgnnnnnnn nnnnnnnnnn nnnctacgag   120
accgacaccg                                                         130

<210> SEQ ID NO 3
<211> LENGTH: 80
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (59)..(63)
<223> OTHER INFORMATION: n is a, c, g, or t

<400> SEQUENCE: 3
aatgatacgg cgaccaccga gatctacact ctttccctac acgacgctct tccgatctnn   60
nnncggtgtc ggtctcgtag                                               80

<210> SEQ ID NO 4
<211> LENGTH: 82
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 4
caagcagaag acggcatacg agatcgtgat gtgactggag ttcagacgtg tgctcttccg   60
atctgatgtc cacgaggtct ct                                            82

<210> SEQ ID NO 5
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 5
naacacggtg tcggtctcgt agcatccaca acaagtgctt tacgatgaat tcgagctcgt   60
tttcttactt acttacacgt ggtcgacctg cagcgtacgt gcgtcgggtc ttgtctgcaa  120
gagacctcgt ggacatcaga tcggaagagc                                   150

<210> SEQ ID NO 6
<211> LENGTH: 150
<212> TYPE: DNA
```

```
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 6
ntgcgcggtg tcggtctcgt agccccaaac aagcgcctag ggcgatgaat tcgagctcgt    60
tttcttactt acttacacgt ggtcgacctg cagcgtacga tcttaaggtg aaaatggtga   120
gagacctcgt ggacatcaga tcggaagagc                                    150

<210> SEQ ID NO 7
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 7
ngtcccggtg tcggtctcgt agaacccggg tataaggggc gacgatgaat tcgagctcgt    60
tttcttactt acttacacgt ggtcgacctg cagcgtacgc gatcggtagc gcgatgttta   120
gagacctcgt ggacatcaga tcggaagagc                                    150

<210> SEQ ID NO 8
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 8
nacgccggtg tcggtctcgt agccgacgat tcaaaaaaca ctcgatgaat tcgagctcgt    60
tttcttactt acttacacgt ggtcgacctg cagcgtacgg aagcgtacgt gtgtggccga   120
gagacctcgt ggacatcaga tcggaagagc                                    150

<210> SEQ ID NO 9
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 9
ntgtccggtg tcggtctcgt aggccacttc atacgcgttt tacgatgaat tcgagctcgt    60
tttcttactt accgtggtcg acctgcagcg tacggaggtt agggttggaa ggggagagac   120
ctcgtggaca tcagatcgga agagcacacg                                    150
```

<210> SEQ ID NO 10
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 10
ntggccggtg tcggtctcgt agggggaccta aaagctatta cccgatgaat tcgagctcgt      60
tttcttactt acttacacgt ggtcgacctg cagcgtacgc ggcctataat gattattta      120 gagacctcgt ggacatcaga tcggaagagc                                       150

<210> SEQ ID NO 11
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 11
ntggccggtg tcggtctcgt agcatatgtg ctcgtataaa tgcgatgaat tcgagctcgt      60
tttcttactt acttacacgt ggtcgacctg cagcgtacgg ctgctcttgc gtcctttata     120
gagacctcgt ggacatcaga tcggaagagc                                       150

<210> SEQ ID NO 12
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 12
ngtgtcggtg tcggtctcgt aggacgagtt caaagcttct tgcgatgaat tcgagctcgt      60
tttcttactt acttacacgt ggtcgacctg cagcgtacgg ccaggtaggc aggacttcaa     120
gagacctcgt ggacatcaga tcggaagagc                                       150

<210> SEQ ID NO 13
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 13
nttggcggtg tcggtctcgt agccgcagac tagcccaatg gacgatgaat tcgagctcgt    60
tttcttactt acttacacgt ggtcgacctg cagcgtacgg gaatcgaggt gaggggttta   120
gagacctcgt ggacatcaga tcggaagagc                                    150

<210> SEQ ID NO 14
<211> LENGTH: 150
<212> TYPE: DNA
<213> ORGANISM: Artificial Sequence
<220> FEATURE:
<223> OTHER INFORMATION: note="Description of Artificial Sequence:
    Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 14
ngtggcggtg tcggtctcgt agtaatgatc aaaataatta ccgatgaatt cgagctcgtt    60
ttcttactta cttacacgtg gtcgacctgc agcgtacgta ggtgcgcgtg cgctccaaag   120
agacctcgtg gacatcagat cggaagagca                                   150

<210> SEQ ID NO 15
<211> LENGTH: 150
<212> TYPE: DNA
<213> ORGANISM: Artificial Sequence
<220> FEATURE:
<223> OTHER INFORMATION: note="Description of Artificial Sequence:
    Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 15
nggtacggtg tcggtctcgt agagacggaa gcacctcgtc agcgatgaat tcgagctcgt    60
tttcttactt acttacacgt ggtcgacctg cagcgtacgg cctatggtgt acacgattca   120
gagacctcgt ggacatcaga tcggaagagc                                   150

<210> SEQ ID NO 16
<211> LENGTH: 150
<212> TYPE: DNA
<213> ORGANISM: Artificial Sequence
<220> FEATURE:
<223> OTHER INFORMATION: note="Description of Artificial Sequence:
    Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 16 ngggggcggtg tcggtctcgt agtgtcatac gtgcaaccac aacgatgaat tcgagctcgt    60
tttcttactt acttacacgt ggtcgacctg cagcgtacga ccaaggggc gggtggtcga    120 gagacctcgt ggacatcaga tcggaagagc                                   150

<210> SEQ ID NO 17
<211> LENGTH: 150
<212> TYPE: DNA
<213> ORGANISM: Artificial Sequence
<220> FEATURE:
<223> OTHER INFORMATION: note="Description of Artificial Sequence:
    Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 17
ntaatcggtg tcggtctcgt agccccgcca acgtcaccgc cacgatgaat tcgagctcgt    60
tttcttactt acttacacgt ggtcgacctg cagcgtacgc tgcgacattt ggttatggga   120
gagacctcgt ggacatcaga tcggaagagc                                    150

<210> SEQ ID NO 18
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 18
nggttcggtg tcggtctcgt agctagtcca ggaatgctac cacgatgaat tcgagctcgt    60
tttcttactt acttacacgt ggtcgacctg cagcgtacga gcgaagatga tatgagagta   120
gagacctcgt ggacatcaga tcggaagagc                                    150

<210> SEQ ID NO 19
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 19
ngtgccggtg tcggtctcgt agccatcccg cttgcacatg cgcgatgaat tcgagctcgt    60
tttcttactt acttacacgt ggtcgacctg cagcgtacgc taacctgtga gcaggtggca   120
gagacctcgt ggacatcaga tcggaagagc                                    150

<210> SEQ ID NO 20
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: n is a, c, g, or t

<400> SEQUENCE: 20
nctggcggtg tcggtctcgt agagcgacac tgttacttac ttcgatgaat tcgagctcgt    60
tttcttacta cacgtggtcg acctgcagcg tacggggtat tagtatcttt tggtagagac   120
ctcgtggaca tcagatcgga agagcacacg                                    150

<210> SEQ ID NO 21
<211> LENGTH: 149
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 21
aaaacggtgt cggtctcgta gggcactaac cttacaccaa tcgatgaatt cgagctcgtt    60
ttcttactta cttacacgtg gtcgacctgc agcgtacggg actaggatgg cgttaggcag   120
agacctcgtg gacatcagat cggaagagc                                     149

<210> SEQ ID NO 22
<211> LENGTH: 79
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (58)..(63)
<223> OTHER INFORMATION: n is a, c, g, or t

<400> SEQUENCE: 22
atgatacggc gaccaccgag atctacactc tttccctaca cgacgctctt ccgatctnnn    60
nnngatgtcc acgaggtct                                                 79

<210> SEQ ID NO 23
<211> LENGTH: 64
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 23
caagcagaag acggcatacg agatcgtgat gtgactggag ttcagacgtg tgctcttccg    60
atct                                                                 64

<210> SEQ ID NO 24
<211> LENGTH: 59
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (19)..(38)
<223> OTHER INFORMATION: n is a, c, g, or t

<400> SEQUENCE: 24
gatgtccacg aggtctctnn nnnnnnnnn nnnnnnnncg tacgctgcag gtcgaccac      59

<210> SEQ ID NO 25
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 25 gaggggatg tccacgaggt ctctgacagc cttttgaacc tacccgtacg ctgcaggtcg     60
accacgggca tcgagaagga catccaagat cggaagagca cacgtctgaa ctccagtcac   120
ttaggcatct cgtatgccgt cttctgcttg                                    150

<210> SEQ ID NO 26
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 26
gtcgttgatg tccacgaggt ctctttcgac accgatttta aggccgtacg ctgcaggtcg      60
agatcggaag agcacacgtc tgaactccag tcacttaggc atctcgtatg ccgtcttctg     120
cttgaaaaaa aaaaaaaaac aattaacaaa                                      150

<210> SEQ ID NO 27
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 27
ggcctggatg tccacgaggt ctctacctag gtctgcgtaa accccgtacg ctgcaggtcg      60
accacagctc gcgccggacg gaggcgatcc gctccagcag atcggaagag cacacgtctg     120
aactccagtc acttaggcat ctcgtatgcc                                      150

<210> SEQ ID NO 28
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (136)..(136)
<223> OTHER INFORMATION: n is a, c, g, or t

<400> SEQUENCE: 28
tcaaatgatg tccacgaggt ctcttgtggc tacgtccacg gggtcgtacg ctgcaggtcg      60
accaccgccc ccaagaccta ctggtcgaag atcggaagag cacacgtctg aactccagtc     120
acttaggcat ctcgtntgcc gtcttctgct                                      150

<210> SEQ ID NO 29
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 29
agtattgatg tccacgaggt ctctacaact cacccctggg ccccgtacg ctgcaggtcg       60 accaccgcgg tgcagacgcc ggacgtcgcc ggcgtcagat cggaagagca cacgtctgaa     120
ctccagtcac ttaggcatct cgtatgccgt                                      150

<210> SEQ ID NO 30
<211> LENGTH: 150
<212> TYPE: DNA
<213> ORGANISM: Artificial Sequence
<220> FEATURE:

```
<223> OTHER INFORMATION: note="Description of Artificial Sequence:
      Synthetic Oligonucleotide"
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (134)..(136)
<223> OTHER INFORMATION: n is a, c, g, or t

<400> SEQUENCE: 30
ccttacgatg tccacgaggt ctctatagtt caccatgcat ttagcgtacg ctgcaggaga    60
tcggaagagc acacgtctga actccagtca cttaggcatc tcgtatgccg tcttctgntn   120
gnaaaaaaaa naannnaatc aatacaaaca                                    150

<210> SEQ ID NO 31
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 31
cgcactgatg tccacgaggt ctctatataa agcacgcaag acttcgtacg ctgcaggtcg    60
accacgtcaa gccctagatc ggaagagcac acgtctgaac tccagtcact taggcatctc   120
gtatgccgtc ttctgcttga aaaaaaaaaa                                    150

<210> SEQ ID NO 32
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 32
aatatcgatg tccacgaggt ctctgcagca gcaggctatc acgtcgtacg ctgcaggtca    60
gatcggaaga gcacacgtct gaactccagt cacttaggca tctcgtatgc cgtcttctgc   120
ttgtaacaaa aaaacctaac caaacttcaa                                    150

<210> SEQ ID NO 33
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 33
attgaggatg tccacgaggt ctcttgctac accttcgtct ctaccgtacg ctgcaggtcg    60
accaccgggc ttgccggcgg cctcggtgag gtcgagatcg gaagagcaca cgtctgaact   120
```

```
ccagtcactt aggcatctcg tatgccgtct                                              150
```

<210> SEQ ID NO 34
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 34

```
ggggcggatg tccacgaggt ctctctggcc atgtgtacag aactcgtacg ctgcaggtcg             60
accacccgcg cgagaagatc ggaagagcac acgtctgaac tccagtcact taggcatctc            120
gtatgccgtc ttctgcttga aaaaaaaaaa                                             150
```

<210> SEQ ID NO 35
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 35

```
gtggggatg tccacgaggt ctctacacgg ctctcaatct accgcgtacg ctgcaggtcg              60
accacgtgaa ggacagggcg cagatcggaa gagcacacgt ctgaactcca gtcacttagg            120
catctcgtat gccgtcttct gcttgaaaaa                                             150
```

<210> SEQ ID NO 36
<211> LENGTH: 148
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t

<400> SEQUENCE: 36

```
gcgatcggtg tcggtctcgt aggtgccccc cggaacctct cacgtacgct gcaggtcgac             60
caccgtcgac ccagatcgga agagcacacg tctgaactcc agtcacttag gcatctcgtn            120
tgccgtcttc tgcntgaaaa aaaaaaaa                                               148
```

<210> SEQ ID NO 37
<211> LENGTH: 150
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 37

```
ggagaggatg tccacgaggt ctctcgccgt ggtcctcttc ccaccgtacg ctgcaggtcg             60
accacgactc gtcgaaggtg acccaggtag atcggaagag cacacgtctg aactccagtc            120
acttaggcat ctcgtatgcc gtcttctgct                                             150
```

<210> SEQ ID NO 38
<211> LENGTH: 150
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 38

```
cacgtggatg tccacgaggt ctctgaaaga tccttacgcc gttgcgtacg ctgcaggtcg      60
accacccatg ctacttatga gtaagatcgg aagagcacac gtctgaactc cagtcactta     120
ggcatctcgt atgccgtctt ctgcttgaaa                                       150
```

<210> SEQ ID NO 39
<211> LENGTH: 150
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 39

```
ttcaaagatg tccacgaggt ctctagccac catggataag aacccgtacg ctgcaggtcg      60
accacgtgta gatcggaaga gcacacgtct gaactccagt cacttaggca tctcgtatgc     120
cgtcttctgc ttgaaaaaaa aaaaaaaaaa                                       150
```

<210> SEQ ID NO 40
<211> LENGTH: 150
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 40

```
ggggcagatg tccacgaggt ctctaccatg aaaatcgcag agatcgtacg ctgcaggtcg      60
accactacac atctaacggt ggtgaccgtc cgtatagcgg acagatcgga agagcacacg     120
tctgaactcc agtcacttag gcatctcgta                                       150
```

<210> SEQ ID NO 41
<211> LENGTH: 150
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 41

```
gttgcggatg tccacgaggt ctcttgtcgg catcacctcg caatcgtacg ctgcaggtcg      60
accacgagcg ggacggccgg ccgggaggca acgagatcgg aagagcacac gtctgaactc     120
cagtcactta ggcaactcgt atgccgtctt                                       150
```

<210> SEQ ID NO 42
<211> LENGTH: 150
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 42
tcaacagatg tccacgaggt ctctacctcc gaagtttccg catccgtacg ctgcaggtcg    60
accaccgctc cgccttcacc gccaggaacg agatcggaag agcacacgtc tgaactccag   120
tcacttaggc atctcgtatg ccgtcttctg    150

<210> SEQ ID NO 43
<211> LENGTH: 79
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (58)..(63)
<223> OTHER INFORMATION: n is a, c, g, or t

<400> SEQUENCE: 43
atgatacggc gaccaccgag atctacactc tttccctaca cgacgctctt ccgatctnnn    60
nnncggtgtc ggtctcgta    79

<210> SEQ ID NO 44
<211> LENGTH: 71
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (35)..(54)
<223> OTHER INFORMATION: n is a, c, g, or t

<400> SEQUENCE: 44
gtgtaagtaa gtaagaaaac gagctcgaac atcgnnnnnn nnnnnnnnnn nnnnctacga    60
gaccgacacc g    71

<210> SEQ ID NO 45
<211> LENGTH: 81
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (59)..(63)
<223> OTHER INFORMATION: n is a, c, g, or t

<400> SEQUENCE: 45
aatgatacgg cgaccaccga gatctacact ctttccctac acgacgctct tccgatctnn    60
nnngtcgacc tgcagcgtac g    81

<210> SEQ ID NO 46
<211> LENGTH: 91
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (31)..(50)
<223> OTHER INFORMATION: n is a, c, g, or t

<400> SEQUENCE: 46
gtaagtaaga aaacgagctc gaattcatcg nnnnnnnnnn nnnnnnnnnn ctacgagacc    60

```
gacaccgagg atctccaggc atcaaataaa a                                 91
```

<210> SEQ ID NO 47
<211> LENGTH: 96
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (28)..(47)
<223> OTHER INFORMATION: n is a, c, g, or t

<400> SEQUENCE: 47

```
ttacacgtgg tcgacctgca gcgtacgnnn nnnnnnnnn nnnnnnnaga gacctcgtgg   60
acatcattca ccaccctata gtgagtcgta ttatga                            96
```

<210> SEQ ID NO 48
<211> LENGTH: 2579
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (70)..(89)
<223> OTHER INFORMATION: n is a, c, g, or t
<220> FEATURE:
<221> NAME/KEY: misc_feature
<222> LOCATION: (147)..(166)
<223> OTHER INFORMATION: n is a, c, g, or t

<400> SEQUENCE: 48

```
gcgcccggaa gagagtcaat tcataatacg actcactata gggtggtgaa tgatgtccac   60
gaggtctctn nnnnnnnnnn nnnnnnnnnc gtacgctgca ggtcgaccac gtgtaagtaa  120
gtaagaaaac gagctcgaat tcatcgnnnn nnnnnnnnnn nnnnnnctac gagaccgaca  180
ccgaggatct ccaggcatca aataaaacga aaggctcagt cgaaagactg ggcctttcgt  240
tttatctgtt gtttgtcggt gaacgctctc tactagagtc acactggctc accttcgggt  300
gggcctttct gcgtttatac ctaggctaca gccgatagtc tggaacagcg cacttacggg  360
ttgctgcgca acccaagtgc taccggcgcg gcagcgtgac ccgtgtcggc ggctccaacg  420
gctcgccatc gtccagaaaa cacggctcat cgggcatcgg caggcgctgc tgcccgcgcc  480
gttcccattc ctccgtttcg gtcaaggctg gcaggtctgg ttccatgccc ggaatgccgg  540
gctggctggg cggctcctcg ccggggccgg tcggtagttg ctgctcgccc ggatacaggg  600
tcgggatgcg gcgcaggtcg ccatgcccca acagcgattc gtcctggtcg tcgtgatcaa  660
ccaccacggc ggcactgaac accgacaggc gcaactggtc gcggggctgg ccccacgcca  720
cgcggtcatt gaccacgtag gccaacacg tgccggggcc gttgagcttc acgacggaga  780
tccagcgctc ggccaccaag tccttgactg cgtattggac cgtccgcaaa gaacgtccga  840
tgagcttgga aagtgtcttc tggctgacca ccacggcgtt ctggtggccc atctgcgcca  900
cgaggtgatg cagcagcatt gccgccgtgg gtttcctcgc aataagcccg gcccacgcct  960
catgcgcttt gcgttccgtt tgcacccagt gaccgggctt gttcttggct tgaatgccga 1020
tttctctgga ctgcgtggcc atgcttatct ccatgcggta ggggtgccgc acggttgcgg 1080
caccatgcgc aatcagctgc aacttttcgg cagcgcgaca caattatgc gttgcgtaaa 1140
```

```
agtggcagtc aattacagat tttctttaac ctacgcaatg agctattgcg ggggtgccg     1200 caatgagctg ttgcgtaccc ccctttttta agttgttgat ttttaagtct ttcgcatttc    1260
gccctatatc tagttctttg gtgcccaaag aagggcaccc ctgcggggtt ccccacgcc     1320 ttcggcgcgg ctcccctcc ggcaaaaagt ggcccctccg gggcttgttg atcgactgcg     1380
cggccttcgg ccttgcccaa ggtggcgctg ccccccttgga acccccgcac tcgccgccgt   1440
gaggctcggg gggcaggcgg gcgggcttcg cccttcgact gccccactc gcataggctt     1500 gggtcgttcc aggcgcgtca aggccaagcc gctgcgcggt cgctgcgcga gccttgaccc    1560
gccttccact tggtgtccaa ccggcaagcg aagcgcgcag gccgcaggcc ggaggcacta    1620
gtgcttggat tctcaccaat aaaaaacgcc cggcggcaac cgagcgttct gaacaaatcc    1680
agatggagtt ctgaggtcat tactggatct atcaacagga gtccaagcga gctcgatatc   1740
aaattacgcc ccgccctgcc actcatcgca gtactgttgt aattcattaa gcattctgcc   1800
gacatggaag ccatcacaaa cggcatgatg aacctgaatc gccagcggca tcagcacctt   1860
gtcgccttgc gtataatatt tgcccatggt gaaaacgggg gcgaagaagt tgtccatatt   1920
ggccacgttt aaatcaaaac tggtgaaact cacccaggga ttggctgaga cgaaaaacat   1980
attctcaata aacccttag ggaaataggc caggttttca ccgtaacacg ccacatcttg     2040
cgaatatatg tgtagaaact gccggaaatc gtcgtggtat tcactccaga gcgatgaaaa  2100
cgtttcagtt tgctcatgga aaacggtgta acaaggtga acactatccc atatcaccag    2160
ctcaccgtct ttcattgcca tacgaaattc cggatgagca ttcatcaggc gggcaagaat   2220
gtgaataaag gccggataaa acttgtgctt atttttcttt acggtcttta aaaaggccgt   2280
aatatccagc tgaacggtct ggttataggt acattgagca actgactgaa atgcctcaaa   2340
atgttcttta cgatgccatt gggatatatc aacggtggta tatccagtga tttttttctc   2400
cattttagct tccttagctc ctgaaaatct cgataactca aaaaatacgc ccggtagtga   2460
tcttatttca ttatggtgaa agttggaacc tcttacgtgc cgatcaacgt ctcattttcg   2520
ccagatatcg acgtcgacac catcgaatgg tgcaaaacct ttcgcggtat ggcatgata    2579
```

<210> SEQ ID NO 49
<211> LENGTH: 5156
<212> TYPE: DNA
<213> ORGANISM: Artificial Sequence
<220> FEATURE:
<223> OTHER INFORMATION: note="Description of Artificial Sequence: Synthetic Oligonucleotide"
<220> FEATURE:
<221> NAME/KEY: misc_feature
<222> LOCATION: (3091)..(3110)
<223> OTHER INFORMATION: n is a, c, g, or t
<220> FEATURE:
<221> NAME/KEY: misc_feature
<222> LOCATION: (3168)..(3187)
<223> OTHER INFORMATION: n is a, c, g, or t

<400> SEQUENCE: 49

```
cgcgctcctg cggcggcctg tagggcaggc tcatacccct gccgaaccgc ttttgtcagc     60
cggtcggcca cggcttccgg cgtctcaacg cgctttgaga ttcccagctt ttcggccaat    120
ccctgcggtg cataggcgcg tggctcgacc gcttgcgggc tgatggtgac gtggcccact   180
ggtggccgct ccagggcctc gtagaacgcc tgaatgcgcg tgtgacgtgc cttgctgccc   240
tcgatgcccc gttgcagccc tagatcggcc acagcggccg caaacgtggt ctggtcgcgg   300
gtcatctgcg ctttgttgcc gatgaactcc ttggccgaca gctgccgtc ctgcgtcagc     360
```

-continued

```
ggcaccacga acgcggtcat gtgcgggctg gtttcgtcac ggtggatgct ggccgtcacg    420
atgcgatccg ccccgtactt gtccgccagc cacttgtgcg ccttctcgaa gaacgccgcc    480
tgctgttctt ggctggccga cttccaccat tccgggctgg ccgtcatgac gtactcgacc    540
gccaacacag cgtccttgcg ccgcttctct ggcagcaact cgcgcagtcg gcccatcgct    600
tcatcggtgc tgctggccgc ccagtgctcg ttctctggcg tcctgctggc gtcagcgttg    660
ggcgtctcgc gctcgcggta ggcgtgcttg agactggccg ccacgttgcc cattttcgcc    720
agcttcttgc atcgcatgat cgcgtatgcc gccatgcctg cccctcccttt tggtgtcca    780
accggctcga cggggggcagc gcaaggcggt gcctccggcg ggccactcaa tgcttgagta    840
tactcactag actttgcttc gcaaagtcgt gaccgcctac ggcggctgcg gcgccctacg    900
ggcttgctct ccgggcttcg ccctgcgcgc tcgctgcgct cccttgccag cccgtggata    960
tgtggacgat ggccgcgagc ggccaccggc tggctcgctt cgctcggccc gtggacaacc   1020
ctgctggaca gctgatggaa caggctgcgc ctgcccacga gcttgaccac agggattgcc   1080
caccggctac ccagccttcg accacatacc caccggctcc aactgcgcgg cctgcggcct   1140
tgccccatca atttttttaa ttttctctgg ggaaaagcct ccggcctgcg gcctgcgcgc   1200
ttcgcttgcc ggttggacac caagtggaag gcgggtcaag gctcgcgcag cgaccgcgca   1260
gcggcttggc cttgacgcgc ctggaacgac ccaagcctat gcgagtgggg gcagtcgaag   1320
gcgaagcccg ccccgcctgcc ccccgagcct cacggcggcg agtgcggggg ttccaagggg   1380
gcagcgccac cttgggcaag gccgaaggcc gcgcagtcga tcaacaagcc ccggaggggc   1440
cactttttgc cggagggggga gccgcgccga aggcgtgggg gaaccccgca ggggtgccct   1500
tctttgggca ccaaagaact agatataggg cgaaatgcga aagacttaaa aatcaacaac   1560
ttaaaaaagg ggggtacgca acagctcatt gcggcacccc ccgcaatagc tcattgcgta   1620
ggttaaagaa aatctgtaat tgactgccac ttttacgcaa cgcataattg ttgtcgcgct   1680
gccgaaaagt tgcagctgat tgcgcatggt gccgcaaccg tgcggcaccc taccgcatgg   1740
agataagcat ggccacgcag tccagagaaa tcggcattca agccaagaac aagcccggtc   1800
actgggtgca acggaacgc aaagcgcatg aggcgtgggc cgggcttatt gcgaggaaac   1860
ccacggcggc aatgctgctg catcacctcg tggcgcagat gggccaccag aacgccgtgg   1920
tggtcagcca gaagacactt tccaagctca tcggacgttc tttgcggacg gtccaatacg   1980
cagtcaagga cttggtggcc gagcgctgga tctccgtcgt gaagctcaac ggccccggca   2040
ccgtgtcggc ctacgtggtc aatgaccgcg tggcgtgggg ccagccccgc gaccagttgc   2100
gcctgtcggt gttcagtgcc gccgtggtgg ttgatcacga cgaccaggac gaatcgctgt   2160
tggggcatgg cgacctgcgc cgcatcccga ccctgtatcc gggcgagcag caactaccga   2220
ccggccccgg cgaggagccg cccagccagc ccggcattcc gggcatggaa ccagacctgc   2280
cagccttgac cgaaacggag gaatgggaac ggcgcgggca gcagcgcctg ccgatgcccg   2340
atgagccgtg ttttctggac gatggcgagc cgttggagcc gccgacacgg gtcacgctgc   2400
cgcgccggta gcacttgggt tgcgcagcaa cccgtaagtg cgctgttcca gactatcggc   2460
tgtagccgcc tcgccgccct ataccttgtc tgcctcccg cgttgcgtcg cggtgcatgg   2520
agccgggcca cctcgacctg aatggaagcc ggcggcacct cgctaacgga ttcaccgttt   2580
ttatcaggct ctgggaggca gaataaatga tcatatcgtc aattattacc tccacgggga   2640
gagcctgagc aaactggcct caggcatttg agaagcacac ggtcacactg cttccggtag   2700
tcaataaacc ggtaaaccag caatagacat aagcggctat ttaacgaccc tgccctgaac   2760
```

```
cgacgaccgg gtcgaatttg ctttcgaatt tctgccattc atccgcttat tatcacttat    2820
tcaggcgtag caccaggcgt ttaagggcac caataactgc cttaaaaaaa ttacgccccg    2880
ccctgccact catcgcagtc ggcctattgg ttaaaaaatg agctgattta acaaaaattt    2940
aacgcgaatt ttaacaaaat attaacgcat cgacgtcgac accatcgaat ggtgcaaaac    3000
ctttcgcggt atggcatgat agcgcccgga agagagtcaa ttcataatac gactcactat    3060
agggtggtga atgatgtcca cgaggtctct nnnnnnnnnn nnnnnnnnnn cgtacgctgc    3120
aggtcgacca cgtgtaagta agtaagaaaa cgagctcgaa ttcatcgnnn nnnnnnnnn    3180 nnnnnnncta cgagaccgac accgaggatc tccaggcatc aaataaaacg aaaggctcag    3240
tcgaaagact gggcctttcg ttttatctgt tgtttgtcgg tgaacgctct ctactagagt    3300
cacactggct caccttcggg tgggcctttc tgcgtttata cctaggagct gtttcctgtg    3360
tgaaattgtt atccgctcac aattccacac aacatacgag ccggaagcat aaagtgtaaa    3420
gcctggggtg cctaatgagt gagctaactc acattaattg cgttgcgctc actgcccgct    3480
ttccagtcgg gaaacctgtc gtgccagctg cattaatgaa tcggccaacg cgcggggaga    3540
ggcggtttgc gtattgggcg catgcataaa aactgttgta attcattaag cattctgccg    3600
acatggaagc catcacaaac ggcatgatga acctgaatcg ccagcggcat cagcaccttg    3660
tcgccttgcg tataatattt gcccatgggg gtgggcgaag aactccagca tgagatcccc    3720
gcgctggagg atcatccagc cggcgtcccg gaaaacgatt ccgaagccca acctttcata    3780
gaaggcggcg gtggaatcga aatctcgtga tggcaggttg ggcgtcgctt ggtcggtcat    3840
ttcgaacccc agagtcccgc tcagaagaac tcgtcaagaa ggcgatagaa ggcgatgcgc    3900
tgcgaatcgg gagcggcgat accgtaaagc acgaggaagc ggtcagccca ttcgccgcca    3960
agctcttcag caatatcacg ggtagccaac gctatgtcct gatagcggtc cgccacaccc    4020
agccggccac agtcgatgaa tccagaaaag cggccatttt ccaccatgat attcggcaag    4080
caggcatcgc catgggtcac gacgagatcc tcgccgtcgg gcatgcgcgc cttgagcctg    4140
gcgaacagtt cggctggcgc gagccccctga tgctcttcgt ccagatcatc ctgatcgaca    4200
agaccggctt ccatccgagt acgtgctcgc tcgatgcgat gtttcgcttg gtggtcgaat    4260
gggcaggtag ccggatcaag cgtatgcagc cgccgcattg catcagccat gatggatact    4320
ttctcggcag gagcaaggtg agatgacagg agatcctgcc ccggcacttc gcccaatagc    4380
agccagtccc ttcccgcttc agtgacaacg tcgagcacag ctgcgcaagg aacgcccgtc    4440
gtggccagcc acgatagccg cgctgcctcg tcctgcagtt cattcagggc accggacagg    4500
tcggtcttga caaaaagaac cgggcgcccc tgcgctgaca gccggaacac ggcggcatca    4560
gagcagccga ttgtctgttg tgcccagtca tagccgaata gcctctccac ccaagcggcc    4620
ggagaacctg cgtgcaatcc atcttgttca atcatgcgaa acgatcctca tcctgtctct    4680
tgatcagatc ttgatcccct gcgccatcag atccttggcg gcaagaaagc catccagttt    4740
actttgcagg gcttcccaac cttaccagag ggcgccccag ctggcaattc cggttcgctt    4800
gctgtccata aaaccgccca gtctagctat cgccatgtaa gcccactgca agctacctgc    4860
tttctctttg cgcttgcgtt ttcccttgtc cagatagccc agtagctgac attcatccca    4920
ggtggcactt tcggggaaa tgtgcgcgcc cgcgttcctg ctggcgctgg gcctgtttct    4980
ggcgctggac ttcccgctgt tccgtcagca gcttttcgcc cacggccttg atgatcgcgg    5040
cggccttggc ctgcatatcc cgattcaacg gccccagggc gtccagaacg ggcttcaggc    5100
```

```
<210> SEQ ID NO 50
<211> LENGTH: 15
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (14)..(15)
<223> OTHER INFORMATION: Phosphorothioate modification

<400> SEQUENCE: 50
acgctcttcc gatct                                                         15

<210> SEQ ID NO 51
<211> LENGTH: 32
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: misc_feature
<222> LOCATION: (1)..(1)
<223> OTHER INFORMATION: 5' phosphate modification

<400> SEQUENCE: 51
gatcggaaga gcacacgtct gaactccagt ca                                      32

<210> SEQ ID NO 52
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 52
agagtttgat cmtggctcag                                                    20

<210> SEQ ID NO 53
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 53 cggttaccttgttacgactt                                                     20
```
gctcccgaag gtctcgggcc gtctcttggg cttgatcggc cttcttgcgc atctca        5156

MULTIPLEX CHARACTERIZATION OF MICROBIAL TRAITS USING DUAL BARCODED NUCLEIC ACID FRAGMENT EXPRESSION LIBRARY

RELATED APPLICATIONS

The present application claims priority under 35 U.S.C. § 119(e) to U.S. Provisional Application No. 62/369,699, filed on Aug. 1, 2016. The content of this related application is hereby expressly incorporated by reference in its entirety.

STATEMENT REGARDING FEDERALLY SPONSORED R&D

This invention was made with government support under grant Nos. DE No. DE-AC02-05CH11231 awarded by the U.S. Department of Energy. The government has certain rights in the invention.

REFERENCE TO SEQUENCE LISTING

The present application is being filed along with a Sequence Listing in electronic format. The Sequence Listing is provided as a file entitled Sequence_Listing_LBNL_080A.txt, created Jul. 30, 2017, which is 33,352 bytes in size. The information in the electronic format of the Sequence Listing is incorporated herein by reference in its entirety.

BACKGROUND

Advances in cultivation-independent sequencing have had a tremendous impact on genomic research. Vast number of microbes and microbial communities from diverse contexts have been sequenced, bioinformatically studied and predictions have been made about their basic biology, taxonomy, coding potential and functional role in environments. Single-cell genomics (SCG) has enabled the discovery of new bacterial phyla, some of which consist of smaller genomes and lacking key metabolic pathways that are essential for independent growth (Brown et. al. (2013) Nature 523: 208, Rinke et. al. (2013) Nature 499: 431). It is postulated that given their great evolutionary distance to cultivated microbes, these organisms may harbor potentially novel functions useful for biotechnology applications.

However, due to the ever-increasing number of fully sequenced genomes and their automatic annotation using comparative genomics of phylogenetically distant and poorly characterized gene-function per cultivated organisms, the knowledge-gap in sequence-to-function is widening rapidly. Among the vast number of sequenced microbes, only a handful of them have been experimentally characterized for functions and fitness traits (partly because of uncultivatibility of most microorganisms). Though, current state-of-the-art technologies such as RNA-Seq, metabolomics, functional metagenomics and transposon mutagenesis coupled with next generation sequencing have been helping to fill some of the knowledge gap in sequence-to-function space (Biteen, J. S. et al. Tools for the Microbiome: Nano and Beyond. *ACS Nano* 10, 6-37, (2016); Leis et al., (2013) Screening and expression of genes from metagenomes. Advances in applied microbiology, Vol 83, 2-68; Blaser, M. J. et al. Toward a Predictive Understanding of Earth's Microbiomes to Address 21st Century Challenges. *MBio* 7, 00714-16 (2016)), These methods can neither be fully and effectively extended to uncultivated microbes (that makeup ~95-99% of microbial diversity in most ecosystems) nor to amplified genomes from Single-Cell Genomics (SCG) technology.

Novel experimental and computational tools and technologies for discovering and interconnecting gene functions within individual microbes and microbial communities in the field are needed. The development of high-throughput tools such as randomly barcoded transposon sequencing (RB-TnSeq) for cultivable microorganisms to rapidly generate loss-of-function mutant phenotypes has been an important milestone in the field, but it remains a challenge to infer functions of essential genes and genes without a significant loss-of-function phenotype as single mutations (Wetmore et al (2015) Rapid quantification of mutant fitness in diverse bacteria by sequencing randomly barcoded transposons (RB-TnSeq). mBio 6(3):e00306-15). In addition, cultivating and mutagenizing most microbial isolates from the field is not feasible.

One complementary approach has been to generate shotgun expression libraries from genomic/metagenomic samples to perform gain-of-function assays. In its current form this approach is low throughput, expensive, labor-intensive and has a limited potential to capture the genomic and functional diversity in metagenomic samples. As these screens are typically performed only in *Escherichia coli*, they exhibit low success rate due to host-specific issues such as toxicity and expression bottlenecks. There is an urgent need for a standardized high-throughput characterization technology that is scalable, quantitative, less laborious, cheaper, and allows multiplex trackable quantification of microbial fitness under hundreds of conditions in different organisms. Such a technology will provide access to the unexplored sequence-function space of hundreds to thousands of microbial genomes including the uncultivable ones and offer novel solutions in bioprospecting and functional genomics.

SUMMARY

Some embodiments disclosed herein provide methods of constructing an expression library, comprising: providing a plurality of nucleic acid fragments; providing a plurality of vectors each comprising a first barcode and a second barcode; and inserting the plurality of nucleic acid fragments into the plurality of vectors to generate a plurality of expression vectors, wherein each expression vector comprises a nucleic acid fragment from the plurality of nucleic acid fragments flanked by the first barcode and the second barcode. In some embodiments, the methods further comprise transforming the plurality of expression vectors into a host organism. In some embodiments, the host organism is selected from bacteria, yeast, fungi, insect cells, mammalian cells, plant cells, and any combination thereof. In some embodiments, the plurality of nucleic acid fragments is from a single cell, a plurality of cells, a tissue sample, a virus, a fungus, or any combination thereof. In some embodiments, the plurality of nucleic acid fragments is a plurality of genomic fragments. In some embodiments, the plurality of genomic fragments comprises a sequenced genome, a single cell genome, a viral genome, a bacterial genome, a metagenome, or any combination thereof. In some embodiments, the plurality of nucleic acid fragments has an average size of 100 bp to 300 kb. In some embodiments, the first barcode and the second barcode are randomly generated or selected from a set of diverse barcodes. In some embodiments, the set of diverse barcodes comprises at least 100 unique barcodes. In some embodiments, the set of diverse barcodes comprises at least 1,000 unique barcodes. In some embodiments, the set of diverse barcodes comprises at least 10,000 unique barcodes. In some embodiments, the methods further comprise sequencing the plurality of expression vectors. In some embodiments, sequencing comprises sequencing at least a portion of the first barcode, the second barcode, and the nucleic acid fragment. In some embodiments, the methods further comprise associating the sequence of the first barcode or the sequence of the second barcode with the sequence of the nucleic acid fragment. In some embodiments, each of the plurality of vectors comprises a promoter. In some embodiments, the promoter is selected from the group consisting of a constitutive promoter, a synthetic promoter, an inducible promoter, an endogenous promoter, an exogenous promoter, and any combination thereof.

Some embodiments disclosed herein provide barcoded expression libraries comprising a plurality of expression vectors, wherein each expression vector comprises a nucleic acid fragment flanked by a first barcode and a second barcode. In some embodiments, the vector is selected from the group consisting of plasmids, viral vectors, cosmids, fosmids, and artificial chromosomes. In some embodiments, the vector is selected from the group consisting of IncQ, IncW, IncP, and pBBR1. In some embodiments, the vector is a plant plasmid, a bacterial plasmid, a yeast plasmid, a worm plasmid, an insect plasmid, a mammalian plasmid, or any combination thereof. In some embodiments, the expression libraries comprise a host organism. In some embodiments, the host organism is selected from bacteria, yeast, fungi, insect cells, mammalian cells, plant cells, and any combination thereof. In some embodiments, the host organism is a bacterium. In some embodiments, the host organism is selected from the group consisting of *E. coli*, *Pseudomonas* sp., *Cupriavidus* sp. and *Acidovorax* sp. In some embodiments, the host can be an animal (such as a fish, a mouse, a rat, a chicken, a bovine, a zebrafish), a fly, a nematode, a yeast, a weed, or any combination thereof. In some embodiments, the plurality of nucleic acid fragments comprises at least 70% coding sequences for single proteins and small operons of a donor organism. In some embodiments, the plurality of nucleic acid fragments comprises at least 80% coding sequences for single proteins and small operons of a donor organism. In some embodiments, the plurality of nucleic acid fragments comprises at least 9% coding sequences for single proteins and small operons of a donor organism. In some embodiments, the nucleic acid fragments are cDNA and can be associated with one barcode. In some embodiments, the plurality of nucleic acid fragments comprises at least 95% coding sequences for single proteins and small operons of a donor organism. In some embodiments, the donor organism is selected from bacteria, yeast, fungi, insect cells, mammalian cells, plant cells, and any combination thereof. In some embodiments, the plurality of nucleic acid fragments comprise a sequenced genome, a single cell genome, a viral genome, a bacterial genome, a metagenome, or any combination thereof. In some embodiments, the plurality of nucleic acid fragments are from a single cell, a plurality of cells, a tissue sample, a virus, a fungus, or any combination thereof. In some embodiments, the plurality of nucleic acid fragments has an average size of 100 bp to 300 kb.

Some embodiments disclosed herein provide methods of conducting functional analysis comprising: transforming a test organism with an barcoded expression library comprising a plurality of expression vectors, wherein each expression vector comprises a nucleic acid fragment flanked by a first barcode and a second barcode; subjecting the transformed test organism to a stress condition; collecting the expression vectors from the test organism subjected to the stress condition; and identifying a nucleic acid fragment that is resistant to the stress condition. In some embodiments, the test organism is selected from bacteria, yeast, fungi, insect cells, mammalian cells, plant cells, and any combination thereof. In some embodiments, the stress condition comprises metal tolerance/resistance, diverse aromatic carbon tolerance/utilization, diverse carbon, and nitrogen sources, antibiotics, virus, phage, toxic stress, nutrients, physical condition such as temperature, pH, salt, UV light, light, supernatant of cell culture, plant extract, soil, water, any other environment or any combination thereof. In some embodiments, identifying the nucleic acid fragment comprises quantitative analysis of unique barcodes from the collected expression vectors. In some embodiments, the quantitative analysis comprises using a computer program. In some embodiments, the computer program counts the number of unique barcodes from the collected expression vectors. In some embodiments, quantitative analysis of unique barcodes comprises sequencing at least a portion of the first barcode, the second barcode, or the nucleic acid fragment. In some embodiments, quantitative analysis of unique barcodes comprises sequencing at least a portion of the first barcode. In some embodiments, quantitative analysis of unique barcodes comprises sequencing at least a portion of the second barcode. In some embodiments, the sequencing comprises paired end sequencing. In some embodiments, the sequencing comprises single end sequencing.

BRIEF DESCRIPTION OF THE DRAWINGS

FIG. 8 panels (a)-(e) show a non-limiting schematic illustration of Barcode-Association with-Genome Fragment (BAGseq) of the up tag.

FIG. 9 panels (a)-(c) show a non-limiting schematic illustration of Barcode-Association with-Genome Fragment (BAGseq) of the down tag.

FIG. 10 panels (a)-(b) show non-limiting exemplary plots comparing good and bad library preparations.

FIG. 11 panels (a)-(c) show non-limiting exemplary schematic method to PCR out of the up tag.

FIG. 14 panels (a)-(f) are non-limiting exemplary plots showing snapshot of fitness data of *E. coli* Dubseq library. A chosen few genes with highest fitness scores for each of 6 stress conditions are shown. Insets give general mechanism of stress tolerance or pathway involved. Genes involved in genomic fragments are shown.

DETAILED DESCRIPTION

Definitions

Figure 1:
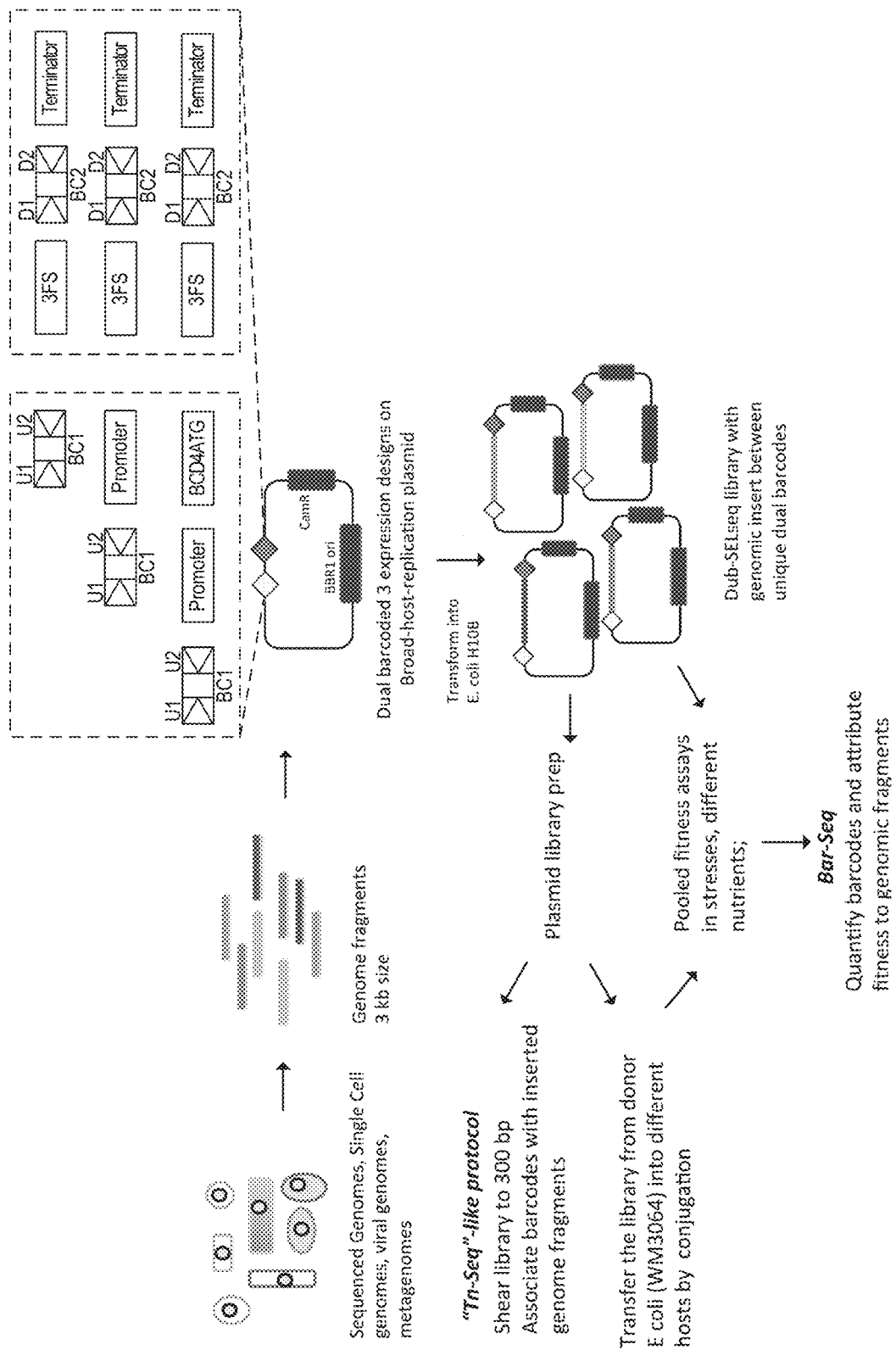
FIG. 1 shows a schematic illustration of an exemplary Dub-seq (Dual barcoded Shotgun Expression library sequencing) characterization pipeline.

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "barcode" or "barcodes" can refer to nucleic acid codes or sequences associated with a target within a sample. A barcode can be, for example, a nucleic acid label. A barcode can be an entirely or partially amplifiable barcode. A barcode can be entirely or partially sequenceable barcode. A barcode can be a portion of a native nucleic acid that is identifiable as distinct. A barcode can be a known sequence. A barcode can be a random sequence. A barcode can comprise a junction of nucleic acid sequences, for example a junction of a native and non-native sequence. As used herein, the term "barcode" can be used interchangeably with the terms, "index", "tag," or "label-tag." Barcodes can convey information. For example, in various embodiments, barcodes can be used to determine an identity of a nucleic acid, a source of a nucleic acid, an identity of a cell, and/or a target.

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3 '-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (Hpyrido(3',':4,5)pyrrolo[2,3-d]pyrimidin-2-one).

Advances in DNA sequencing have enabled the sequencing of thousands of living forms yet provided only limited information on gene function, biology or the dynamics of these living forms in the ecosystem and their use in various biotechnologies. For example, while microbial enzymes, small molecules and their derivatives are a multi-billion market annually such commercial products have been isolated or derived from less than 1% of the known microbial world. Technologies for resolving roles of uncharacterized genes with high throughput and high accuracy are needed. Disclosed herein are Dub-seq systems and methods that can enable the study of DNA expression libraries under hundreds of conditions in some embodiments. This technology is quantitative, economical, and provides an alternative tool for driving the early success of sourcing microbiomes for energy, environment and biomanufacturing applications.

In some embodiments, the Dub-seq technology can employ a simple workflow of inserting DNA fragment from any source between two random DNA barcodes (e.g., random series of twenty A, T, G, C's, components of DNA) and study the fragment-encoded gene functions in diverse hosts and conditions. Once the DNA barcode is associated with a specific DNA fragment, the smaller barcode is used as a proxy for the DNA fragment. This association is done only once for every library. Next, Dubseq library is moved into a host platform (bacteria, fungi, plant and animal model systems) and the function imparted by barcoded DNA fragment to the host is studied under different conditions.

Since the Dub-seq technology is flexible and scalable, the same library can be used to test with other hundreds of stress conditions, nutrients, metals and toxic chemicals and study their tolerance traits. For example, the same library can be used to assess which genes or gene fragments yield us tolerance to pesticides or metals that may be important in engineering plants or agricultural produce. As compared to other methods, some embodiments of the Dub-seq technology save time, money and labor to discover new functions.

For example, the Dub-seq technology can be used to improve the biofuel production in a bacterium. One goal can be to improve the tolerance of bacteria to the toxic effects of the biofuel. Biofuels are chemicals like fuels and are toxic to all living forms, as they damage the cell wall and cause cell death. However, there are some bacteria and fungi that grow in or around oilfields and are known to have evolved mechanisms to tolerate highly toxic chemicals. By sourcing these traits and engineering them into bacteria, the bacteria's biofuel tolerance limits can increase, enabling increased biofuel production yields. In some embodiments, genomic DNA from microbes growing around oil-fields is extracted and Dub-seq library is made. The dual barcodes can be associated with genomic fragments and moved into the host bacteria. The bacteria with Dub-seq library are then grown in presence of different levels of biofuel and surviving bacteria are collected. By extracting barcodes before and after the biofuel treatments, the bacteria (e.g., barcodes) that survive the biofuel treatment can be evaluated. It is possible then to trace-back which fragments are present in the surviving bacteria. The repeat use of the same Dub-seq library can save time, money and labor resources in some embodiments.

Methods of Quantitative Analysis of Nucleic Acid Target Molecules

One challenge facing genomics is the ever-increasing knowledge gap between sequence and its encoded function. Gain-of-function methods are attractive avenues for phenotype-based functional screens, but are not amenable to high-throughput assays across hundreds of conditions due to either the need for laborious and expensive sample preparation after every screen or the very low throughout strain archiving protocols.

Advances in cultivation-independent DNA sequencing have had a tremendous impact on genomic research. Thousands of microbial genomes, metagenomes and single cell genomes have been sequenced, bioinformatically studied and predictions have been made about gene function, the architecture of microbial communities, and the context specific functional potential of microorganisms. Among this vast number of sequenced microbes, only a handful of them have been experimentally characterized for functions partly because of uncultivatibility of most microorganisms and lack of genetic tools for others.

Current state-of-the-art technologies such as gene-knockout libraries, transposon mutagenesis, and CRISPRi coupled with next generation sequencing have been helping to fill some of the knowledge gap in sequence-to-function space. Recently developed High-throughput tools such as randomly barcoded transposon sequencing (RB-TnSeq) for cultivable microorganisms is allowing deeper experimental annotation of function than previously possible. However it remains a challenge to infer functions of essential genes and genes without a significant loss-of-function phenotype as single mutations. In addition, cultivating and mutagenizing most microbial isolates from diverse environments is not feasible and finally, these technologies cannot be extended to metagenomic samples and single amplified genomes.

One complementary approach for studying gene function is to generate gain-of-function overexpression libraries. Overexpression as a genetic tool has a rich history of connecting overexpression of a gene to cellular function and has been exploited as a versatile screening technique to study diseases, discovering drug targets, genetic interactions, function complementation or multicopy suppression, and as a therapeutic intervention. Technologies employed for overexpression studies include ordered gene (ORF) overexpression libraries, shotgun expression libraries, and activation modes of transposon insertion or CRISPR systems. Among these, ORF libraries, however useful, scaling it to hundreds of microbes is not practical. Activation modes of transposon insertion or CRISPR systems, even though promising, have not been applied to many microbes may be due to lack of genetic tools. Owing to its simplicity in design and easier applicability to study uncultureable microbes, shotgun expression library approach has been widely used for doing gain-of-function assays.

In shotgun expression library approach, the genomic DNA or cDNA can be sheared to different size fragments, cloned on a replicable or genomic insertion vector, and moved into a host system for doing assays. This approach has been a method of choice for studying gene-function in microbial isolates and metagenomic samples (examples) and has been employed in diverse biotechnologies. Most shotgun expression libraries have been assayed in only handful of conditions (for example, antibiotics) looking for a specific gene-function (antibiotic resistance) and have suffered very low hit rates for identifying intended function. Also, the process needs tedious and expensive archiving and sequencing protocols for identifying the sequence of winning candidates. With arrival of next generation sequencing technologies, all winning candidates can be pooled and shotgun sequenced using commercial sample preparation kits. Even though the sequencing is getting cheaper, this workflow of sample preparation quickly becomes cost-prohibitive and labor intensive if the overexpression library needs to be assayed in hundreds of conditions to generate broad function profile for a library or to perform time series sampling to study function dynamics.

The 'Dub-seq' technology disclosed herein, in some embodiments, combines shotgun expression library method with barcoding. For example, a dual barcoded library can be generated on a broad-host plasmid system, clone diverse microbial genome fragments (including genomic fragments of environmental isolates) between the dual barcodes and associate their pairings using high-throughput sequencing, and finally perform gain-of-function pooled fitness assays in the model host organism *Escherichia coli* and other proteobacteria under diverse nutrient and stress conditions. This technology can also be broadly applicable in building a functional compendium of genome fragments from diverse single amplified genomes, viruses, phages, metagenomes, and is easily extendable to eukaryotes. In some embodiments, Dub-seq can increase the throughput of functional screens by using barcode sequencing (BarSeq) to assess the gene function via fitness measurements. In some implementations, Dub-seq can be used for gain-of-function characterization technology that is high-throughput, scalable, quantitative, less laborious, cheaper and can allow multiplex trackable quantification of microbial fitness under hundreds of conditions in different organisms and can be easily extended for different biotechnologies. In some embodiments, the systems and methods disclosed herein can be low cost, scalable, repeatable, sharable, have application flexibility, or any combination thereof.

The 'Dub-seq' technology disclosed herein, in some embodiments, can be used to understand gene-function and extract the knowledge of gene-function, thus improving numerous biotechnologies and hence have tremendous potential. In some implementations, the DubSeq technology is a high-throughput, scalable, flexible functional characterization technology based on creating pooled libraries of double barcoded DNA fragments. It can provide a quantitative and faster tool for assessing gene-function of DNA isolated from any source or environment. The workflow is simple and more cost effective than currently available technologies and is extendable to diverse applications. This includes functional genomics of microorganisms, viruses, microbiomes, human/animal parasites, human, animal, insects, worms and plant genomes. With this technology, rapid tests in hundreds to thousands of conditions using the same library can be created and easily shared between laboratories. The technology can improve experimental reproducibility and aids repeatability at minimal expense, labor and time. The Dub-seq technology can be applicable in discovery of novel enzymes/biocatalysts for biofuel production, improving and tolerance traits for toxic biochemicals, ensemble functional assessment of microbial communities, plant growth promoting factors, bioremediation routes, novel green chemistries and biotechnologies in improving energy and environment missions. The technology is also extendable in diverse health and agriculture associated biotechnologies.

FIG. 1 shows an exemplary functional genome annotation by dual barcoded shotgun expression library on broad-host replication plasmid. The experimental designs can be as beat follows: dual barcodes on broad-host plasmid backbone can be deep sequenced to count unique barcode pairs; diverse microbial genomes are sheared to 3 Kb fragments, end repaired and cloned into dual barcoded plasmid by blunt end ligation protocol. The ligation mixture can then be transformed into, for example, *E. coli* DH10B to generate the Dub-seq library and stored for further analysis. The plasmid library prepared from this library can be subjected to high-throughput sequencing to associate the barcode sequence to cloned genome fragment. The same plasmid library can be electroporated into, for example, *E. coli* APA11048 based on WM3064 conjugation donor strain and used for transferring the library into different hosts (*Pseudomonas* sp. *Cupriavidus metallidurans, Shewanella oneidensis* MR-1). The Dub-seq library can be subjected to diverse stress conditions and nutrients to do pooled fitness experiments in deep well plates. The high-throughput sequencing is used to count barcodes in no stress sample, condition/sample wells and control wells (no insert vector backbone), and used for analyzing the fitness measure.

Figure 2:
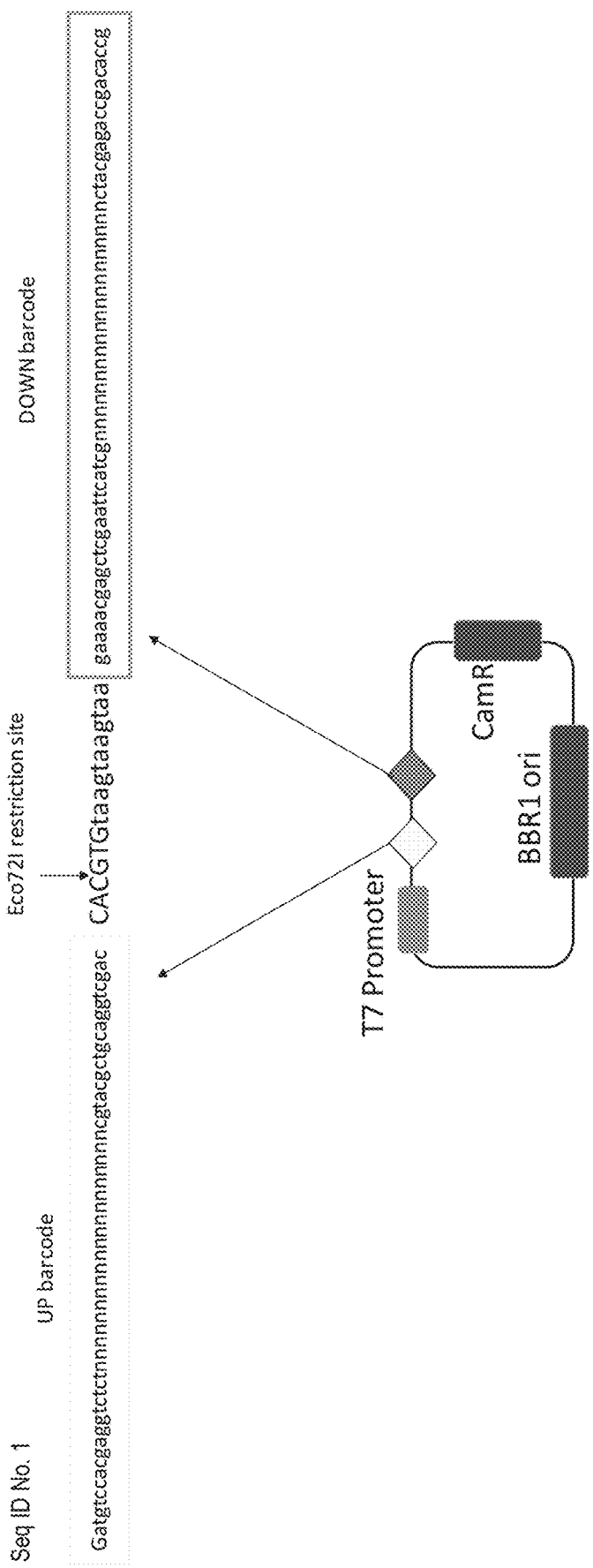
FIG. 2 is a non-limiting exemplary schematic illustration of a Dub-seq vector map with the sequence of the cloning region shown.
Figure 3:
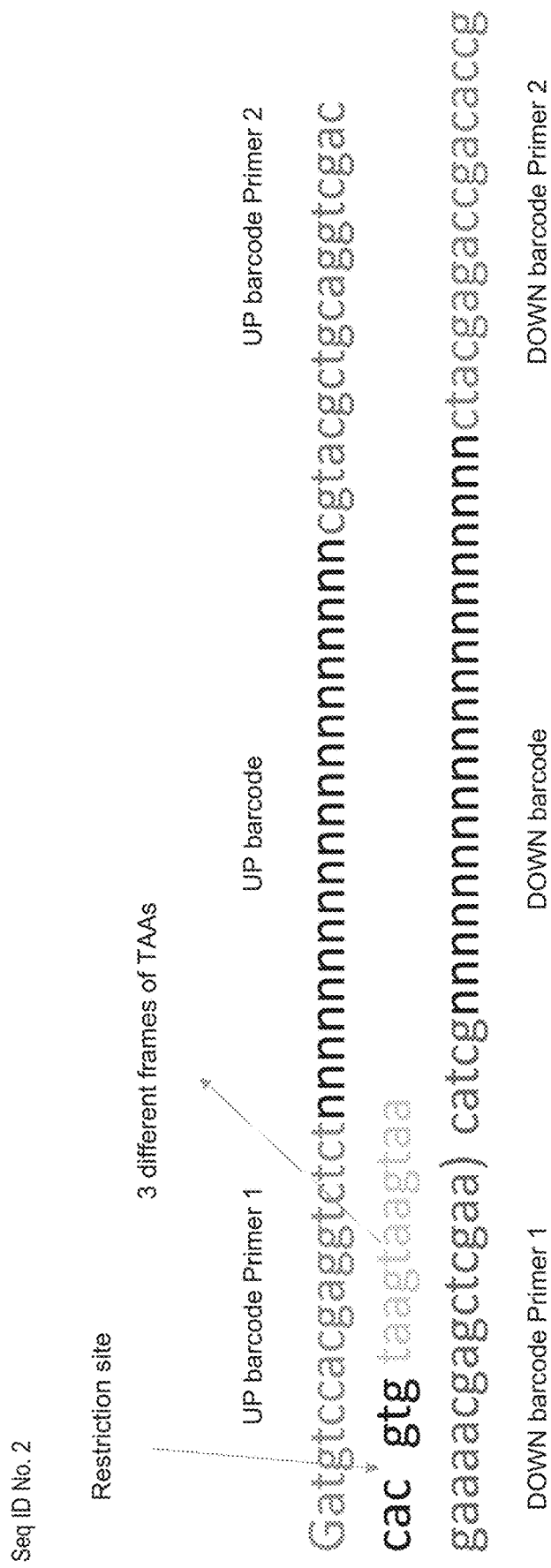
FIG. 3 is a non-limiting exemplary schematic illustration of the sequence of a Dub-seq cloning region.

A dual barcoded library on a broad-host plasmid system can be generated; SCG amplified fragments (about 3 Kb) can be cloned between the dual barcodes and associates with the due barcodes. FIG. 2 is a non-limiting exemplary schematic illustration of a Dub-seq vector map with the sequence of the cloning region shown. FIG. 3 is a non-limiting exemplary schematic illustration of the sequence of a Dub-seq cloning region. Each library of donor genomic fragments can be associated with dual barcodes only once and the microbial fitness conferred by heterologous DNA can be quantified by a BarSeq protocol (Smith et al. (2009) Genome Research 19: 1836-1842, Smith et al. (2010) Nucleic Acid Research 38: e142, the contents of which are hereby expressly incorporated by reference in their entireties) after assaying in model host organisms, such as *Escherichia coli* and *Pseudomonas putida*, across different nutrient and stress conditions. As the entire Dub-seq library can be on a broad-host plasmid, it can be assayed in other microbial hosts or mutants (e.g., single-gene deletion mutants for complementation assays). In some embodiments, the Dub-seq libraries can be assayed under diverse nutrient combinations, antibiotics and stress inducing compounds. To establish the technology for SCG samples, single-cell amplified genomes of *E. coli* can be used as a test case. Subsequently, SCG samples of candidates (e.g., phyla Omnitrophica/OP3, Aminicenantes/OP8 or WPS-2) can be used for Dub-seq platform. Omnitrophica and Aminicenantes are ubiquitous and found in an array of diverse environments, yet very little is known about their functional roles. Similarly, candidate phylum WPS-2 has been abundantly found in acid mine drains, and also in human calcified dental plaques, but the knowledge of their coding potential is very rudimentary. In some embodiments, Dub-seq platform can be used to study nutrient uptake modes and tolerance phenotypes for these organisms.

Dub-seq technology can be applied to SCG samples of recently discovered highly reduced genomes (probable ectosymbionts of other organisms) belonging to candidate phyla Parcubacteria/OD1 and Microgenomates/OP11 (Rinke et. al. (2013) Nature 499: 431, Brown et. al. (2013) Nature 523: 208). As these organisms lack some key metabolic pathways, and it has been postulated that they may have special transporters to uptake a variety of nutrients or may have special cell surface proteins that aid in microbe-microbe interaction. Having the Dub-seq library of these minimal organisms as a resource enables us to screen the gene function in variety of relevant conditions in their ecosystem.

In some embodiments, Dub-seq, a dual barcoded shotgun expression library sequencing approach, disclosed herein, decouples characterization of overexpression library from the identification of strain and gene fitness to solve above-mentioned key bottlenecks in gain-of-function workflows. In some embodiments, the Dub-seq approach combines the advantages of Tnseq, and Barseq methods for one time characterization of overexpressed library and scaling the competitive growth assays to hundreds of conditions. An *E. coli* Dub-seq library can be expressed and assayed in *E. coli* across more than one hundred conditions.

Figure 4:
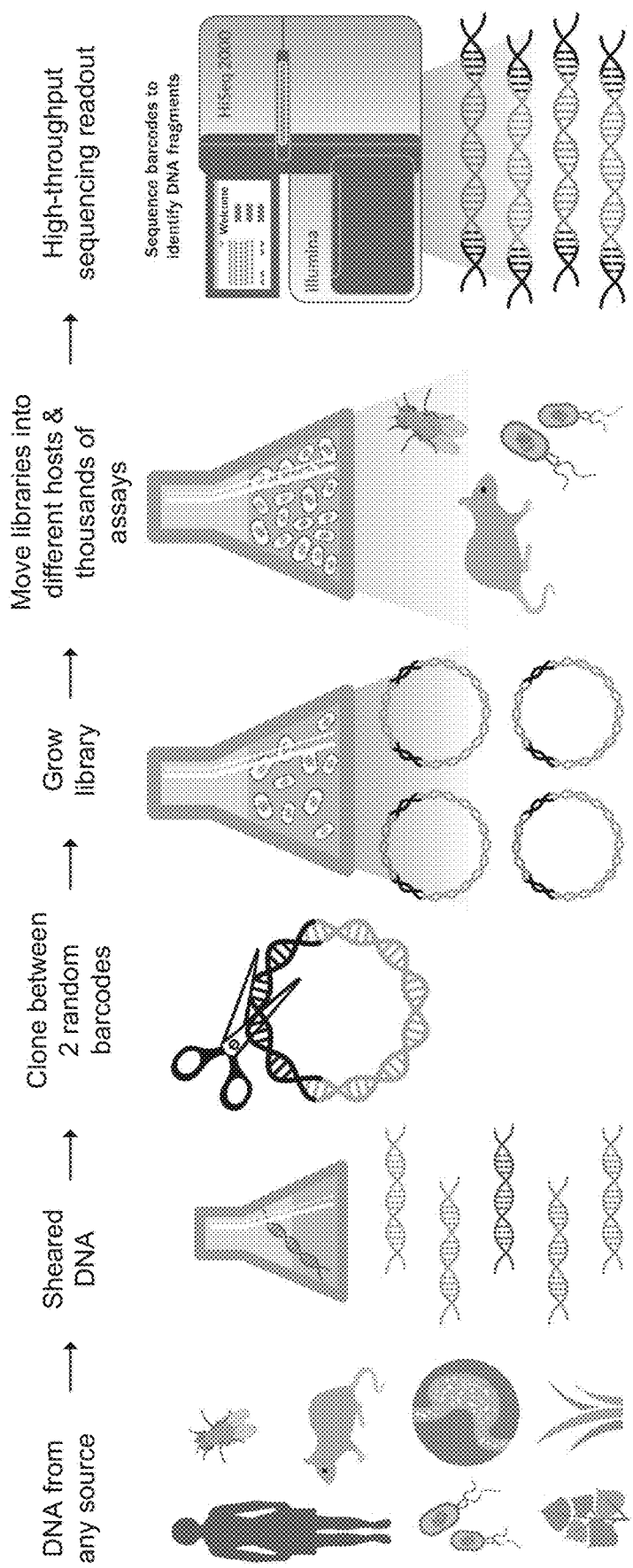
FIG. 4 is a non-limiting schematic illustration of a Dub-seq characterization pipeline. DNA from the diverse host/environment isolated, sheared into fragments and inserted between two randomized DNA barcodes. This pooled library of barcoded DNA fragments can then assayed in hosts. The read-out of each experiment is simple amplification of the barcode using next generation sequencing machines. The technology addresses the gene-function knowledge gap and elucidates the function of the living organisms.

In some embodiments, to generate the Dub-seq library, a broad-host-range replication vector (e.g., pBBR1 replication origin) system can be used to make it amenable to mobilize the library and assay in diverse microbes. Molecular biology techniques can be used to insert double barcode pairs (e.g., 20 nucleotide barcode pairs) juxtaposing a unique restriction site (PmlI enzyme) on the plasmid and generating a ~2 million member plasmid library in *E. coli* (FIG. 4). The barcode pair junction can then be deep sequenced using Barcode-Pair sequencing PCR (BPseq), and a list of unique barcode pairs can be generated. To maximize the chances of expressing heterologous DNA fragment in *E. coli*, the T7 promoter can be inserted upstream of a genome fragment insertion site. The dual barcoded plasmid library can be made ready for cloning genome fragments by digesting it with PmlI enzyme, which presents a unique site between both barcodes in some implementations. *E. coli* (BW25113) genomic DNA can be extracted, and sheared into 3 Kb fragment size, and the fragments cloned into the sequence-characterized restriction-digested dual barcoded backbone vector (referred to herein as a *E. coli* Dub-seq library). Based on the colony forming unit calculations, *E. coli* Dub-seq library can encompass about 40,000 members corresponding to about eight times coverage of *E. coli* genome in some implementations.

In the next step, the *E. coli* Dub-seq library can be characterized using a TnSeq-like sample preparation and deep sequencing protocol (referred to herein as Barcode-association—with genome fragment sequencing or BAGseq). The BAGseq step can be used to identify the cloned genome fragment and its pairings with neighboring dual barcodes. This step of associating the dual barcodes with each library of donor genomic fragments can be done, for example, once for each library and can be used as a reference table to derive connections between observed functional/fitness traits (using Barseq) with specific cloned genomic fragment As there are two barcodes for each Dub-seq library, two BAGseq sample preparation steps can be required. Briefly, this involves shearing of the plasmid library (the Dub-seq library), end repair, adaptor ligation, and PCR amplification of the junction between barcode and genomic insert using primers that are complementary to one of the barcode and adaptor, and deep sequencing of these samples. In some embodiments, after the data analysis to filter out redundant barcodes, about 30,000 unique barcode pairs associated with an *E. coli* genomic fragment can be identified in the *E. coli* Dub-seq library and can have the distribution of the insert size around 3 kb (FIG. 4). The library can have a number of genes completely covered and a number of partial genes covered. Overall, the *E. coli* Dub-seq library can have each nucleotide covered about a number of desirable times and can be sufficient for doing competitive growth assays.

Figure 5:
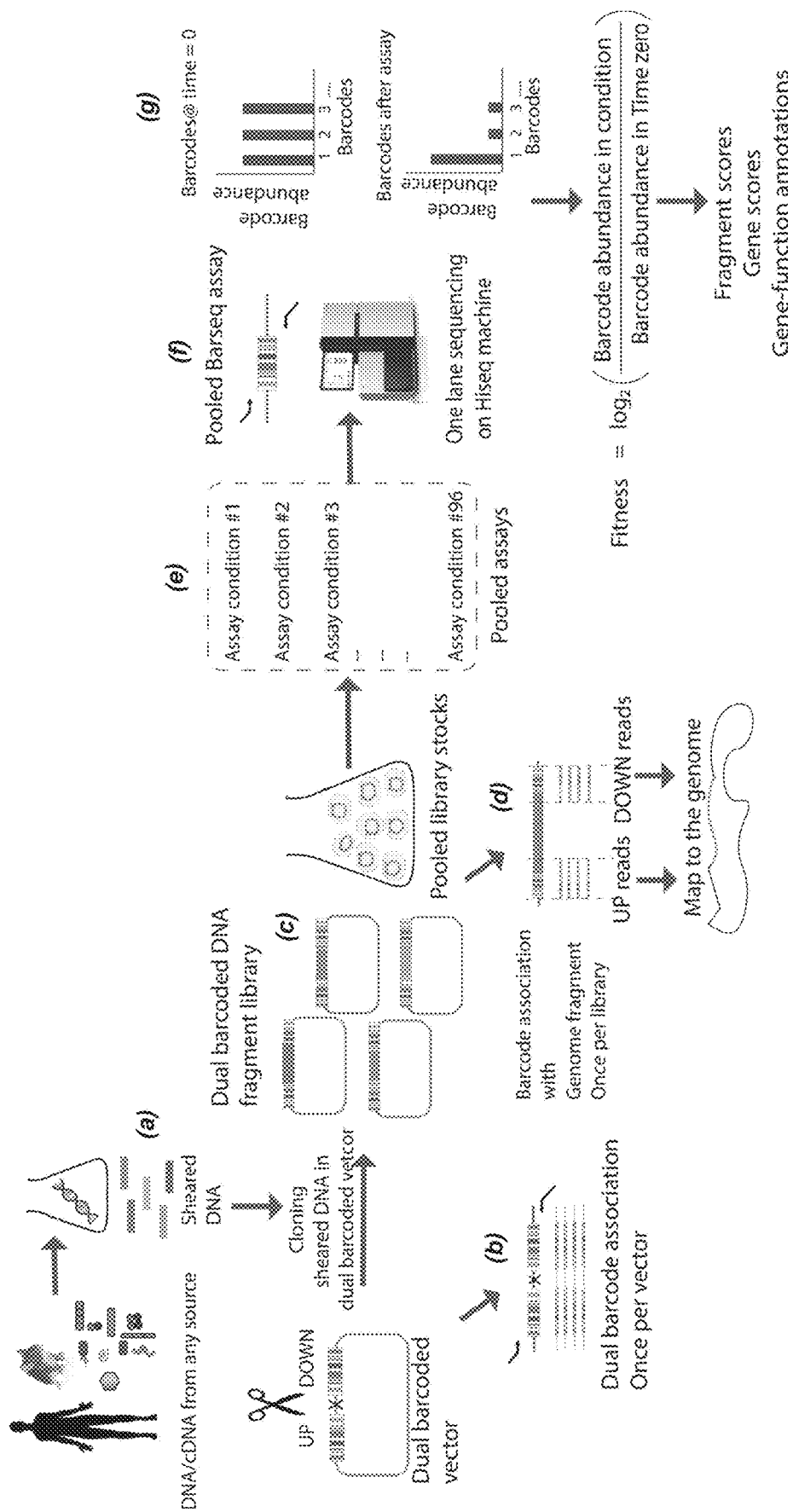
FIG. 5 is a non-limiting exemplary schematic overview of the Dub-seq technology. Dub-seq technology overview: panel (a) DNA (any source) sheared into fragments; panel (b) dual barcodes association; panel (c) Fragments inserted between two DNA barcodes; panel (d) barcode & fragment association; panel (e) library Assay in specific host; panel (f) one barcode amplification; and panel (g) Data analysis to count barcodes before and after the assay.
Figure 6:
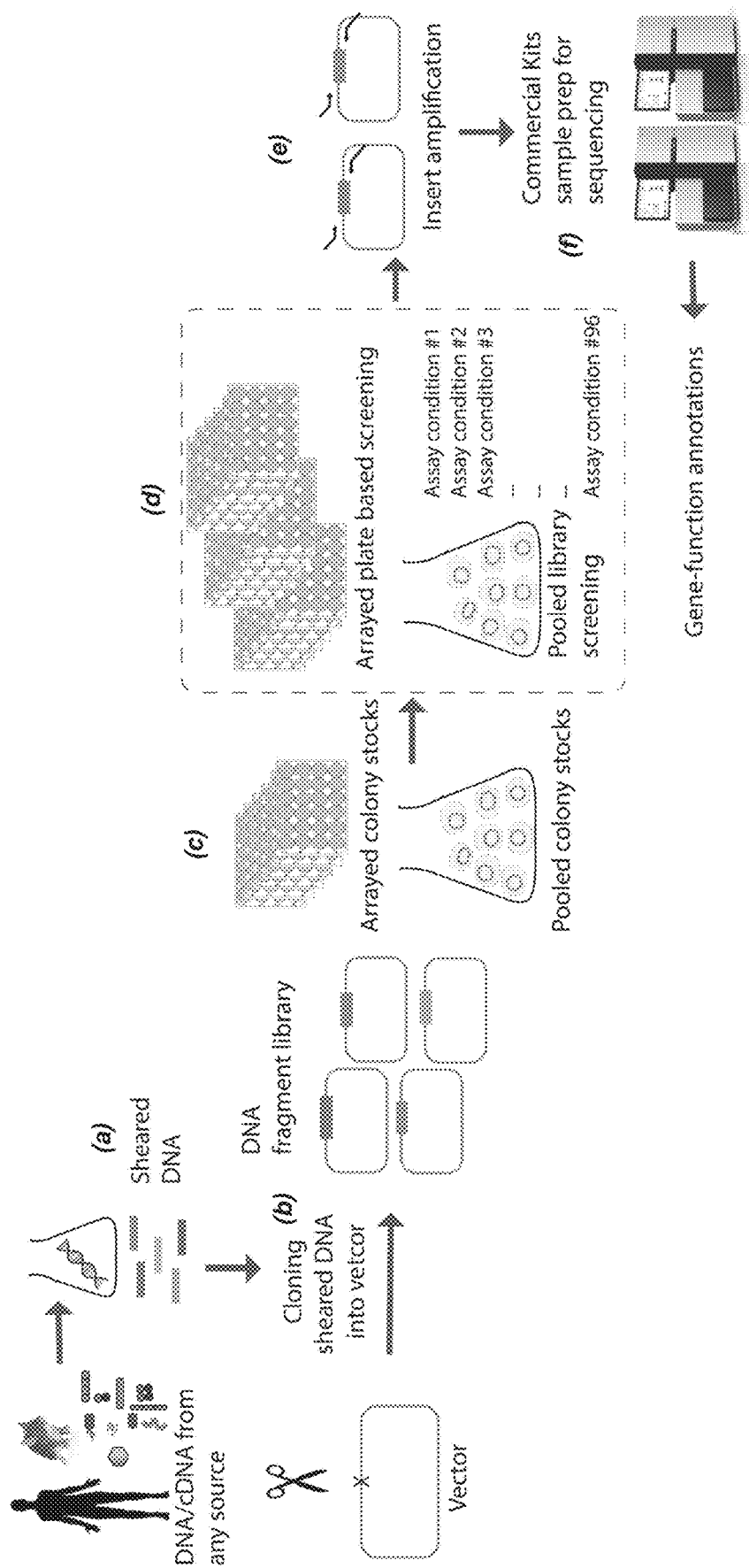
FIG. 6 is a non-limiting exemplary schematic overview of a shotgun sequencing method: panel (a) DNA sheared into fragments; panel (b) Fragments inserted on a plasmid; panel (c) pooled or arrayed library of clones; panel (d) Library Assay in specific host; panel (e) Sample prep through commercial kits; and panel (f) Samples run on sequencing machine and data analysis.

To identify cellular function encoded by the fragment (or the encoded gene), *E. coli* carrying the *E. coli* Dub-seq library (or an organism of another species carrying a Dub-seq library for the species, which can be species specific or non-species specific) can be subjected to competitive growth assays. Depending upon the assay condition and function encoded by the genomic fragment, the relative abundance of each strain changes due to its fitness phenotype. The relative abundance of a strain can then quantified via Barseq, in which one of the DNA barcodes is amplified and sequenced before and after each assay and determine the relative quantification of strains. To validate the entire methodology, competitive growth experiments can be performed using *E. coli* Dub-seq library at inhibitory concentration of a number of conditions, such as 5 conditions (metals: nickel, copper, cobalt, benzalkonium chloride, polymyxin B). After the growth experiment, the plasmid pool can be isolated, and Barseq PCR and sequencing on Miseq platform can be performed. From these initial pilot assays, the following can be confirmed in some embodiments: (1) the mapping of barcodes from BPseq and BAGseq methods to genome location can work well and yield a number of well known genes to their functions; (2) chimeric reads can contribute a minimal percentage; (3) data can be reproducible across biological replicates; and (4) and by performing Barseq PCR and sequencing of both barcodes, the correlation between relative abundance of up and down barcodes can be confirmed, thus enabling Barseq PCR of single barcode to quantify strain abundance (FIG. 5). In some embodiments, the top scoring candidates can be in agreement with or different from that in the reported literature or not reported in the literature. For example, top scoring genes rcnA, cysE and me are known to yield tolerance to high levels of nickel and cobalt; nlpE and CutC (with its encoded sRNA) for copper, benzalkonium chloride, and polymyxin B; proY in nickel; yfgG, yniD, mdtG, hslU for nickel, cobalt, and copper. micL represses 1pp (murein lipopetide). Top hits of copper tolerance are: mltD and EnvZ; and mltD may regulate 1pp. EnvZ is a kinase and can be pairing with copper two component response regulator. ybaP can be related to Nickel tolerance and encodes chiX sRNA.

In some embodiments, an advantage of the disclosed systems and methods is that only one time characterization of barcode junction with cloned genomic fragment via BAGseq step and subsequent use of single Barseq step to quantify strain abundance need to be performed. In contrast to other shotgun sequencing methods of the entire overexpression library after every fitness assay or sample time, the Barseq method can enable a simple, economical, less laborious workflow in a high-throughput, scalable assay format. For example, more than 100 competitive growth experiments can be performed using *E. coli* Dub-seq library across 52 stress conditions. The selections of gene functions can include metals, salts, aromatic carbon substrates in addition to different carbon and nitrogen sources, antibiotics, other toxic stresses, or any combination thereof.

Some embodiments disclosed herein provide methods of constructing an expression library from a plurality of nucleic acid fragments. In some embodiments, the plurality of nucleic acid fragments is from a single cell, a plurality of cells, a tissue sample, a virus, a fungus, or any combination thereof. The nucleic acid fragments can be DNA, such as genomic DNA, cDNA, and the likes; or RNA, such as mRNA, microRNA, tRNA, rRNA, and the like. In some embodiments, the plurality of nucleic acid fragments can be a plurality of genomic fragments. In some embodiments, the plurality of genomic fragments can comprise a completely or partially sequenced genome, a single cell genome, a viral genome, a bacterial genome, a metagenome, or any combination thereof. In some embodiments, the plurality of nucleic acid fragments is from a single cell, a plurality of cells, a tissue sample, a virus, a fungus, or any combination thereof. The nucleic acid fragments can have a variety of sizes. For example, the plurality of nucleic acid fragments can have an average size that is, is about, is less than, is greater than, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, or a range between any two of the above values. In some embodiments, the nucleic acid fragments can be obtained by a fragmenting treatment, including but not limited to enzymatic treatment such as restriction enzyme digestion, physical treatment such as sonication, etc.

In some embodiments, the methods comprise providing a plurality of vectors. In some embodiments, each vector comprises one or more barcodes. The plurality of vectors can comprise at least about 100, 1,000, 10,000, 100,000, 1,000,000, or more vectors. In some embodiments, each vector comprises two barcodes. The barcode, or the two barcodes, can be selected from a set of unique barcodes. The barcode or the two barcodes can be completely random in sequence which can be sequenced before (or after) nucleic acid fragment cloning. In some embodiments, the plurality of vectors can be characterized so that each vector is identified with a unique barcode or a unique combination of two or more barcodes. In some embodiments, the characterization of the vectors comprises sequencing at least a portion of the one or more barcodes. In some embodiments, the two barcodes in a vector are next to each other. In some embodiments, the two barcodes are separated by one or more restriction sites. In some embodiments, the two barcodes are separated by one or more selection marker genes.

A barcode can comprise a nucleic acid sequence that provides identifying information for the specific nucleic acid fragment associated with the barcode. A barcode can be at least about 1, 2, 3, 4, 5, 10, 15, 20, 25, 30, 35, 40, 45, 50, or more nucleotides in length. A barcode can be at most about 300, 200, 100, 90, 80, 70, 60, 50, 40, 30, 20, 15, 12, 10, 9, 8, 7, 6, 5, 4, or fewer nucleotides in length. In some embodiments, there may be as many as $10^6$ or more different barcodes in the set of unique barcodes. In some embodiments, there may be as many as $10^5$ or more different barcodes in the set of unique barcodes. In some embodiments, there can be as many as $10^4$ or more different barcodes in the set of unique barcodes. In some embodiments, there can be as many as $10^3$ or more different barcodes in the set of unique barcodes. In some embodiments, there can be as many as $10^2$ or more different barcodes in the set of unique barcodes.

In some embodiments, a barcode can be flanked by a pair of binding sites for two universal primers. The two universal primers can be the same or different. In some embodiments, each barcode of the plurality of vectors is flanked by the same pair of binding sites.

An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, a virus, a recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. The vector can be a variety of suitable replication units, including but not limited to: plasmids, viral vectors, cosmids, fosmids, and artificial chromosomes. In some embodiments, the vector is a broad-host-range replication vector. For example, there are a wide range of broad-host plasmids, cosmids and fosmids available based on IncQ, IncW, IncP, and pBBR1-based systems that can replicate in diverse microbes (Lale et al., (2011) Broad-host-range plasmid vectors for gene expression in bacteria. Strain engineering: Methods and protocols (Ed., James Williams), Methods in molecular biology, Vol 756, Chapter 19, 327-343).

In some embodiments, the vector can comprise a promoter sequence, such as a constitutive promoter, a synthetic promoter, an inducible promoter, an endogenous promoter, an exogenous promoter, or any combination thereof. In some embodiments, the vector can comprise a poly-A sequence. In some embodiments, the vector can comprise a translation termination sequence, and/or a transcription termination sequence. In some embodiments, the vector can further encode a tag sequence.

In some embodiments, the methods comprise inserting the plurality of nucleic acid fragments into the plurality of vectors to generate a plurality of expression vectors. In some embodiments, the plurality of nucleic acid fragments can be ligated with one or more adaptors before inserting into the vectors. In some embodiments, the one or more adaptors comprise one or more barcodes and/or one or more binding sites for a universal primer. A barcode alone, or two barcodes in combination, can be associated with the nucleic acid fragment that is inserted into the vector. For example, the nucleic acid fragment inserted into the vector can be flanked by the two barcodes.

Inserting the nucleic acid fragments can comprise ligation, such as blunt end ligation. In some embodiments, the vectors can be digested with a restriction enzyme to linearize the vectors. In some embodiments, the linearized vectors are blunt-ended before the ligation with the nucleic acid fragments.

In some embodiments, the methods comprise transforming the plurality of expression vectors into a host organism. A host organism can be selected from bacteria, yeast, fungi, insect cells, mammalian cells, plant cells, and any combination thereof. In some embodiments, the methods comprise growing the transformed host organism under a selection condition, so that only the host organisms transformed with the expression vector can survive. In some embodiments, the bacterial cells are or comprise Gram-negative cells, and in some embodiments, the bacterial cells are or comprise Gram-positive cells. Examples of bacterial cells of the invention include, without limitation, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus Enterococcus faecalis, Bacillus coagulans, Bacillus ceretus, Bacillus popillae, Synechocystis* strain PCC6803, *Bacillus liquefaciens, Pyrococcus abyssiSelenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes,* or *Streptomyces ghanaensis.*

Sequencing

The expression vectors comprising the nucleic acid fragments flanked by one or more barcodes can be subject to sequencing reactions to determine the nucleic acid fragment sequence or part thereof, the barcode sequence or part thereof, or both. In some embodiments, the expression vectors are sheared before sequencing. The sheared fragments can have an average size of, or of about, 100 bp, about 200 bp, about 300 bp, about 400 bp, about 500 bp, about 1,000 bp, or a range between two of any these values. In some embodiments, the sheared nucleic acid fragments are amplified using universal primers. In some embodiments, adaptors are added to the sheared nucleic acid fragments. In some embodiments, the adaptors comprise binding sites for sequencing primers, such as Illumina indexed primers for multiplex/parallel sequencing. In some embodiments, an adaptor can comprise a sample index, an experiment index, a cell index, or a combination thereof, to allow simultaneous sequencing of multiple samples, experiments, cells, or likes.

Any suitable sequencing method known in the art can be used, preferably high-throughput approaches. For example, cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing.

In some embodiments, the sequencing comprises paired end sequencing. In some embodiments, the sequencing comprises single end sequencing. In some embodiments, the sequencing comprises using a universal primer that binds to a binding site flanking a barcode. In some embodiments, the sequencing comprises using a primer that binds to a nucleic acid fragment in the expression vector.

In some embodiments, sequencing can comprise sequencing at least about 10, 20, 30, 40, 50, 60, 70, 80, 90, 100, 200, 300, 400, 500, 600, 700, 800, 900, 1,000, or more nucleotides or base pairs of the nucleic acid fragment sequence and/or barcode sequence. In some embodiments, sequencing can comprise sequencing at most about 10, 20, 30, 40, 50, 60, 70, 80, 90, 100, 200, 300, 400, 500, 600, 700, 800, 900, 1,000, or less nucleotides or base pairs of the nucleic acid fragment sequence and/or barcode sequence. In some embodiments, sequencing can comprise sequencing at least about 2,000, 3,000, 4,000, 5,000, 6,000, 7,000, 8,000, 9,000, 10,000 or more nucleotides or base pairs of the nucleic acid fragment sequence and/or barcode sequence. In some embodiments, sequencing can comprise sequencing at most about 2,000, 3,000, 4,000, 5,000, 6,000, 7,000, 8,000, 9,000, 10,000, or less nucleotides or base pairs of the nucleic acid fragment sequence and/or barcode sequence.

In some embodiments, sequencing can comprise at least about 200, 300, 400, 500, 600, 700, 800, 900, 1,000 or more sequencing reads per run. In some embodiments, sequencing can comprise at most about 200, 300, 400, 500, 600, 700, 800, 900, 1,000 or more sequencing reads per run. In some embodiments, sequencing comprises sequencing at least about 1,500; 2,000; 3,000; 4,000; 5,000; 6,000; 7,000; 8,000; 9,000; or 10,000 or more sequencing reads per run. In some embodiments, sequencing comprises sequencing at most about 1,500; 2,000; 3,000; 4,000; 5,000; 6,000; 7,000; 8,000; 9,000; or 10,000 or more sequencing reads per run. In some embodiments, sequencing can comprise sequencing at least 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at most 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at least 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise sequencing at most 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise less than or equal to about 1,600,000,000 sequencing reads per run. In some embodiments, sequencing can comprise less than or equal to about 200,000,000 reads per run.

In some embodiments, the methods further comprise associating the sequence of the first barcode or the sequence of the second barcode with the sequence of the nucleic acid fragment. In some embodiments, the methods for associating the sequences of the barcodes and the nucleic acid fragments can be the same as described in Opijnen et al., Tn-seq: high-throughput parallel sequencing for fitness and genetic interaction studies in microorganisms, Nature Methods 6:767-772 (2009), the content of which is hereby expressly incorporated by reference in its entirety.

Barcoded Expression Libraries

Some embodiments disclosed herein provide barcoded expression libraries comprising a plurality of expression vectors, wherein each expression vector comprises a nucleic acid fragment flanked by a first barcode and a second barcode. The barcoded expression libraries can be generated using the methods disclosed herein.

In some embodiments, the plurality of nucleic acid fragments is from a single cell, a plurality of cells, a tissue sample, a virus, a fungus, or any combination thereof. The nucleic acid fragments can be DNA, such as genomic DNA, cDNA, etc., or RNA, such as mRNA, microRNA, tRNA, rRNA, and the like. In some embodiments, the plurality of nucleic acid fragments can be a plurality of genomic fragments. In some embodiments, the plurality of genomic fragments can comprise a sequenced genome, a single cell genome, a viral genome, a bacterial genome, a metagenome, or any combination thereof. In some embodiments, the plurality of nucleic acid fragments is from a single cell, a plurality of cells, a tissue sample, a virus, a fungus, or any combination thereof. The nucleic acid fragments can have a variety of sizes. For example, the plurality of nucleic acid fragments can have an average size that is, is about, is less than, is greater than, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, or a range between any two of the above values. In some embodiments, the nucleic acid fragments can be obtained by a fragmenting treatment, e.g., enzymatic treatment such as restriction enzyme digestion, physical treatment such as sonication, etc.

In some embodiments, the plurality of nucleic acid fragments comprises at least 10%, at least 20%, at least 30%, at least 40%, at least 50%, at least 60%, at least 80%, at least 90%, at least 95%, at least 99%, coding sequences for single proteins and small operons of a donor organism. In some embodiments, the plurality of nucleic acid fragments comprises at least 1 fold genomic coverage, 2 fold genomic coverage, 3 fold genomic coverage, 4 fold genomic coverage, 5 fold genomic coverage, 6 fold genomic coverage, 7 fold genomic coverage, 8 fold genomic coverage, 9 fold genomic coverage, 10 fold genomic coverage, 20 fold genomic coverage, 30 fold genomic coverage, 40 fold genomic coverage, 50 fold genomic coverage, 60 fold genomic coverage, 70 fold genomic coverage, 80 fold genomic coverage, 90 fold genomic coverage, 100 fold genomic coverage, or more, of the genome of the donor organism. In some embodiments, the donor organism is selected from bacteria, yeast, fungi, insect cells, mammalian cells, plant cells, and any combination thereof.

The barcoded expression libraries can comprise at least about 100, 1,000, 10,000, 100,000, 1,000,000, or more expression vectors. The first barcode and the second barcode of each expression vector can be generated randomly, or selected from a set of unique barcodes. In some embodiments, the plurality of expression vectors can be characterized so that each expression vector is identified with a unique combination of the first barcode and the second barcode. In some embodiments, the characterization of the vectors comprises sequencing at least a portion of the first barcode and the second barcode.

A barcode may comprise a nucleic acid sequence that provides identifying information for the specific nucleic acid fragment associated with the barcode. A barcode may be at least about 1, 2, 3, 4, 5, 10, 15, 20, 25, 30, 35, 40, 45, 50, or more nucleotides in length. A barcode may be at most about 300, 200, 100, 90, 80, 70, 60, 50, 40, 30, 20, 15, 12, 10, 9, 8, 7, 6, 5, 4, or fewer nucleotides in length. In some embodiments, there may be as many as $10^6$ or more different barcodes in the set of unique barcodes. In some embodiments, there may be as many as $10^5$ or more different barcodes in the set of unique barcodes. In some embodiments, there may be as many as $10^4$ or more different barcodes in the set of unique barcodes. In some embodiments, there may be as many as $10^3$ or more different barcodes in the set of unique barcodes. In some embodiments, there may be as many as $10^2$ or more different barcodes in the set of unique barcodes.

In some embodiments, a barcode can be flanked by a pair of binding sites for two universal primers. The two universal primers can be the same or different. In some embodiments, each barcode of the plurality of vectors is flanked by the same pair of binding sites.

An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, a virus, a recombinant virus or other vector that, upon introduction into an appropriate host cell, results in expression of the cloned DNA. Appropriate expression vectors are well known to those of skill in the art and include those that are replicable in eucaryotic cells and/or prokaryotic cells and those that remain episomal or those which integrate into the host cell genome. The vector can be a variety of suitable replication units, including but not limited to: plasmids, viral vectors, cosmids, fosmids, and artificial chromosomes. In some embodiments, the vector is a broad-host-range replication vector. For example, there are a wide range of broad-host plasmids, cosmids and fosmids available based on IncQ, IncW, IncP, and pBBR1-based systems that can replicate in diverse microbes (Lale et al., (2011) Broad-host-range plasmid vectors for gene expression in bacteria. Strain engineering: Methods and protocols (Ed., James Williams), Methods in molecular biology, Vol 756, Chapter 19, 327-343).

In some embodiments, the vector may comprise a promoter sequence, such as a constitutive promoter, a synthetic promoter, an inducible promoter, an endogenous promoter, an exogenous promoter, or any combination thereof. In some embodiments, the vector may comprise a poly-A sequence. In some embodiments, the vector may comprise a translation termination sequence. In some embodiments, the vector may further encode a tag sequence.

In some embodiments, the barcoded expression libraries are transformed into a host organism. A host organism can be selected from bacteria, yeast, fungi, insect cells, mammalian cells, plant cells, and any combination thereof. In some embodiments, the methods comprise growing the transformed host organism under a selection condition, so that only the host organisms transformed with the expression vector can survive. In some embodiments, the bacterial cells are Gram-negative cells, and in some embodiments, the bacterial cells are Gram-positive cells. Examples of bacterial cells of the invention include, without limitation, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus Enterococcus faecalis, Bacillus coagulans, Bacillus ceretus, Bacillus popillae, Synechocystis* strain PCC6803, *Bacillus liquefaciens, Pyrococcus abyssiSelenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes,* or *Streptomyces ghanaenis.*

Methods of Conducting Functional Analysis

Some embodiments disclosed herein provide methods of conducting functional analysis using the barcoded expression libraries disclosed herein. In some embodiments, the methods comprise transforming a test organism with a barcoded expression library comprising a plurality of expression vectors, wherein each expression vector comprises a nucleic acid fragment flanked by a first barcode and a second barcode. A test organism can be selected from bacteria, yeast, fungi, insect cells, mammalian cells, plant cells, and any combination thereof. In some embodiments, the bacterial cells are Gram-negative cells, and in some embodiments, the bacterial cells are Gram-positive cells. Examples of bacterial cells of the invention include, without limitation, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus Enterococcus faecalis, Bacillus coagulans, Bacillus ceretus, Bacillus popillae, Synechocystis* strain PCC6803, *Bacillus liquefaciens, Pyrococcus abyssiSelenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes,* or *Streptomyces ghanaenis.*

In some embodiments, the methods comprise subjecting the transformed test organism to a stress condition and collecting the expression vectors from the test organism subjected to the stress condition. In some embodiments, the stress condition comprises metal tolerance/resistance, diverse aromatic carbon tolerance/utilization, diverse carbon, and nitrogen sources, antibiotics, virus, phage, toxic stress, nutrients, physical condition such as temperature, pH, salt, UV light, light, supernatant of cell culture, plant extract, soil, water, any other environment or any combination thereof. The transformed test organism can be exposed to a stress condition in a variety of environments, such as cell culture, organs of a living animal, e.g., skin, blood vessels, stomach, intestines, etc.

In some embodiments, the methods comprise identifying a nucleic acid fragment that is resistant to the stress condition. Identification of the nucleic acid fragment that is resistant to the stress condition can comprise quantitative analysis of unique barcodes from the collected expression vectors and/or the unique barcodes from the barcoded expression library being transformed into the test organism. In some embodiments, quantitative analysis of unique barcodes from the collected expression vectors comprises sequencing the at least a portion of the first barcode, the second barcode, and/or the nucleic acid fragment from the collected expression vectors. In some embodiments, quantitative analysis of unique barcodes from the barcoded expression library being transformed into the test organism comprises sequencing the at least a portion of the first barcode, the second barcode, and/or the nucleic acid fragment from the barcoded expression library being transformed into the test organism. In some embodiments, identification of the nucleic acid fragment that is resistant to the stress condition comprises comparing the unique barcodes from the collected expression vectors with the unique barcodes from the barcoded expression library being transformed into the test organism.

In some embodiments, the sequencing comprises paired end sequencing. In some embodiments, the sequencing comprises single end sequencing. In some embodiments, the sequencing comprises using a universal primer that binds to a binding site flanking a barcode. In some embodiments, the sequencing comprises using a primer that binds to a nucleic acid fragment in the expression vector.

EXAMPLES

Some aspects of the embodiments discussed above are disclosed in further detail in the following examples, which are not in any way intended to limit the scope of the present disclosure.

Example 1

Generating and Characterizing a Dual Barcoded Library

In this example, clone expression libraries in E. coli are constructed and characterized for their functional traits in E. coli. The pBBR1 broad-host plasmid is used as it is relatively small, mobilizable and has been widely used for a variety of genetic engineering applications in diverse microbes. To insert the dual random barcodes downstream of T7 promoter on the broad host vector, standard molecular biology methods (Current protocols in Molecular Biology, DOI: 10.1002/0471142727, Online ISBN: 9780471142720; the content of which is incorporated by reference in its entirety) are used and millions of barcode pairs are generated in E. coli. By deep sequencing the barcode library, unique barcode pairs are characterized and used as a reference when associating barcodes with genome fragment junctions (i.e., the identity of the barcode pair enables one to map the exact breakpoints and length of each cloned genomic fragment in the library).

Example 2

Build the Characterization Pipeline to Identify Cloned Genome Fragments and their Association with Random Barcode Pairs Genomic DNA from E. coli is used to generate a 3 Kb Dub-seq library and expressed in E. coli under different media conditions. First, the Dub-seq libraries are cloned in E. coli and then library preparation is performed similar to the RB-TnSeq approach (Wetmore et al (2015) Rapid quantification of mutant fitness in diverse bacteria by sequencing randomly barcoded transposons (RB-TnSeq). mBio 6(3): e00306-15, the content of which is hereby expressly incorporated by reference in its entirety) is used to identify the cloned genome fragment and its pairings with neighboring dual barcodes. This step of associating the dual barcodes with each library of donor genomic fragments is done only once (by deep sequencing) and used as a reference table to derive connections between observed functional/fitness traits with specific cloned genomic fragment. The step of characterizing an overexpression library is only performed one time whereas the downstream analysis of fitness in a pooled assay can be performed many times using BarSeq. As the average gene length in bacteria is about 1100 bps, the initial Dub-seq library will encompass most single protein coding genes and small operons.

Dub-seq libraries can be used for sequencing organisms. In these applications, the Nextera library kit is used to sequence the shotgun library of the donor genome and assemble it using barcodes as reference terminals. The Dub-seq library preparation is used to insert large size donor genome fragments (~30-40 kb) for capturing DNA fragments coding for larger molecules, such as antibiotics and other secondary metabolites.

Example 3

Pooled Fitness Assays in Diverse Hosts to Study the Gain-of-Function Using BarSeq Methodology Once the Dub-seq library is built and characterized in E. coli, the entire library is transformed into the E. coli conjugation donor strain WM3064 and the library can be transferred into different hosts by conjugation (Wetmore et al (2015) Rapid quantification of mutant fitness in diverse bacteria by sequencing randomly barcoded transposons (RB-TnSeq). mBio 6(3):e00306-15). The library can have a multifold coverage of the entire donor genome (about 50 fold genome coverage). Massive selections of gene functions of relevance to environmental context can be performed, including metal tolerance/resistance, nitrate/nitrite reduction, and utilization/tolerance to aromatic carbon substrates in addition to different carbon and nitrogen sources, antibiotics, and other toxic stresses. The cellular fitness phenotype conferred by heterologous DNA will be quantified by the BarSeq protocol. A computational analysis algorithm can be used for counting barcodes, linking donor genome fragments to the barcodes, and calculating the quantitative fitness measures.

Example 4

Scaling Up Production of a pFAB5526 Library

This example describes scaling up production of a pFAB5526 (Seq ID No. 49) library for the Dub-seq protocol.

Thaw one glycerol stock of sFAB5870-Lib and inoculate 250 ml of LB+Kan, grow over night; pellet 50 ml cultures, store pellets at −20 C, and use one for making midiprep.

Midiprep

Notes: In any step during miniprep, avoid excessive shacking/vertex/pipetting, especially after P2 and N3 buffer addition as that will get the genomic contamination of plasmid prep.

50 ml pellet is treated like 5*10 ml overnight cultures; Add P1, Vertex, Add P2 to mix lightly, Add N3, mix lightly-quickly in 50 ml falcon tube having pellet. Once ppt is formed, pour ~1.8 ml in 2 ml appendroff tubes. Spin for 10 mins, and then pour the supernatant into ~8-9 columns on vacuum and follow rest of the protocol for minipreps.

Final elution is done using 10 Qiagen columns with 50 ul WATER. Total elution is ~500-600 ul (100-200 ng/ul conc). Water is used as enzyme PmlI is sensitive to salt (output of columns are heavy in salt. This problem can be overcome by keeping the plasmid volume less than 25% of total RD reaction).

Example 5

Barcode Pair Sequencing (BPseq) to Associate Up and Down Barcodes

This example describes BPseq for the Dub-seq Protocol.

Figure 7:
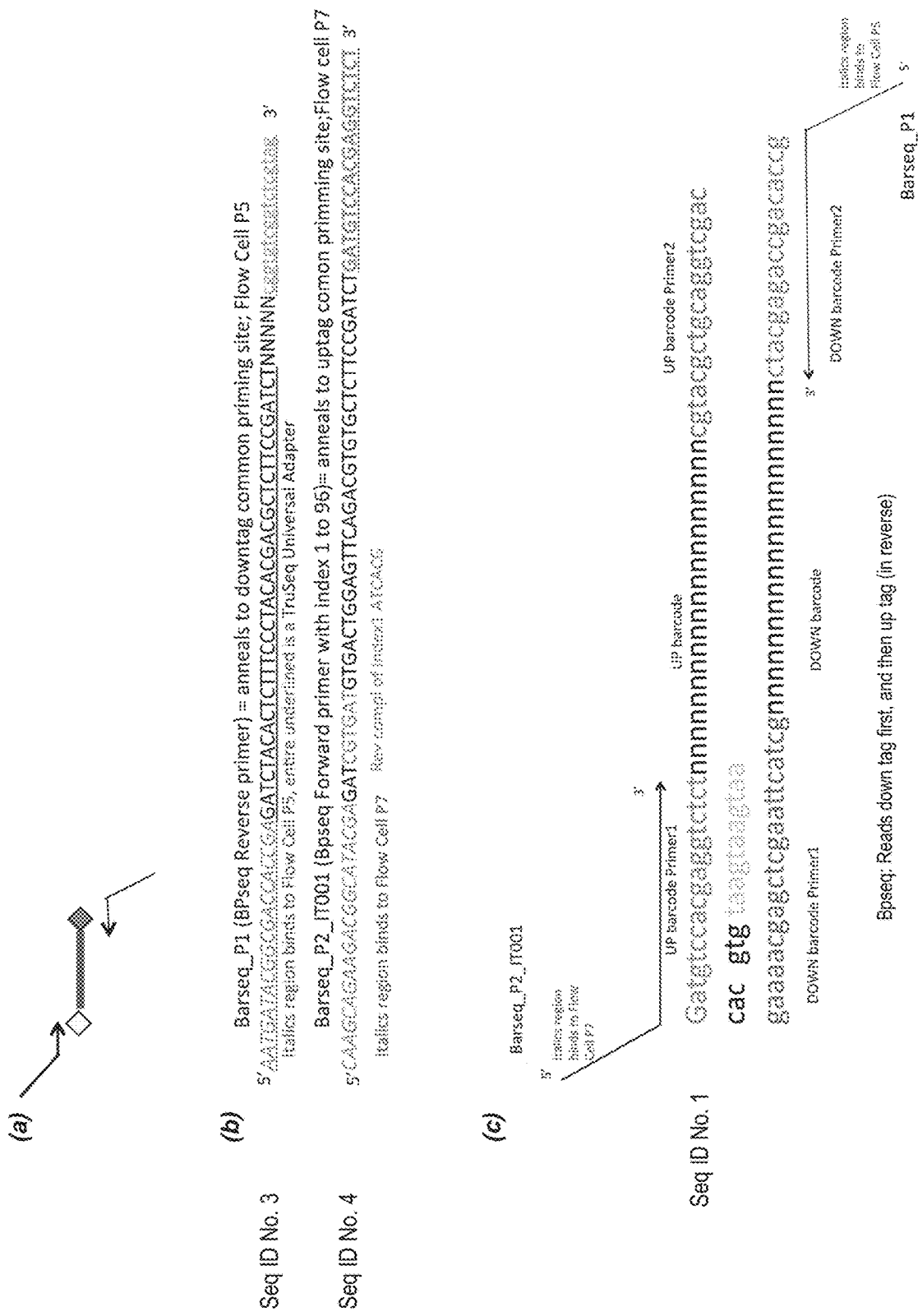
FIG. 7 panels (a)-(d) show barcode pair sequencing (BPseq) to associate Up and Down Barcodes.

FIG. 7 panels (a)-(d) show barcode pair sequencing (BPseq) to associate up and down Barcodes. Note that in Illumina's design, the P5 end is sequenced first, then the P7 region is sequenced (if a paired-end read), which cannot be changed. Sequencing for each read is unidirectional. Extension can only occur in the 5' to 3' direction. At the beginning of each read, each library fragment is attached to the flowcell by the 5' end with a free 3' end remaining. Thus, sequencing must occur "from the top, down."

BPSeq PCR to amplify both barcodes. P1 binds to the down tag universal primer binding region (Reverse). P2 binds to up tag (Forward) primer binding region. P2 is a primer with a total, for example, 96 indexes.

Choose the index based on other reactions being run at the same time.

Both Primers are 4 uM in concentration.
5 ul RV primer P1
5 ul FW Primer P2_IT001
38 ul of water sterile
2 ul template
50 ul of 2× Q5
Total 100 ul PCR Condition:
1. 98° C. 4 mins
2. 98° C. 30 Sec
3. 55° C. 30 Sec
4. 72° C. 30 Sec
5. Go to step 2, for 15 cycles
6. 72° C. 5 minutes
7. 10° C. infinite
   Run the analytical gel.
   If gel looks good, PCR purify, elute 50 ul with water/EB.
   Quantify by Nanodrop.
   Quantify by Qubit.
   150 SE MiSeq run set up:
   Excel sheet, cartridge, flow cell cleanup, sample sheet set up
   Follow MiSeq Protocol (if found satisfactory use HiSeq) Here both barcodes are sequenced and associated. Unique barcode pairs are counted and stored.

Example 6

Scale Up of Restriction Digestion of pFAB5526

This example describes scaling up restriction digestion of pFAB5526 for the Dub-seq protocol.

First Digestion (RD1)
Plasmid pFAB5526 concentration 100 ng/ul (total 500 ul elution from 50 ml pellet prep).
pFAB5526=900 ul (total 100 ug)
PmlI (NEB)=100 ul (this enzyme is sensitive to salt, so limit plasmid volume to less than 25% of total volume, as column purification yields salts)
10× cutsmart=400 ul
Water=2600 ul
Total=4000 ul
Total=500 ul*8 E (1.5 ml) Tubes
Incubate at 37° C. on a heating block for >1 hr. After 30 minutes of incubation, cast a 1% agarose gel.

Analytical gel check with uncut vector control, "if all looks ok" (Cut vector vs. Uncut vector shows nice distinction of complete digestion, with size 5.1 KB band for cut vector pFAB5526), pool RD1 sample into 15 ml Falcon tube.

Then proceed to dephosphorylation step using rSAP enzyme. This enzyme can be better than CIP or AP.

Reaction:
Add 1 unit of rSAP for every 1 pmol of DNA ends (about 1 μg of a 3 kb plasmid). For example, add 100 ul of rSAP to 4000 ul digestion reaction (above, or add 1 ul per 50 ul reaction);
Dispense 200 ul in PCR strip of 8 tubes, and then dispense 50 ul in each well of PCR plate. ~96 wells 50 ul RD1;
incubate at 37° C. for 2 hours in PCR machine.
Stop reaction by heat-inactivation of rSAP and restriction enzyme by 70 C for 20 minutes.
Meanwhile Cast a real BIG gel for gel purification (gel purify 96*50 ul samples).
Also check water bath temp to 50 or 55° C.
Pool all samples in a trough (or add 8 ul dye to each of 50 ul reaction), add 6×Dye, mix and load on the gel. Multichannel can use be used to load the samples. Once gel run is completed, use non-UV Transilluminator (no UV) to cut the entire stretch of gel. Put that in 50 ml falcon tube. The above results in 4*50 ml tubes each with ~4 gm of gel slice.

Use Qiagen Gel purify kit and protocol. Use water bath @55° C. to melt the gel. Elute the reaction in 6 columns with 60 ul of Water (so, total of 360 ul of cut vector). Final concentration is about more than ~25 ng/ul.
Second Digestion (RD2)
gel pure RD1 cut vector (about 9 ug)=360 ul
PmlI=10 ul
10×cut smart=200 ul sterile Water=1430 ul
Total=2000 ul
Note: total plasmid volume kept less than 25% of total volume of reaction.

500 ul*4 appendroff tubes
37° C. for 1 hr on heating block; Pool all in one tube.
To dephosphorylate, add rSAP 5 ul/tube or 20 ul to the pool.
Dispense 200 ul in PCR strip, and then dispense 50 ul in additional PCR tubes.
37° C. 2 hrs on PCR machine.
70° C. for 20 mins.

Cast a big 1% agarose gel, add 8 ul of 6× dye to each tube, mix, and load to run.
Gel purify the above reaction.
Note: Incubate the column with PE for few minutes as this will help in blunt end ligation later, see Qiagen notes.
Also additional Isopropanol is optional, as is not needed for gel purification of 1 to 4 kb fragments).
Elute through 2 tubes of 50 ul with water. Conc is about 25-35 ng/ul. This is the final cut vector used for cloning.

Example 7

Handling Different Microorganisms

This example describes handling different microorganisms for the Dub-seq protocol.
Follow FEBA protocols to handle different microbes:
Prepare media plates and liquid media. Check conditions, Streak culture/stock on plate and also start the liquid culture.
Pick a colony to make a stock and also do 16S Sequence determination.
16S RNA PCR and Sequencing Protocol Add 50 ul of Instagen (shake instagen bottle well) and small scraping of colonies in PCR tube.

Biorad program: 56° C., 5:00; 100° C., 8:00; 4° C., infinite.
Spin down PCR tube(s).
New PCR tube add following reagents per reaction:
Mastermix=10 ul
Primer=5 ul
DNA=1 ul
H2O=4 ul
Flick and spin down.

Biorad program: 98° C., 0:30; 98° C., 0:10; 50° C., 0:30; 72° C., 1:30; Goto 2, 29x; 79° C., 10:00; 10° C., infinite.
16S rRNA 5'-3':

```
27f:
                                      (Seq ID No. 52)
AGA GTT TGA TCM TGG CTC AG

1492r:
                                      (Seq ID No. 53)
CGG TTA CCT TGT TAC GAC TT
```

Example 8

Genome Preparation and End Repairing

This example describes genome preparation and end repairing for the Dub-seq protocol.
Start overnight in particular media and make genome preps using Qiagen Blood & Tissue Kit. Usually, 1 ml of overnight or 2 ml of night culture can be used for genome prep. While planning to make genome prep make multiple pellets to process. Store additional 1 ml pellets at −20° C. for future preps. Final elution is about 200 ul and concentration is about 30-150 ng/ul.
S1 Nuclease Treatment (for SAG Samples Only)
1. Pool your SAG samples as needed.
2. Measure DNA volume and DNA concentration.
3. Calculate total DNA mass (in μg).
4. Mix DNA, 5× S1 Nuclease buffer, water and 0.1 ul 51 nuclease enzyme per μg (can use slightly more). Try to keep total volume <200 ul (this will help when shearing).
5. Flick to mix and quick-spin down.
6. Incubate at room temperature for 30 mins.
Genome Shearing The Covaris protocol can be used for genome shearing. Briefly,
1. Fill up the water tank till the mark, close the tank with shearing set up;
2. Start the chiller (check set pt 18° C.); Start Covaris, Degas pump will start automatically, Choose 3 Kb program; It will take 30 mins to degas.
3. 200 ul of sample volume and concentration can be between 2-20 ug. Use blue special tubes and adaptor for 3 kb fragments. Careful to not have bubbles and also as the bottom of the tube is hydrophobic, make sure to gently stir the sample with pipette tip until the sample cover the bottom completely. Also make sure there are no droplets on the interior of the tube.
4. Once degass is done, press run to start the program. Each genome takes 10 min to shear genomes to 3 kb.
5. Stop the pump (on computer); Empty the tank; start the pump to empty the coil; stop covaris and chiller.
6. Run a quick analytical gel to check the shearing. Cast a bigger gel for gel purification.
7. Gel purify first to reduce the volume for end repair. For 3 genome prep Shearing (3*200 ul =total 600 volume of shearing), gel fractions of 1.5 to 4 kB bands taken in to 15 ml falcon tubes. Check the water bath temp (50° C.). Use Qiagen gel extraction kit. Final elution for 3 sheared genome preps through 4 tubes=4*50 ul water=200 ul of ~45 ng/ul
End Repair with End-it Kit Follow Epicenter protocol (Print). Scale up as needed in separate tubes.
34 ul of Sheared DNA (45 ng/ul*34=1.5 ug total)
5 ul ATP
5 ul of dNTP mix
5 ul of EndIt buffer
1-2 ul of EndIT or endrepair enzyme (little bit more).
Total 50 ul reaction.
RT for 45 min, 70° C. for 10 mins;
PCR purify.
Final Elution in 50 ul water for each reaction and ~25 ng/ul concentration recovery.

Example 9

Set Up Ligation Between End Repaired 3 Kb Genome Fragment and PmlI Cut Vector

This example describes setting up ligation for the Dub-seq protocol.
Use 8:1 insert:vector ratio consistently.
Use the fast-link ligation kit.
Cut-pure Backbone concentration=20 ng/ul; average 5.1 kb

TABLE 1

Example use of ligation calculator.

| | Digested Products | ng/ul | Length | nM |
|---|---|---|---|---|
| *Dinoroseobacter shibae* | Dino 3 kb | 37.0 | 3000 | 20.32 |
| | pFAB5526 Pmll | 11.6 | 5150 | 3.71 |

| | Target pmol | Vol for Target |
|---|---|---|
| Insert | 0.112 | 5.5 |
| pFAB5526 Pmll | 0.014 | 3.77 |
| Ligation Setup | ul | |
| Water | 9.94 | |
| 10X Fast-Link Buffer | 3.00 | |
| ATP | 1.50 | |
| Digested Insert | 5.51 | |
| Digesteed Vector | 3.77 | |
| Fast-Link Ligase | 4.00 | |
| Total Reaction Volume | 30 | |
| Incubation Time | O/N | |
| Incubation Temperature | 16° C. | |

Set up ligation overnight (18 hrs) at 16° C., inactivate 75° C. for 15 mins, PCR purify using Qiagen kit, Elute in single column with 100 ul water. Concentration of elute is 3-5 ng/ul (total 300-500 ng).

Scaling Up Transformation and Making Stocks

NOTE: Always keep concentration of ligation reaction less than 10 ng per transformation in 50 ul cells; that is volume less than 2 ul per 50 ul cells.

NOTE: Need Chloramphenicol 34 ug/ml plates (Large and smaller ones); Electroporation cuvettes, DH10B cells, SOC medium, Sterile Beads.

Take 1 ul of ligation reaction and mix with 50 ul NEB DH10B cells on ice. No bubbles, pipetting.

Time constant should be between 4-4.6 for NEB DH10B electroporation parameters.

Test transform before big transformation: calculate the plating efficiency etc. which can be scaled perfectly later.

Colony PCR may not be effective due to different GC % for all inserts. So it can be better to start overnight with individual colonies, make plasmid prep and sequence with soFAB64 (FW) and soFAB61 (RV).

Mix ~50-60 ul of column purified ligation reaction with 1500 ul (100 ul*15 tubes) of NEB DH10B electrocomp cells (Chilled tips, cuvettes, tubes), dispense 50-60 ul per cuevette. So have a total of 10 cuvettes. Eloctroporate with NED DH10B parameters (Tc about 3-4.5). Immediately add 1 ml SOC recovery media.

Pool all recoveries (10 ml total); Add 10 ml fresh SOC. Shake tubes @ 37° C. about 1 to 1.30 hr. Spin down 5000 rpm 3 min; Slowly, resuspend the pellet in 5-6 ml. Based on test transformations the efficiency of transformation can be determined. Plate different volumes of 6 ml of total transformant on big plates. For example, plate 500 ul, 750 ul, 1 ml, 1.250 ml and 1.5 ml. on Nicely dry 37° C. incubated big plates o LB+Cam (Check the media and stocks well in advance). Incubate 37° C. for overnight.

Along with this, dilute the resuspended pellet in 10^2 (10 ul+990 ul), 10^3 (10+990 ul), 10^6 (10+990) and plate 100 ul on small plates. Next day count and calculate the colony forming units (CFU).

For *E. coli* library, have 15 colonies on 10^4 dilution small plates. That is 10^-4*10^-1=10^5 dilution. This yields 15*10^5=1.5 million CFUs.

Calculate the number of colonies needed from the epicenter manual for 99% coverage of genome. N=ln(1-0.99)/ln(1-(Insert size/GenomeSize)).

For *E. coli* genome (4.7 mb) and 3 Kb fragment, need about 4610 colonies (ln(1-0.99)/ln(1-(3000/4700,000)) for 99% coverage probability (gives 4610 Colonies for round numbers). If CFUs were about 1.5 million, then the coverage is about 325-fold.

Calculate CFU from dilution plates and also estimate from Big plates. Collect 8-10 times than needed CFUs (say 4K CFU needed for 99% coverage for 3 Kb, then collect about 40K cfus. Test these libs by counting barcodes by Barseq and then proceed to BAGseq (TnSeq).

Scoop colonies (after estimating CFUs needed) using spatula in 20 ml LB-CamR., Vertexed, mixed, in 250 ml media, add in few ml of culture to get the OD of 0.2 starting. Grow the culture at 37° C. till the final OD is 0.8-1 (~1.45 mins to 2 hrs). Prepare 30 ml glycerol stock (15 ml culture+ 15 ml 30% glycerol, and dispense 1 ml in tubes) and stored in 96 well-capped barcoded tubes. 4-5*45 ml culture pelleted and stored. Also store the scooped out colony stock with glycerol.

Each CFU stock gets its own sFAB number and its own pFAB number to avoid confusion.

Use one-two pellet to do Mini prep. Elute in 5 columns each with 50 ul so that the total is about 250 ul. Check concentration (~30 to 40 ng/ul). This is used for quick Barseq to choose the library and then for doing BAGseq (TnSeq) library preparation. This midiprep is used for doing the transformation into Putida, Bl21DE3° C.43 assay strains, and also into MW3064 *E. coli* for conjugations in diverse bacteria.

Library QC by Sanger sequencing: Pick 95 individual colonies from small plates in 1400 ul of LB+Cam and pipette out 1 ml into Barker hall 96 deep well plate. 1 ml and 400 ul cultures grown overnight. Next day, 400 ul culture can be mixed with 400 ul of 30% glycerol and stored in −80° C. 1 ml culture was taken to UC core for Plasmid prep and sequencing using soFAB61 and soFAB64 (for pFAB5526 derivatives).

Example 10

Quick Barseq on Different CFU Miniprep Stocks

This example describes quick barseq on different CFU miniprep stocks for the Dub-seq protocol.

Primers for Barseq: To PCR out only up tag (from up and down tags).

Forward primer Barseq_p2_ITXXX indexed 96 primers are aliquoted as 5 ul volume with 4 uM stocks in −80° C.

Reverse primer is BSP-RV, and is universal for all Barseq PCRs. So a good amount is needed.

TABLE 2

Reaction set up.

| REAGENTS | Volume ul 1X | MasterMix for 6 samples |
|---|---|---|
| FW Barseq_P2_ITXXX (4 uM) | 5 | Separate |
| BSP_RV (100 uM) | 0.2 | 1.2 |
| Template (150 ng) | X (impt ~150 ng) | Separate |
| 5X Q5 reaction buffer | 10 | 60 |
| 5X Q5 GC enhancer | 10 | 60 |
| dNTPs (10 mM) | 1 | 6 |
| Q5 Polymerase | 0.5 | 3 |
| Water | 18.5 − X | Separate |
| Total | 50 | Disp **/tube |

Here it is important to take equal ng of template, as different concentrations can bias number of barcodes amplified.

Reaction: Barseq98° C.
1. 98° C. 4 minutes
2. 98° C. 30 seconds
3. 55° C. 30 seconds
4. 72° C. 30 seconds
5. Go back to step2 for 25 cycles
6. 72° C. 5 minutes
7. 10° C. hold
Run the gel to check the band of 200 bp.
PCR purify to Elute 50 ul EB or water.
Quantify by Nanodrop.
Quantify by Qubit.
50 SE MiSeq run set up (Excel sheet can be used to calculate volume for equal concentration to mix and denature, thaw cartridge, flow cell cleanup, sample sheet set up).
Based on the reads and barcodes, one library can be chosen that is clean and nice for further assays.

Example 11

Qubit Quantification of DNA

This example describes qubit quantification of DNA for the Dub-seq protocol.
1. Nanodrop gDNA samples using appropriate elution buffer. Use whatever buffer was used to elute DNA (depends on what kit/method was used above). The nanodrop value should be very close to the Qubit if the gDNA prep is high quality and RNA-free.
2. Get Qubit 3.0, Qubit assay tubes, Qubit dsDNA HS(High Sensitivity) Buffer, and Standard 1 and 2
3. Qubit HS range (50-500 ng/mL). For a typical gDNA prep, you will want to have a 1:1000 total dilution factor. (To make the first dilution (1:10), take 2 ul of sample and add 18 ul of SIGMA water to labeled hydrophobic tubes. Vortex and quick spin)
4. Prepare working solution of Qubit buffer+Qubit dye (dilute dye 1:200 in HS buffer with 199 ul HS buffer+1 ul dye). You need ~200 ul per assay, so make enough working solution plus a little extra (for example, if you have 10 tubes which include 8 samples and 2 standards, make enough for 12).
5. Prepare two standards (1 and 2): 190 ul working solution+10 ul standard.
Vortex and Quick Spin
6. Prepare sample tubes (198 ul working solution+2 ul diluted gDNA). This is 1:100 dilution. So total dilution factor for the assay is 1:1000. Vortex and quick spin
7. Wait 2 minutes before reading samples.
8. Measure using Qubit 3.0 using the HS assay. Follow instructions on screen.
 a. dsDNA
 b. dsDNA High Sensitivity
 c. Read standards
 d. Insert standard 1 then push Read standard
 e. Insert standard 2 then push Read standard
 f. Push Run samples
 g. Have original sample volume at 2 ul and the Output sample units ng/ul
 h. Insert sample tube and press Read tube
 i. Catalog Qubit tube concentration which is in ng/mL 9. The concentration is the "assay concentration" at the bottom. Then use 1:1000 dilution factor to convert directly from ng/mL (Qubit reading) to ng/ul (actual concentration).

Example 12

Sequencing for Barcode-Association with-Genome Fragment (BAGseq)

This example describes BAGseq for the Dub-seq protocol.
The Barcode-Association with-Genome Fragment (BAGseq) is similar to the Tn Seq Protocol.
FIG. 8 panels (a)-(e) and FIG. 9 panels (a)-(c) show a non-limiting schematic illustration of Barcode-Association with-Genome Fragment (BAGseq) of the up tag and the down tag.
BAGSeq step can be done only once for each genome fragment library to connect the validated barcodes to inserted genome fragment. Because of the two barcodes, perform two BAGSeq sample preps for each fragment library. So for example, if 3 kb sheared *E. coli* genome is cloned in to pFAB5477 to yield pFAB5488 lib, then prepare 2 samples for miSeq and Hiseq runs.
As a backup, prepare total 3 or 4 samples. This is important, as BAGSeq is one way sample prep, if the protocol is not properly performed, then the plasmid prep of the library and all subsequent steps and protocols have to be repeated. So prepare extra BAGseq sample and store the extra samples without final PCRing. In case some undesired band of adaptor is seen in Bioanalyzer, the backup stock can be used for repeating the PCR.
Note: Read the TnSeq protocol carefully before starting. Check all the buffers, and reagents required are available.
Based on quick barseq, one of the library will be chosen for assays.

Example 13

BAGseq Library Preparation

This example describes BAGseq library preparation for the Dub-seq protocol.
1. Shearing and Double SPRI Cleanup
Turn on Covaris, add Milli-Q water to correct fill level (15 fill), turn on water chiller on floor, make sure bottom of screen says "connected to instrument," it will automatically start to degas. Takes about 30 minutes.
 1.1 Bring 1 ug of gDNA up to 130 ul volume with TE in a 1.5 ml tube.
 1.2 Transfer the gDNA to a clean, labeled Covaris AFA microtube using p200.
Avoid making bubbles/eject slowly.
 1.3 Shear the gDNA.
  a. Ensure the Covaris is chilled to 4° C. and is degassed.
  b. Place tube(s) in Covaris plate holder.
  c. Shear with conditions: called Standard Covaris 300 bp.
  d. After shearing, remove sample from AFA microtube but first do the following.
  e. Use wipe to clean off top of each tube. Avoid any cross contamination of your sheared samples. Get the decrimper from Kelly's desk to remove the tops of the AFA microtubes but before doing so, use a p200 to transfer as much sheared DNA into labeled 1.5 ml hydrophobic microcentrifuge tube as possible.

f. Use p20 to transfer the rest of the sheared DNA.

g. Check total volume and use TE to top it off at 130 ul (usually about or more than 125 ul).

1.4 Clean the sheared DNA with a double SPRI:

a. Get Ampure beads from refrigerator, make sure to mix well to ensure proper resuspension. Always pipet Ampure beads slowly and carefully. Volumes of the beads need to be precise.

b. Add 0.85× Ampure SPRI beads to 130 ul sample (110 ul beads). Vortex briefly to mix.

c. Incubate at room temperature for 5 minutes.

d. After quick spin, place on magnetic rack without lids until supernatant clears ~10 mins.

e. Keep supernatant. Transfer supernatant to a fresh, labeled microcentrifuge tube.

f. Add 72 ul of Ampure SPRI beads to the collected supernatant. Vortex briefly to mix.

g. Incubate at room temperature for 5 minutes.

h. After quick spin, place on magnetic rack without lids until supernatant clears.

i. Keep pellet from this point forward in protocol.

Remove/discard supernatant while leaving tubes on magnet.

j. While leaving tubes on magnet, wash bead pellet with 500 ul freshly made 80% ethanol (use SIGMA water, as well as the specially labeled "tn-seq" ethanol in the red box; 8 ml ethanol and 2 ml sigma water). Add EtOH gently to side of tube to avoid disturbing pellet.

k. Let sit for 30 secs, then pipet off supernatant and discard.

l. Repeat steps 1.4.j to 1.4.k for a total of two ethanol washes.

m. Quick spin samples, then put back on magnetic rack to remove leftover ethanol with p20.

n. Let tubes air dry on magnet until shiny, cracked, and there's no ethanol left (about 10 minutes); Do not over dry; DNA yields will decrease if pellet is over dried. Elute by resuspending beads in 21 ul SIGMA water directly onto beads while on the magnet, then take tube off magnet and pipet up and down to resuspend completely.

p. Place tubes back on magnet to collect eluate. (It may be useful to use a sterile pipette tip to sweep beads out of the eluate.) Transfer 20 ul eluate to clean labeled 1.5 ml tube.

q. Check total volume and use SIGMA water to top it off at 20 ul.

r. Take 1 ul of each sample into per set up tubes to use on Agilent DNA 1000 chip.

2. End Repair (Green)

2.1 Add 56 ul of SIGMA water to the 19 ul sample.

2.2 To the now 75 ul sample add:
10 ul Phosphorylation buffer
4 ul dNTPs
1.5 ul Klenow DNA Polymerase (large fragment)
5 ul T4 PNK
5 ul T4 DNA Polymerase
(75 ul sample+25.5 ul master mix).

2.3 Mix by quick flick and quick spin.

2.4 Incubate at room temperature for 30 minutes.

2.5 Clean up using a 1.4× Ampure SPRI (141 ul beads); follow the general procedure 1.4.g-1.4.n.

For rest of protocol, remember to discard supernatants and save the SPRI bead pellet.

2.6 Elute in 34 ul SIGMA water by directly ejecting water on to pellet while still on magnet, then remove tube from magnet and pipet up and down to resuspend completely. Recover 33 ul and place in clean microcentrifuge tube.

2.7 Check total volume and use SIGMA water to top it off at 33 ul

Two potential stopping points: Can stop here (step 2), or stop after A-tailing and ligating adapters (step 5).

3. A-Tailing (Yellow)

3.1 To the 33 ul sample recovered, add:
5 ul NEB2 buffer
10 ul dATP
3 ul Klenow fragment (exo-).
(33 ul sample+18 ul master mix)

3.2 Quick flick to mix and quick spin.

3.3 Incubate for 30 minutes on a 37° C. heat block.

3.4 Clean up using a 1.4× Ampure SPRI (71.5 ul beads); follow the general procedure 1.4.g-1.4.n.

3.5 Elute in 20.5 ul SIGMA water by directly ejecting water on to pellet while still on magnet, then remove tube from magnet and pipet up and down to resuspend completely. Recover 19.5 ul.

3.6 Check total volume and adjust with SIGMA water if necessary.

4. Prepare Adapters 4.1 Adapters Mod2_univ and Mod2_TS should be annealed before use in ligation reaction (see sequences in Appendix 1).

4.2 Resuspend primers in 1×STE buffer to concentration of 100 uM.

4.3 In a 0.2 ml PCR tube, combine the following per each sample:
5 ul 100 uM Mod2_univ
5 ul 100 uM Mod2_TS.

4.4 flick briefly, quick spin, and place tubes in thermocycler with the following program: 30 min at 37° C., ramp PCR machine at 0.5° C./sec to 97.5° C. hold at 97.5° C. for 155 sec, then drop temperature (~0.1°) C. per cycle for 775 cycles (i.e. decrease temperature from 97.5° C. by 0.1° C. every 5 sec; hold at 4° C.

4.5 Dilute annealed adapters to 15 uM with TE buffer pH 8. Tn-seq adapters 15 uM stored in −20° C.

5. Ligate Adapters (Red Tubes)

5.1 In a 1.5 ml microcentrifuge tube, mix together per sample:
19.5 ul template from step 3
0.5 ul annealed adapters from step 4.5
25 ul 2× ligation buffer from NEBNext kit
5 ul quick ligase
(50 ul TV; 19.5 ul sample+30.5 ul master mix)

5.2 Quick flick to mix and quick spin 5.3 Incubate at room temperature for 15 minutes (or longer)

5.4 Clean up using a 1.0× Ampure SPRI (50 ul beads); follow the general procedure 1.4.g-1.4.n 5.5 Elute with 36 ul SIGMA water by directly ejecting water on to pellet while still on magnet, then remove tube from magnet and pipet up and down to resuspend completely. Transfer 35 ul eluates to 0.2 ml PCR strip tubes.

5.6 Check total volume and use SIGMA water to top it off at 35 ul

Can stop here.

6. PCR Amplification (Selects for DNA Fragments Containing Insertion-Sites)

6.1 Per sample, create PCR master mix in a 1.5 ml microcentrifuge tube (total 2 tubes: one for UP tag and another for down tag):
50 ul of 2× of Q5 (has DMSO)
13.8 ul SIGMA water
0.6 ul 100 uM Tn-UPtag OR Tn-DNtag
=64.4 ul 6.2 Mix well and flash spin.

6.3 Add 64.4 ul of master mix to each 35 ul eluate.

6.4 Add 0.6 ul of each of the indexed P7 PCR primers (P7_MOD_TS_index1 to 16 primers stored at −20° C.) to each sample individually, using different indexed primer per sample. Mix gently and flash spin. Total volume=100 ul.

6.5 Amplify on a thermocycler
94° C. 2 min,
[94° C. 30 sec, annealing temperature 68° C. 20 sec, 72° C. 30 sec]×10 with −1° C./cycle,
[94° C. 30 sec, annealing temperature 65° C. 20 sec, 72° C. 30 sec]×15
72° C. 10 min, 4° C. hold (BAGseq PCR).

Can stop here.

7. PCR Clean-Up 7.1 Transfer amplicons to 1.5 m. tubes. Clean up PCR reaction using a 0.9× Ampure SPRI (90 ul beads). Follow the general procedure 1.4.g-1.4.n.

7.2 Elute with 26 ul of TE pH 8.0 by directly ejecting water on to pellet while still on magnet, then remove tube from magnet and pipet up and down to resuspend completely. Transfer out 25 ul eluate.

7.3 Run 1 ul of library on an Agilent DNA 1000 chip. If library looks good, quantify with Qubit (step 8).

7.4 If adapter dimer is visible, do an additional 0.85× Ampure SPRI on the sample. Adjust total volume to 100 ul with TE, then cleanup using SPRI (85 ul beads).

7.5 Bind to beads, wash 2× 80% EtOH, dry and elute with 26 ul TE, transfer out 25 ul.

7.6 Re-run sample on Agilent to confirm loss of adapter dimer. If OK, quantify (step 8).

Library should have a nice size distribution, peak around 250+/−50 bp. Compare FIG. 10 panel (a) with 10B panel (b)
Preparing Samples for MiSeq or HiSeq Sequencing 8. Qubit 8.1 Follow the instructions for the "DNA quantification using Qubit" example.

9. Thaw MiSeq Kit for BAGseq 9.1 Get MiSeq Reagent Kit v3 150 Cycles PE Box 1 of 2 in little white freezer that requires a key.

9.2 Remove wrapping, and put the Reagent Reservoir into the rectangular turquoise cooler.

9.3 Fill cooler to the Max Water Line with MiliQ water from the room next door. Let sit on desk for one hour to thaw.

10. Prepare Library Pool and Denaturation (Excel Sheet)

10.1 Get Clear 1.7 mL tube and label it ing/ul pool.

10.2 To equalize indexes, use the Excel doc to get value of 75 ng for each sample.

10.3 Pool libraries together with correct volumes to make equimolar concentration in the 75 ng and add water to the pool tube to make ing/ul stock.

10.4 Get another Clear 1.7 mL tube and label it 2 nM pool.

10.5 Add the correct amount of SIGMA water and ing/ul ng pool mix that was calculated on the Excel doc.

10.6 Get another Clear 1.7 mL tube and label it Denatured Pool and get timer ready.

10.7 To denature, add 10 ul 2 nM library and 10 ul of freshly made 0.2N NaOH in that order and start timer for exactly 5 minutes.

10.8 Flick and spin down.

10.9 Get Hybridization buffer and add 980 ul of it to the tube right when 5 minutes ends. Library is now 20 pM concentration.

10.10 Pipet up and down to mix and vortex.

11. Preparation of MiSeq Sample Sheet and Loading Machine 11.1 Get MiSeq v2 Reagent Kit Box 2 of 2.

11.2 Get out flow cell, put on gloves and use MilliQ water to wash it to get salt out of the crevices 11.3 Dry with a Premium Grade Optical Tissue/orange box to wipe off by dabbing gently. Make sure there is no lint on the glass, especially on the U and black part.

11.4 Go to Miseq and push Sequence and follow instructions on screen that goes like this.

11.5 Enter Illumina BaseSpace account.

11.6 Remove old flow cell by opening the little black box flap on the bottom left of the machine and pushing the white button. Add clean flow cell.

11.7 Poke hole in film of new reservoir, labeled Load Sample in orange, with a p1000 tip. Discard tip.

11.8 Get a p1000 set to 600 and with another tip, suck up denatured pool and put into the bottom of the hole.

11.9 Open old sample sheet, edit it with user and/or sample information, save as the barcode on the Illumina reservoir.

11.10 Take out old buffer, and add a new buffer.

11.11 Put the Illumina reservoir into reagent cartridge.

11.12 While its checking the flow cell, turn on milliQ water to clean the grey reservoir in each well.

11.13 Bring both containers back into MiSeq room and put them on left of machine to dry.

11.14 Push Start Run.

12. After MiSeq Run, Cleaning Up 12.1 Get the brown Tween 20 concentrate bottle.

12.2 Transfer 5 mL of that to a 50 mL falcon tube and add 45 mL of milliQ to make a 10% working solution. Mix well and label tube.

12.3 Add 25 mL of that Tween working solution into a 500 mL graduated cylinder and add 475 mL of miliQ water.

12.4 Transfer 6 mL to each well in the clean, dry, grey reservoir on the left of the machine.

12.5 Pour the rest of the solution into the cleaning bottle.

12.6 Push Start Wash button on MiSeq screen and follow the directions, which will include:

12.7 Take out used Reagent Reservoir that is put in for this run (that had sample libraries in it).

12.8 Put grey, washing reservoir with the 6 ml solution in each well into machine.

12.9 Remove Buffer Bottle from the machine and throw away into trash.

12.10 Leave flow cell in the machine.

Run the codes to check if all look good. Submit the samples for HiSeq. Fill up the form. Keep track of samples, datasets, dates, stocks and write down notes.

Example 14

Assays and Barseq

This example describes assays and Barseq for the Dubseq protocol.

Pool Exp. Protocol (For Stress Plate 1-6).

Grow cells till OD of 0.7+.

Collect time zero pellets (4-6 pellets).

Pick desired stress concentrations and get a 48 well plate plus 24 eppendorf tubes.

Fill each eppendorf tube with desired concentration of water+stress for total volume of 300 ul. (Compounds can be found in the walk in 4 degree)

Mix by pipetting up and down and transfer 140 ul to well A1 then 140 ul to A2 from the first eppendorf tube, repeat for rest of plate. Discard in waste bags.

Take OD of cells grown and calculate for a starting OD for 0.025.

Add cells to media (~30 mls per plate).

Pipette 560 ul of cells +media to every well in plate and cover with breathable seal. Final volume of each well is 700 ul.

Place in plate reader and let run overnight: File under Mark prescreens >pool exp >infinite 48 well plate.

Use infinite plate readers.

Break plate readers and save as ASC file. Collect pellets based on growth. Layout is very important.

Store pellets at −20° C.

Miniprep using 96 Qiavac system.

Quantify the Minipreps using QuantIT assay kit (see manual). Briefly,

For 96 samples: mix reagent and buffer such that 200 ul/well can be dispensed in clear bottom black plates, add 5 or 10 ul of miniprep; mix well using 200 ul pipette.

In separate wells add 10 ul of standards (ready to use solutions from the kit).

Use Tecan plate reader, follow QuantIT protocol.

From standard curve calculate miniprep concentration.

Normalize using excel sheet from Kelly and calculate how much water and DNA needed for 200 ng DNA in each well.

Prepare Water-plate and plasmid-plate csv files.

Use Biomek to mix water, DNA and primer (BarseqP2_ITindexes1-96, with Indexes from −80° C.).

Add master mix (will have water, dNTP, Q5, Primer BSP_RV): See Barseq protocol.

Primers for Barseq to PCR out the up tag from up and down tags (See FIG. 11 panels (a)-(c).

Fw primer Barseq_p2_ITXXX indexed 96 primers are aliquoted as 5 ul volume with 4 uM stocks in −80° C.

RV primer is BSP-RV, and is universal for all Barseq PCRs.

TABLE 3

Barseq reaction set up.

| REAGENTS | Volume ul 1X | MasterMix for 108 samples |
|---|---|---|
| FW Barseq_P2_ITXXX (4 uM) | 5 | Separate |
| BSP_RV (100 uM) | 0.2 | 21.6 |
| Template (150 ng) | X (impt ~150 ng) | Separate |
| 5X Q5 reaction buffer | 10 | 1080 |
| 5X Q5 GC enhancer | 10 | 1080 |
| dNTPs (10 mM) | 1 | 108 |
| Q5 Polymerase | 0.5 | 54 |
| Water | 23.3 − X | Separate |
| Total | 50 | Disp 21.7 ul/tube |

Here it is important to take equal ng of template, as different concentrations can bias number of barcodes amplified.

Reaction: Barseq98° C.

1. 98° C. 4 minutes
2. 98° C. 30 seconds
3. 55° C. 30 seconds
4. 72° C. 30 seconds
5. Go back to step2 for 25 cycles
6. 72° C. 5 minutes
7. 10° C. hold PCR (using Barseq98° C. protocol). Store at −20° C.

Spin down and Check samples on Big Gel (500 ml of 1% agarose+50 ul dye (10K× dilution).

Use 1 ml of water+400 ul of 50% glycerol: use this mix 7 ul/well in a plate and add 5 ul of PCR reaction. Load the ladder.

Load 10 ul to gel alternatively. Check the size of the band. Pool 10 ul from each well in a trough and then to app tube.

Use Zymo kit to clean up the pooled samples; and elute 50 ul.

Sequence it on one lane of Hiseq.

Example 15

Dub-Seq Protocols

This example demonstrates strains and growth conditions, construction of dual barcoded Dub-seq vector, BPseq to characterize dual barcoded Dub-seq vector, BPseq data analysis, Dub-seq vector preparation for cloning genomic fragments, construction of E. coli Dub-seq library, BAGseq for characterizing barcoded genomic fragment junctions, BAGseq data analysis, overcoming challenges of BPseq and BAGeq data processing, competitive growth experiments, Barseq, and Barseq data analysis and fragment score calculation.

Strains and Growths Conditions

*Escherichia coli* BW25113 was purchased from the *E. coli* Genetic Stock Center. All plasmid manipulations were performed using standard molecular biology techniques (Current protocols in Molecular Biology, DOI: 10.1002/0471142727, Online ISBN: 9780471142720; the content of which is incorporated by reference in its entirety). All enzymes used for plasmid manipulations were obtained from New England Biolabs (NEB) and oligonucleotides were received from Integrated DNA Technologies (IDT). *Escherichia coli* strain DH10B (NEB) was used for plasmid construction and assay purposes. All strains were grown in LB rich media supplemented with 30 μg/ml Chloramphenicol at 37° C., and shaking at 900 rpm.

Construction of Dual Barcoded Dub-Seq Vector

To construct a double barcoded vector, a derivative of pBBR1 replication origin broad-host plasmid was used as it is relatively small, mobilizable and has been widely used for a variety of genetic engineering applications in diverse microbes (Kovach, et al., Gene, 166, 1995, 175-176; the content of which is incorporated by reference herein in its entirety). Molecular biology techniques were used to insert double barcode pairs on the plasmid and expressed them in *E. coli* (Current protocols in Molecular Biology, DOI: 10.1002/0471142727, Online ISBN: 9780471142720; the content of which is incorporated by reference herein in its entirety). Specifically, phosphorylated oFAB2853 (5' gtaagtaagaaaacgagctcgaattcatcgnnnnnnnnnnnnnnnnnnnnnctacgagaccgacaccgaggatctccaggcatc aaataaaa 3', Seq ID No. 46) and oFAB2854 (5' ttacacgtggtcgacctgcagcgtacgnnnnnnnnnnnnnnnnnnnnnagagacctcgtggacatcattcaccaccctATAG TGAGTCGTATTATGA 3'; Seq ID No. 47; Eco72I enzyme site in bold) primers to amplify pBBR1 derivative plasmid, removed the plasmid backbone using DpnI enzyme (as per manufacturing instructions, NEB), and ligated the amplified and pure product using T4 ligase (as per manufacturing instructions, NEB). The ligated product (named pFAB5491, Seq ID No. 48) was then column purified using Qiagen PCR purification kit, transformed into DH10B electro-competent cells (as per manufacturing instructions, NEB) and transformants were selected on LB-agar plates supplemented with 30 ug/ml Chloramphenicol. Next day, ~2 million CFUs of transformants were estimated and Chloramphenicol resistant colonies were scraped together into 20 ml LB with 30 ug/ml Chloramphenicol. Diluted this culture library to an optical density at 600 nm ($OD_{600}$) of 0.2 in fresh LB medium supplemented with 30 ug/ml Chloramphenicol and grew the library to a final $OD_{600}$ of ~1.2. Glycerol was added to a final concentration of 15%, and made glycerol stocks of 1 ml and stored them at −80° C. Cell pellets were collected to make plasmid library midiprep for further characterization of the library (BPseq). A modified version of pFAB5491, with Kanamycin resistance marker, was created (named pFAB5526, Seq ID No. 49).

BPseq to Characterize Dual Barcoded Dub-Seq Vector

To associate both barcodes and characterize pFAB5491 library, Barcode-Pair sequencing PCR (BPseq) was performed. For deep coverage of the library, 10 different PCR reactions were performed using primers barseq_P1 (reverse primer, binds to the down tag universal primer binding region;

Seq ID No. 3

5'

*AATGATACGGCGACCACCGA*<u>GATCTACACTCTTTCCCTACACGACGCTCT</u>

<u>TCCGATCT</u>NNNNNcggtgtcggtctcgtag 3',;

Italics region binds to Flow Cell P5, entire underlined is a TruSeq Universal Adapter) and Barseq-P2 (binds to Uptag (FW) primer binding region index primer IT001 index to IT010 used; 5' CAAGCAGAAGACGGCAT-ACGAGATCGTGATGTGACTGGAGTTCA-GACGTGTGCTCT TCCGATCTGATGTC-CACGAGGTCTCT 3', Seq ID No. 4; Italics region binds to Flow Cell P7).

PCR reaction consisted of:
5 ul reverse primer barseq_P1 (4 uM)
5 ul forward Primer Barseq-P2_IT001 to IT010 (4 uM)
38 ul of sterile water
2 ul template pFAB5491
50 ul of 2× Q5 enzyme
Total 100 ul reaction
PCR condition:
1. 98° C. 4 mins
2. 98° C. 30 Sec
3. 55° C. 30 Sec
4. 72° C. 30 Sec
5. Go to step 2, for 15 cycles
6. 72° C. 5 minutes
7. 10° C. infinite Finally, the PCR product was run on to analytical gel to confirm the amplification. The PCR product was purified (Qiagen PCR purification kit), quantified the DNA product with a Qubit double-stranded DNA (dsDNA) HS (high sensitivity) assay kit (Invitrogen), and loaded onto Miseq for 150SE run.

BPseq Data Analysis

BPseq run data was analyzed using custom Python script. Each BPseq read was processed independently, and both up and down barcodes were extracted based on the sequences of the predefined primers. The only barcode pairs that have sequence quality >20 for each nucleotide in both up and down tags are accepted for further analysis. The extracted barcode pairs were grouped by the concatenated sequences of up and down barcodes to generate a non-redundant set of unique barcode pairs. As a result, a set of associated barcode pairs is produced $P_{ij}=[u_i, d_j, n_{ij}]$, where $u_i$—up barcode, $d_j$—down barcode, $n_{ij}$—a number of reads supporting the association between barcodes $u_i$ and $d_j$.

Dub-Seq Vector Preparation for Cloning Genomic Fragments

To prepare Dub-seq vector for cloning, 900 ul or about 100 ug of plasmid preparation was made (Qiagen plasmid miniprep kit), and two-step of digestion was performed using Eco72I (or PmlI) enzyme. Restriction digestion conditions are:
pFAB5526 library=900 ul (total 100 ug)
PmlI enzyme=100 ul
10× cutsmart=400 ul
Water=2600 ul
Total=4000 ul Incubate the reaction at 37° C. on a heating block for more than 1 hr, and then check the progress of reaction on an analytical 1% agarose gel. To dephosporylate the restriction digested vector, 1 unit of rSAP was added for every 1 pmol of DNA ends (about 1 μg of a 3 kb plasmid), and incubated at 37° C. for 2 hours in PCR machine. Stop the reaction by heat-inactivation of rSAP and restriction enzyme by 70° C. for 20 minutes. The cut and dephosphorylated Dub-seq vector were then gel purified (Qiagen gel extraction kit). To remove any uncut vector, the restriction digestion, dephosphorylation reaction and purification steps were repeated once. The final concentration of cut and pure Dub-seq vector used for cloning genome fragment was about 25-35 ng/ul.

Construction of *E. coli* Dub-Seq Library

To construct Dub-seq library of *E. coli* genomic fragments, *E. coli* BW25113 genomic DNA and 1 ug was fragmented by ultrasonication to an average size of 3000 bp with a Covaris S220 focused ultrasonicator. The sheared genomic DNA was then gel purified and end-repaired using End-IT kit (Epicenter, as per manufacturer instruction). The reaction and conditions for this step used were as below:
34 ul of Sheared DNA (1.5 ug total)
5 ul ATP 10 mM
5 ul of dNTP mix 10 mM
5 ul of EndIt buffer 10×
1-2 ul of EndIT enzyme
Total 50 ul reaction.

The reaction was incubated at room temperature for 45 min, and the enzyme inactivated by incubating the reaction at 70° C. for 10 mins. The end-repaired genome fragments were purified with PCR clean-up kit (Qiagen), and quantified on Nanodrop.

The end-repaired genomic fragments were then ligated to the sequence-characterized dual barcoded backbone vector (pFAB5491) at 8:1 insert:vector ratio using Fast-link Ligase enzyme (Epicenter, as per manufacturer instruction). Typical ligation reactions were as below:
4 ul of Restriction-digested pFAB5491
20 ul End-repaired DNA
3 ul ATP 10 mM
6 ul of 10× ligase buffer
19 ul of Water
8 ul of Fast-link-ligase
60 ul of Toal reaction Ligation was set up for overnight (18 hrs) incubation at 16° C., the ligase inactivated at 75° C. for 15 mins, and ligation products were purified using PCR purification kit (Qiagen).

For transforming the ligation reaction, 60 ul of column purified ligation reaction was mixed gently with 1500 ul (15 tubes of 100 ul competent cells) of NEB DH10B electrocompetent cells on ice and dispense 60 ul per cuvette. Electroporation was done using parameters supplied by NEB. Transformed cells were recovered by adding 1 ml SOC recovery media (as per competent cell manufacturer instruction, NEB). All recoveries (10 ml total) were pooled, and additional 10 ml of fresh SOC was added. Transformants were then incubated at 37° C., shaking for 90 minutes. The pellets were gently spun down, the pellet resuspended in 6 ml SOC. Different volumes of 6 ml resuspended pellets were then plated on overnight-dried big-square plates of LB agar supplemented with 30 ug/ml Chloramphenicol. Smaller dilution plates were made for estimating colony-forming units.

The number of colonies required for 99% coverage of *E. coli* genome was determined using the formula N=ln(1-0.99)/ln(1-(Insert size/GenomeSize)) to ensure that genome fragments were present in the cloned library (Sambrook, J. et al., (1989) in: Molecular Cloning: A Laboratory Manual (2nd ed.), CSH Laboratory Press, New York; the content of which is incorporated herein by reference in its entirely). For example, *E. coli* genome (4.7 Mb) of 3 Kb fragments, about 4610 colonies were needed for 99% coverage probability. (ln(1-0.99)/ln(1-(3000/4700,000))). 40,000 colonies were collected (about 10 times than needed CFUs for 99% coverage) by scraping the colonies using spatula in 20 ml LB media supplemented with 30 ug/ml Chloramphenicol in 50 ml Falcon tube and mixed well. This *E. coli* Dub-seq library was diluted to an optical density at 600 nm ($OD_{600}$) of 0.2 in fresh LB medium supplemented with 30 ug/ml Chloramphenicol and grown the library to a final $OD_{600}$ of −1.2 at 37° C., 900 rpm. Glycerol was added to a final concentration of 15%, and multiple glycerol stocks of 1 ml volume were made and stored them at −80 C. Cell pellets were stored at −80 C and to make large plasmid preparation (Qiagen) for further characterization. For example, a 250 ul miniprep (~40 ng/ul) was made and used for doing BAGseq library preparation. This midiprep is also used for doing the transformation into *E. coli* Bl21 DE3 C43 (NEB) assay strain and MW3064 *E. coli* for conjugating the library into diverse bacteria.

Figure 12:
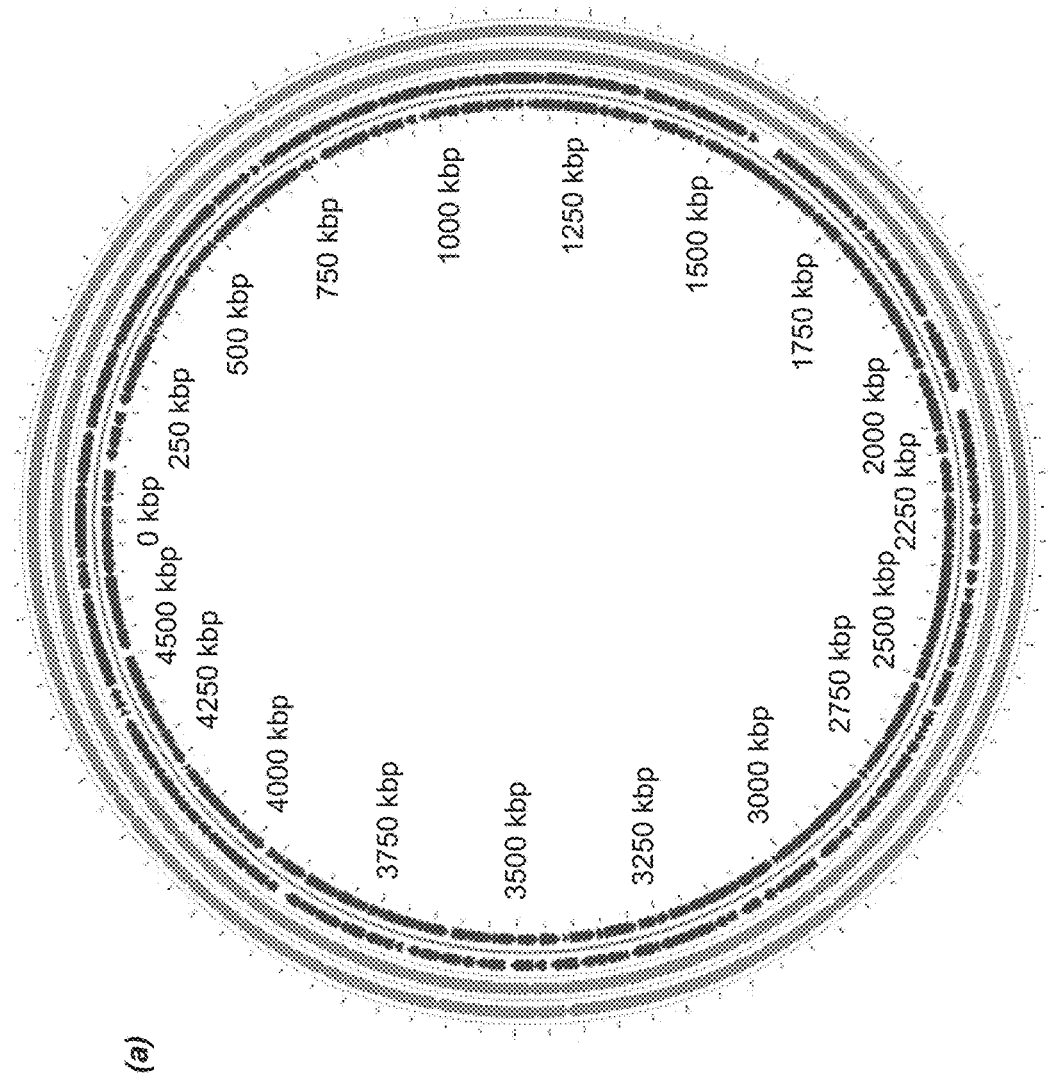
FIG. 12 panels (a)-(d) show an overview of an *E. coli* Dub-seq library.
Figure 12:
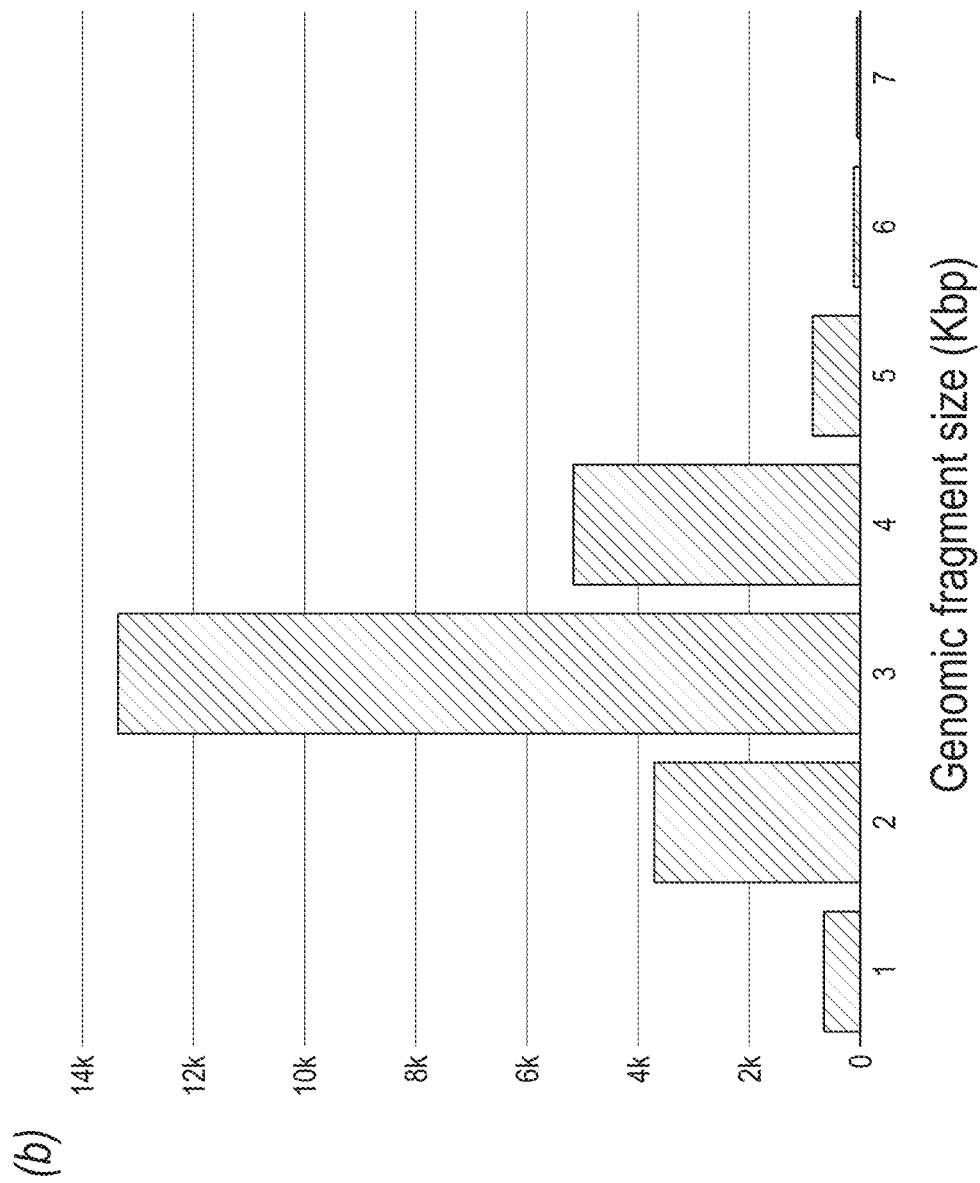
Figure 12:
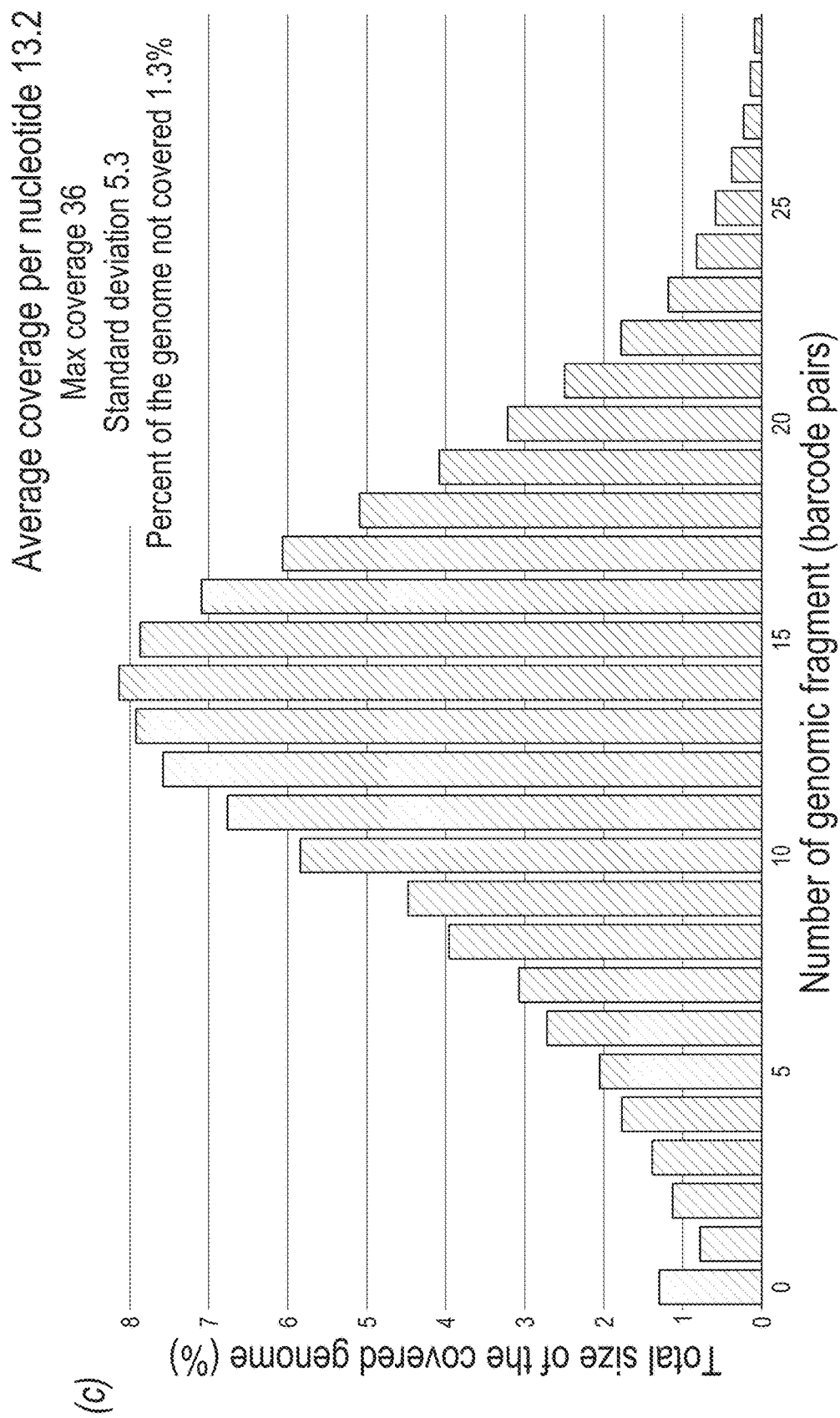
Figure 12:
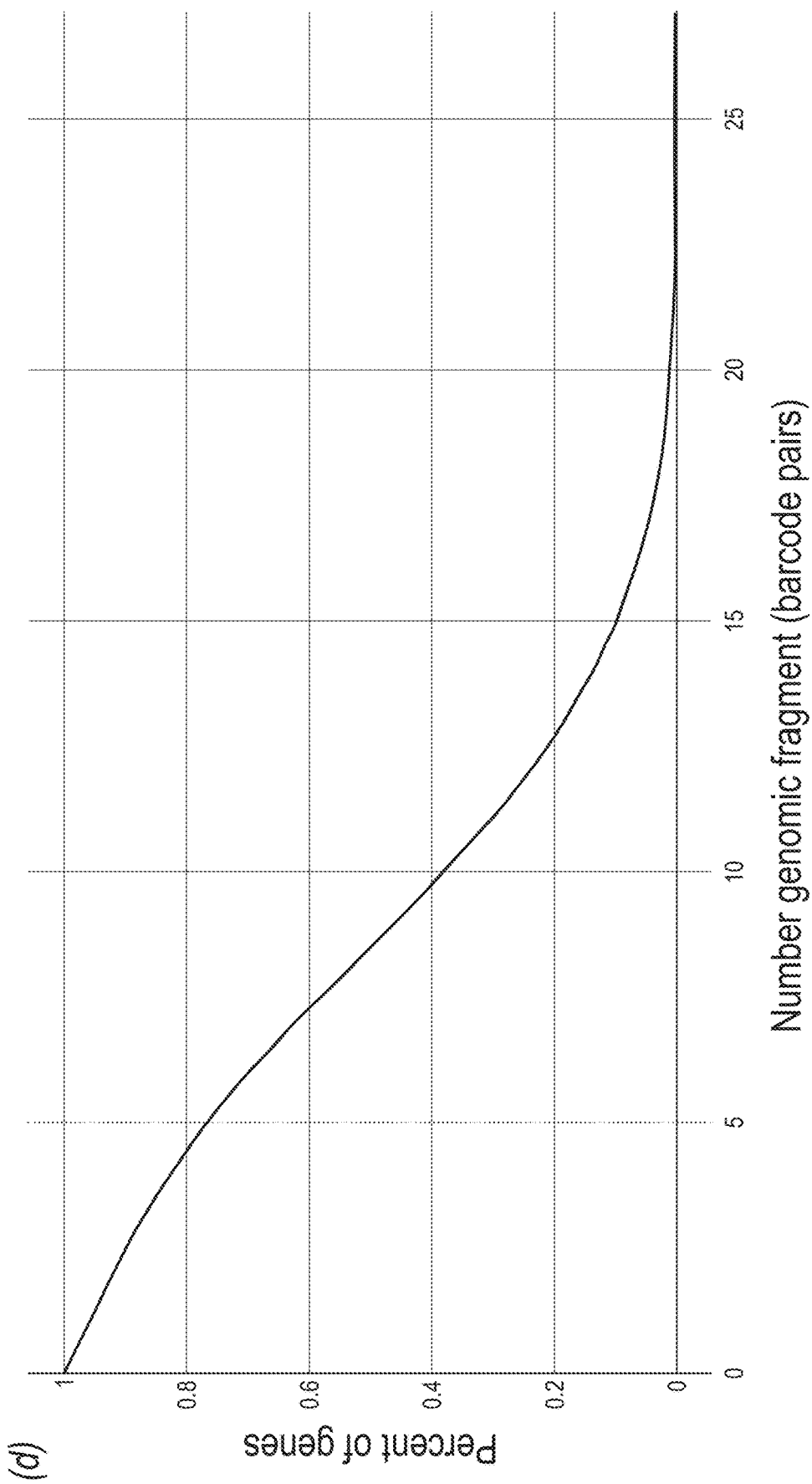

FIG. 12 panels (a)-(d) show an overview of an *E. coli* Dub-seq library. Panel (a) Genomic distribution of ~30K mapped fragments in *E. coli* genome. Two blue circles show the location of genes on positive and negative strands, while two red circles show the location of Dubseq fragments on both strands. Panel (b) Genomic fragment size distribution. Panel (c) Distribution of genome coverage by genomic fragment insertions. Panel (d) Genes covered by more than N number of genomic fragments. There are 181 genes not covered and almost 80% of all genes are covered by greater than or equal genomic fragments.

BAGseq to Characterize Barcoded Genomic Fragment Junctions

The entire plasmid library was characterized using a TnSeq-like protocol (Wetmore et al (2015) Rapid quantification of mutant fitness in diverse bacteria by sequencing randomly barcoded transposons (RB-TnSeq). mBio 6(3): e00306-15); referred to herein as Barcode-association—with genome fragment sequencing or BAGseq; the content of which is incorporated herein by reference in its entirety). BAGseq helped identify the cloned genome fragment and its pairings with neighboring dual barcodes. This step of associating the dual barcodes with each library of genomic fragments was only done once (by deep sequencing) and used as a reference table to derive connections between observed functional/fitness traits with specific cloned genomic fragment (FIG. 4).

To generate Illumina compatible sequencing libraries to link both random DNA bar codes to the terminal of cloned genome fragment, two samples per library were processed. The plasmid library (1 ug) samples were fragmented by ultrasonication to an average size of 300 bp with a Covaris S220 focused ultrasonicator. To remove DNA fragments of unwanted size, a double size selection was performed using AMPure XP beads (Beckman Coulter) according to the manufacturer's instructions. The final fragmented and size-selected plasmid DNAs were quality assessed with a DNA1000 chip on an Agilent Bioanalyzer. Illumina library preparation involved a cascade of enzymatic reactions, each followed by a cleanup step with AMPure XP beads. Fragmentation generated plasmid DNA library with a mixture of blunt ends and 5' and 3' overhangs. End repair, A-tailing, and adapter ligation reactions were performed on the fragmented DNA using the NEBNext DNA Library preparation kit for Illumina (New England Biolabs), according to the manufacturer's recommended protocols. For the adapter ligation, 0.5 ul of a 15 uM double-stranded Y adapter was used, which was prepared by annealing Mod2_TS Univ (5' ACGCTCTTCCGATC*T 3'; Seq ID No. 50) and Mod2_TruSeq (5' Phos-GATCGGAAGAGCACACGTCT-GAACTCCAGTCA 3'; Seq ID No. 51). In the preceding oligonucleotides, the asterisk and Phos denote phosphorothioate and 5' phosphate modifications, respectively.

To specifically amplify the up tag (also referred to herein as the up Barcode) and neighboring genomic fragment terminus by PCR, the up-tag-specific primer oFAB2923_Nspacer_barseq_universal (5' ATGA-TACGGCGACCACCGAGATCTACACTCTTTCCCTA-CACGACGCTCTTCCGATC GATGTCCACGAGGTCT 3'; Seq ID No. 22) Italics region binds to Flow Cell P5, entire underlined is a TruSeq Universal Adapter) which contains a random hexamer and Up-tag-specific sequence on the 3' end and an Illumina TruSeq sequence on the 5' end, and P7_MOD_TS_index1 primer containing the Illumina P7 end. For the down tag amplification oFAB2924 Nspacer_barseq_universal 5' ATGATACGGCGAC-CACCGAGATCTACACTCTTTCCCTA-CACGACGCTCTTCCGATC cggtgtcggtctcgta 3' (Seq ID No. 43) and P7_MOD_TS_index2 primer containing the Illumina P7 end were used. For the BAGseq up tag and down tag site enriching PCR, JumpStart Taq DNA polymerase (Sigma) was used in a 100 ul total volume with the following PCR program: 94° C. for 2 min and 25 cycles of 94° C. 30 s, 65° C. for 20 s, and 72° C. for 30 s, followed by a final extension at 72° C. for 10 min.

The final PCR product was purified using AMPure XP beads according to the manufacturer's instructions, eluted in 25 ul of water, and quantified on an Agilent Bioanalyzer with a DNA1000 chip. Each BAGseq library was then sequenced on the HiSeq 2500 system (Illumina) 150 SE run to map up and down tag barcodes to genomic inserts in the Dub-seq *E. coli* library.

BAGseq Data Analysis

Each BAGseq was processed independently, and a pair of a barcode and an associated genomic fragment were extracted from each read based on the location of the predefined primers (or Dub-seq primers). The only barcodes that had sequence quality greater than 20 for each nucleotide were accepted for further analysis. The extracted genomic fragments were mapped to the target genome using the BLAT tool with the default parameters. As a result of this step, a particular barcode can be associated with multiple locations in a target genome. The barcode-to-genomic-location associations were reconstructed for both up and down barcodes resulting in two sets for up and down barcodes: $UG_i=\{u_i, [\{x_{ik}, nx_{ik}\}]\}$ and $DG_j=\{d_j, [y_{jm}, ny_{jm}]\}$, where $u_i$—up barcode, $x_{ik}$—location of a genomic fragment associated with up barcode $u_1$ in a target genome, $nx_{ik}$—number of reads in BAGSeq data supporting a given location $x_{ik}$, $d_j$—down barcode, $y_{jm}$—location of a genomic fragment associated with down barcode $d_j$ in a target genome, $ny_{jm}$—number of reads in BAGSeq data supporting a given location $y_m$.

Overcoming Challenges of BPseq and BAGseq Data Processing

There were several obstacles in the BPSeq and BAGSeq data that can potentially lead to false positive predictions in the association between up and down barcodes (from BPSeq), association between a barcode and a genomic fragment (from BAGSeq), and ultimately between a barcode pair and a genomic region in a target genome. These potential errors can be caused by multiple reasons, including the sequencing errors in barcodes, chimeras as a result of the PCR procedure, not unique mapping of a genomic fragment by BLAT (e.g. if a genomic fragment is a part of ribosomal RNA present in multiple copies in a genome). In order to overcome these limitations, the ultimate decision on all three types of associations—association between up and down barcodes, association between a barcode and a genomic fragment, and association between a barcode pair and a genomic region—were done by post processing of three sets $P_{ij}$, $UG_i$, and $DG_i$ generated in a course of the initial analysis of the BPSeq and BAGSeq data. Specifically, for each pair of up and down barcodes $u_i$ and $d_j$ in $P_{ij}$, all pairs of the corresponding putative locations of the genomic fragments $x_{ik}$ and $y_{jm}$ (defined by $UG_i$ and $DG_j$) were considered. The pair of coordinates $x_{ik*}$ and $y_{jm*}$ (start and end of the putative genomic region) that resulted in the minimum distance was considered as coordinates of the candidate genomic region. Finally, the barcode pair defined by $\{u_i, d_j\}$ was considered to be associated with a genomic region defined by $\{x_{ik*}, y_{jm*}\}$ if:

i) Distance between $x_{ik*}$ and $y_{jm*}$ was less than 6000 bp, which was the maximum expected length on the inserted genomic fragment.

ii) Both $x_{ik*}$ and $y_{jm*}$ were well supported by BAGSeq reads: $nx_{ik*}/\text{summa\_by\_k}(nx_{ik}) >= 0.5$ and $ny_{jm*}/\text{summa\_by\_m}(ny_{jm*}) >= 0.5$.

iii) The association between up and down barcodes $u_i$ and $d_j$ were well supported by BPSeq reads: $n_{ij} > 10$.

As a result of the BPSeq and BAGSeq procedure, the set of well supported associations between up and down barcodes and a genomic region was generated: $S=\{u_i, d_j, r_{ij}\}$, where $u_i$—up barcode, $d_j$—down barcode, $r_{ij}$—genomic region associated with a pair of up and down barcodes $u_i$ and $d_j$.

Competitive Growth Experiments

Using the deep sequenced *E. coli* Dub-seq library, pooled fitness assays were performed on six conditions to establish the characterization pipeline. These 6 stress conditions included different concentrations of Nickel, Copper, Cobalt, Benzalkonium chloride, Polymyxin B, Spectinomycin. A single aliquot of a Dub-seq library was thawed, inoculated into 25 ml of medium supplemented with Chloramphenicol and grown to mid-log phase. After the Dub-seq library recovered and reached mid-log phase, cell pellets were collected as a common reference for BarSeq (termed time-zero samples) and used the remaining cells to set up competitive mutant fitness assays under different experimental conditions at a starting OD600 of 0.02. These experiments were performed in the wells of a 48-well microplate (700 ul per well). The cells in the microplates were grown in Tecan Infinite F200 readers with orbital shaking and $OD_{600}$ readings every 15 min. In general, all of the mutant library assays reached saturated growth, and collected $\sim 2\times 10^9$ cells ($\sim 1$ ml of a 1.0-OD600 culture) for plasmid DNA extraction. For the microplate experiments, the contents of two replicate wells (1.4-ml total volume) were combined prior to collecting the pellet. Mutant library cell pellets were typically stored at $-80°$ C. prior to plasmid DNA extraction.

Barseq

Plasmid DNA from Dub-seq library samples was extracted either using the Plasmid miniprep kit (Qiagen) or in an automated, 96-well format with a QIAprep 96 Turbo miniprep kit (Qiagen). Plasmid DNA was quantified with the Quant-iT dsDNA BR assay kit (Invitrogen). Barseq PCR was performed in a 50 ul total volume with 20 umol of each primer and 150 ng of template plasmid DNA. In the Barseq PCR step, only the up tag was amplified with forward primer Barseq_p2_ITXXX (CAAGCAGAAGACGGCAT-ACGAGATCGTGATGTGACTGGAGTTCA-GACGTGTGCTC TTCCGATCTGATGTC-CACGAGGTCTCT; Seq ID No. 4; bold region binds to the primer binding region of UP-tag, while Italics region binds to Flow Cell P7; Barseq Forward primer with index 1 to 96, has unique 6-bp TruSeq indexes) and an universal reverse primer for Barseq, BSP-RV
Seq ID No. 45
(AATGATACGGCGACCACCGAGATCTACACTCTTTCCCTACACGACGCTC

TTCCGATCTNNNNNNGTCGACCTGCAGCGTACG;;

bold region binds to UP-tag, while Italics region binds to Flow Cell P5 and entire underlined is a TruSeq Universal Adapter).

BarSeq PCR recipe:
5 ul FW Barseq_P2_ITXXX (4 uM)
0.2 ul of BSP RV (100 uM)
150 ng of template
10 ul of 5× Q5 buffer
10 ul of 5× Q5 GC enhancer
1 ul of 10 mM dNTPs
0.5 ul of Q5 polymerase
Water to make total volume 50 ul Barseq PCR was done under following cycling conditions: 98° C. for 4 min followed by 25 cycles of 30 s at 98° C., 30 s at 55° C., and 30 s at 72° C., followed by a final extension at 72° C. for 5 min. PCR amplification was confirmed by running samples on an analytical gel. Finally, equal volumes (10 ul) of the individual BarSeq PCRs were pooled, and 200 ul of the pooled PCR product was purified with the DNA Clean and Concentrator kit (Zymo Research). The final BarSeq library was eluted in 30 ul water and quantified using the Qubit dsDNA HS assay kit. The BarSeq libraries were sequenced on Illumina HiSeq 2500 instrument. We usually multiplex 48 to 96 samples per lane for sequencing.

Barseq Data Analysis and Fragment Score Calculation

Each BarSeq assay was analyzed separately, processed independently, and a barcode was extracted from each read based on the location of the predefined primers. The only barcodes that had sequence quality greater than 20 for each nucleotide are accepted for further analysis. A non-redundant set of unique barcodes was reconstructed: T={$b_i$, $n_i$}, where $b_i$ denotes the up barcode, and $n_i$ is a number of read supporting the barcode $b_i$.

Defining the Fitness Value

Fitness value for a Dub-seq region was defined as:

$$f = \log_2 \frac{N_s}{N_t},$$

where $N_s$ is a number of BarSeq reads supporting a barcode associated with a given Dub-seq region (insertion) in a stress (treatment), and $N_t$ is a number of the BarSeq reads for the same barcode in time-zero datasets.

Dub-Seq Score for a Genomic Region

The arbitrary genomic region R can overlap with a number of Dub-seq regions (insertions). To calculate the Dub-seq score of a genomic region R, all Dub-seq regions (insertions) overlapping with region R were collected, and then split into two categories: the PLUS Dub-seq regions that contained genomic region R completely, and the MINUS Dub-seq regions that overlapped with region R and contained it only partially. Fitness values were estimated separately for the PLUS and MINUS sets, and the difference between fitness values of the PLUS and MINUS sets defined the score of the genomic region R.

$$S_r = S_r^+ - S_r^-,$$

where $S_r$ is a Dub-seq score of the region R, $S_r^+$ and $S_r^-$ are the average fitness of the PLUS and MINUS sets. The rationale behind the separation of all Dub-seq regions (insertions) into two sets was that if it was expected that a particular genomic region R (e.g. a gene) is important for fitness as a whole, then only those Dub-seq regions covering R completely should have high fitness. At the same time, if a Dub-seq region covered R only partially, then it had only a truncated version of R that might be non-functional, and thus should not demonstrate a high fitness value.

$$S_r^+ = \frac{1}{N_r^+} \sum_{i=0}^{N_r^+} f_{ri}^+,$$

where $N_r^+$—the number of Dub-seq regions from the PLUS set, $f_{ri}^+$—fitness value of Dub-seq region i from the PLUS set covering region R completely.

$$S_r^- = \frac{1}{N_r^-} \sum_{i=0}^{N_r^-} f_{ri}^- I(f_{ri}^- > 0),$$

where $N_r^-$—number of Dub-seq regions from the MINUS set, $f_{ri}^-$—fitness value of Dub-seq region i from the MINUS set covering region R partially.

$$I(x) = \begin{cases} 1, & x > 0 \\ 0, & x \leq 0 \end{cases}$$

Figure 13:
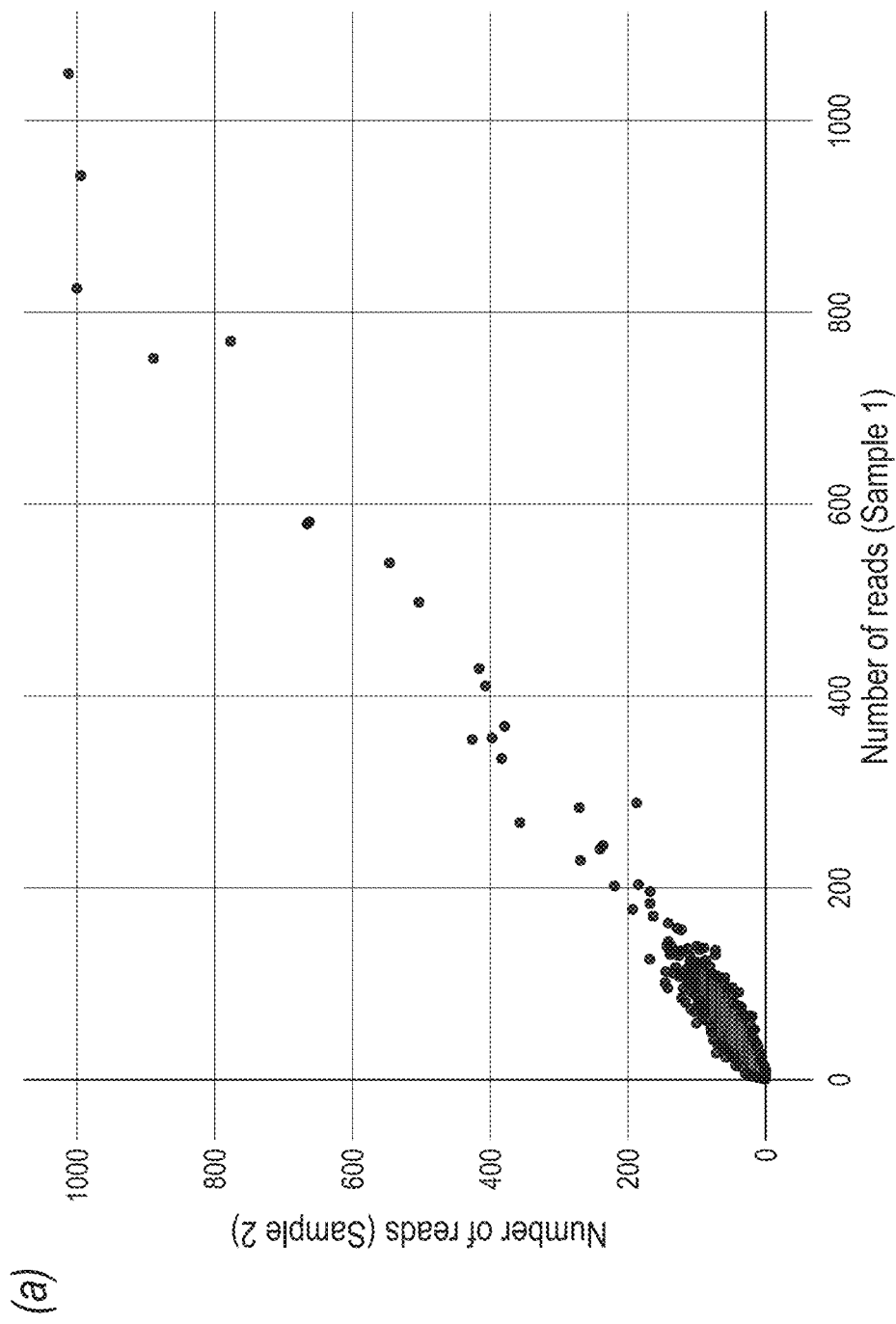
FIG. 13 panels (a)-(g) show test fitness assays using *E. coli* Dubseq library.
Figure 13:
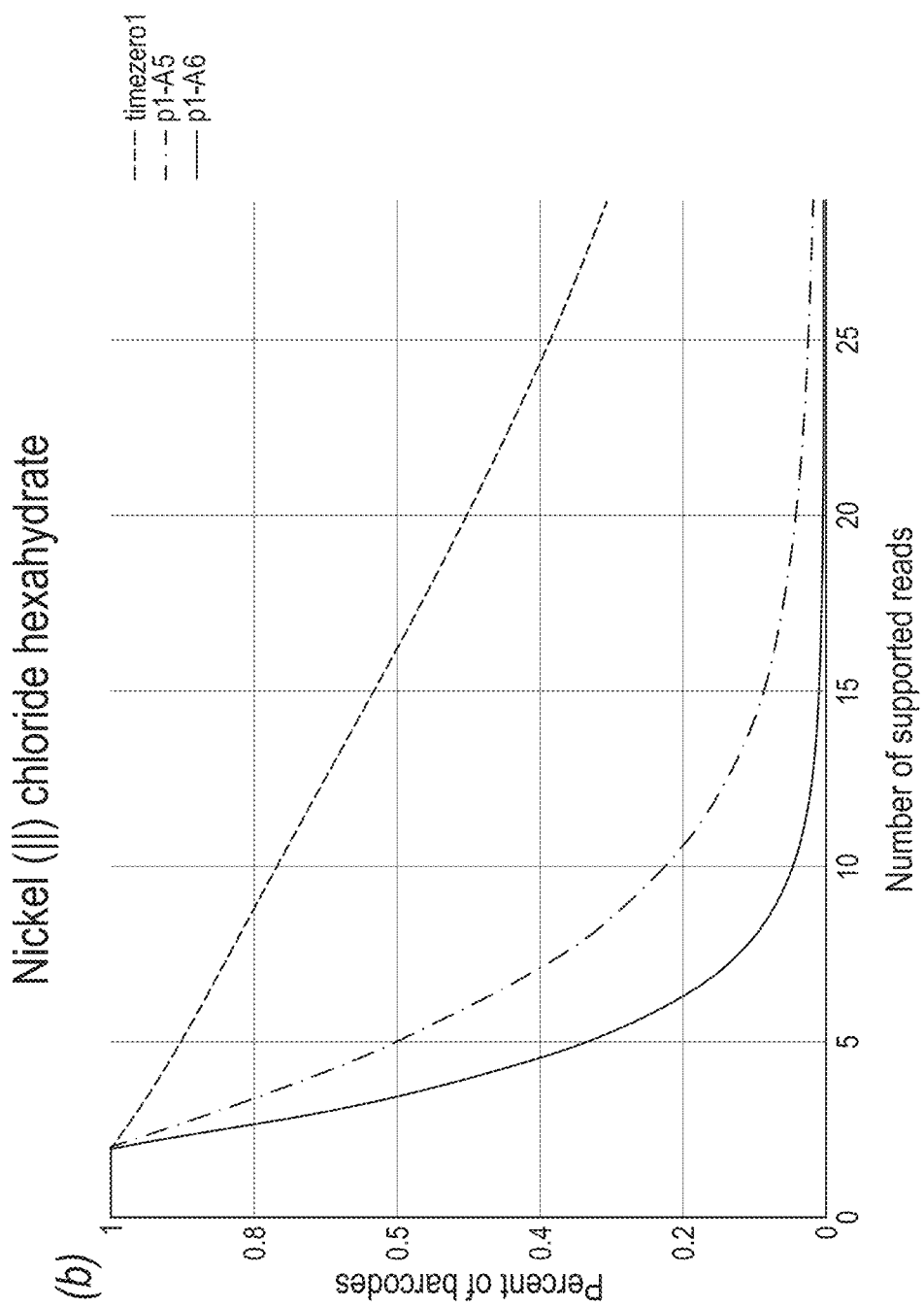
Figure 13:
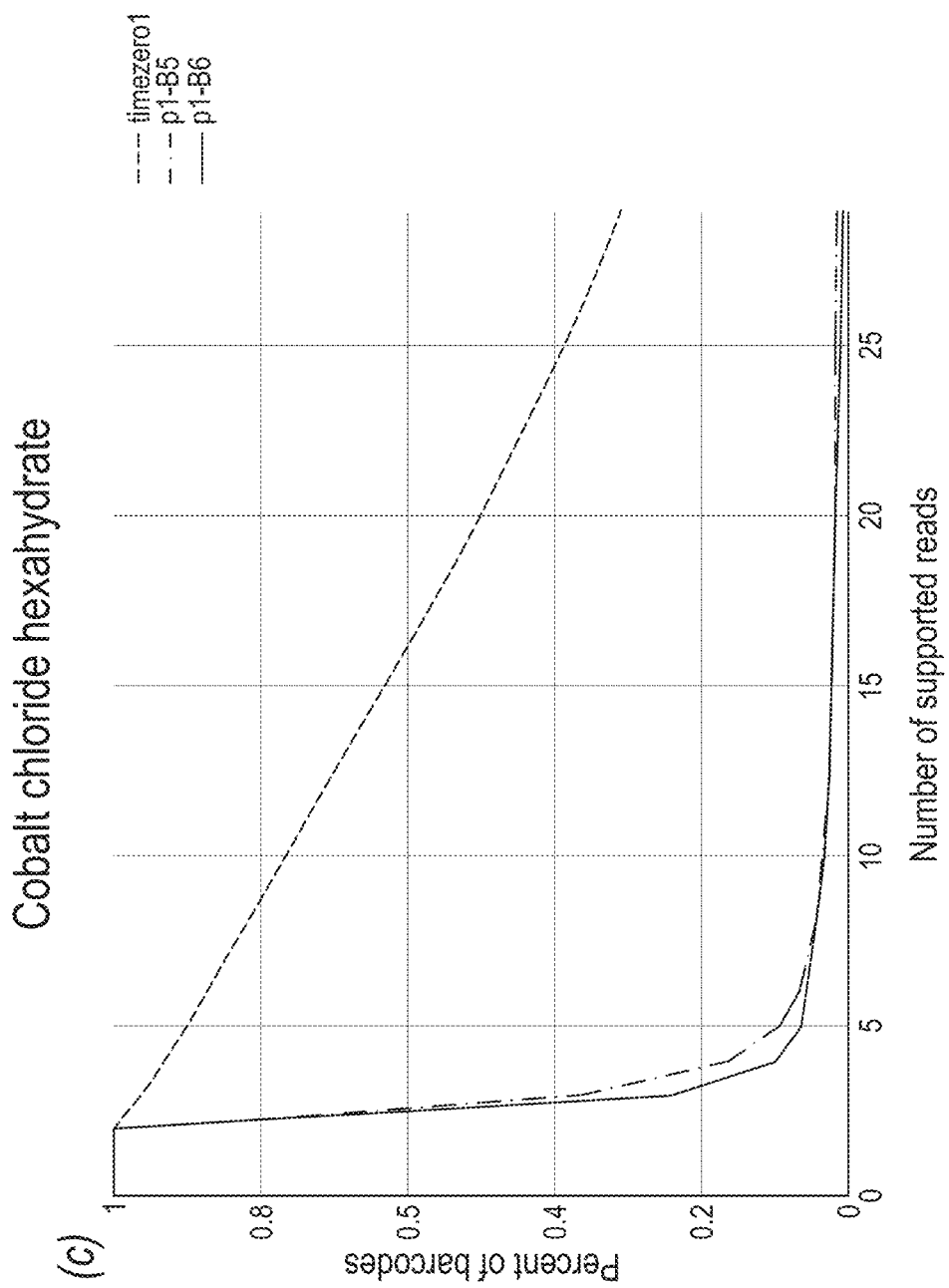
Figure 13:
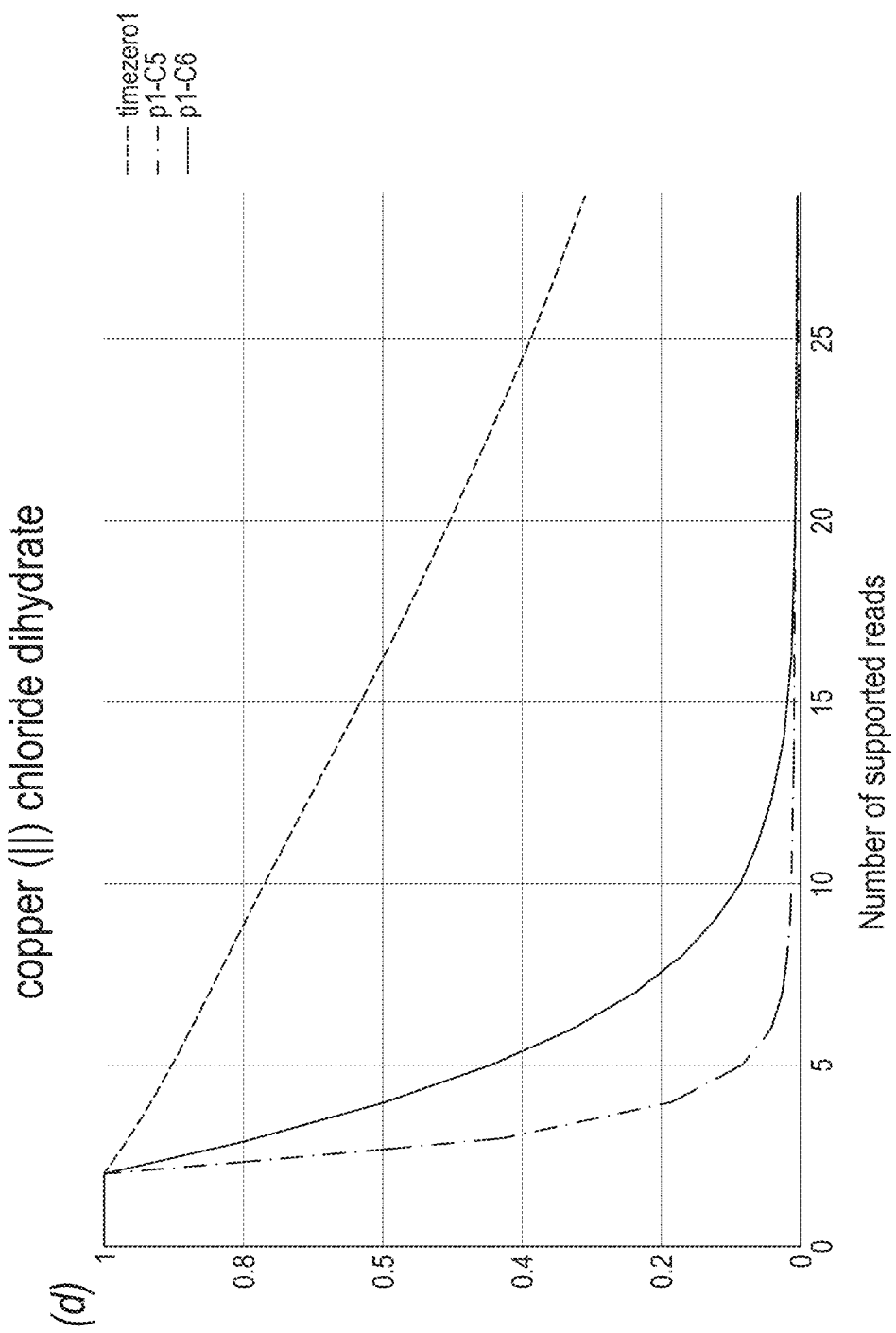
Figure 13:
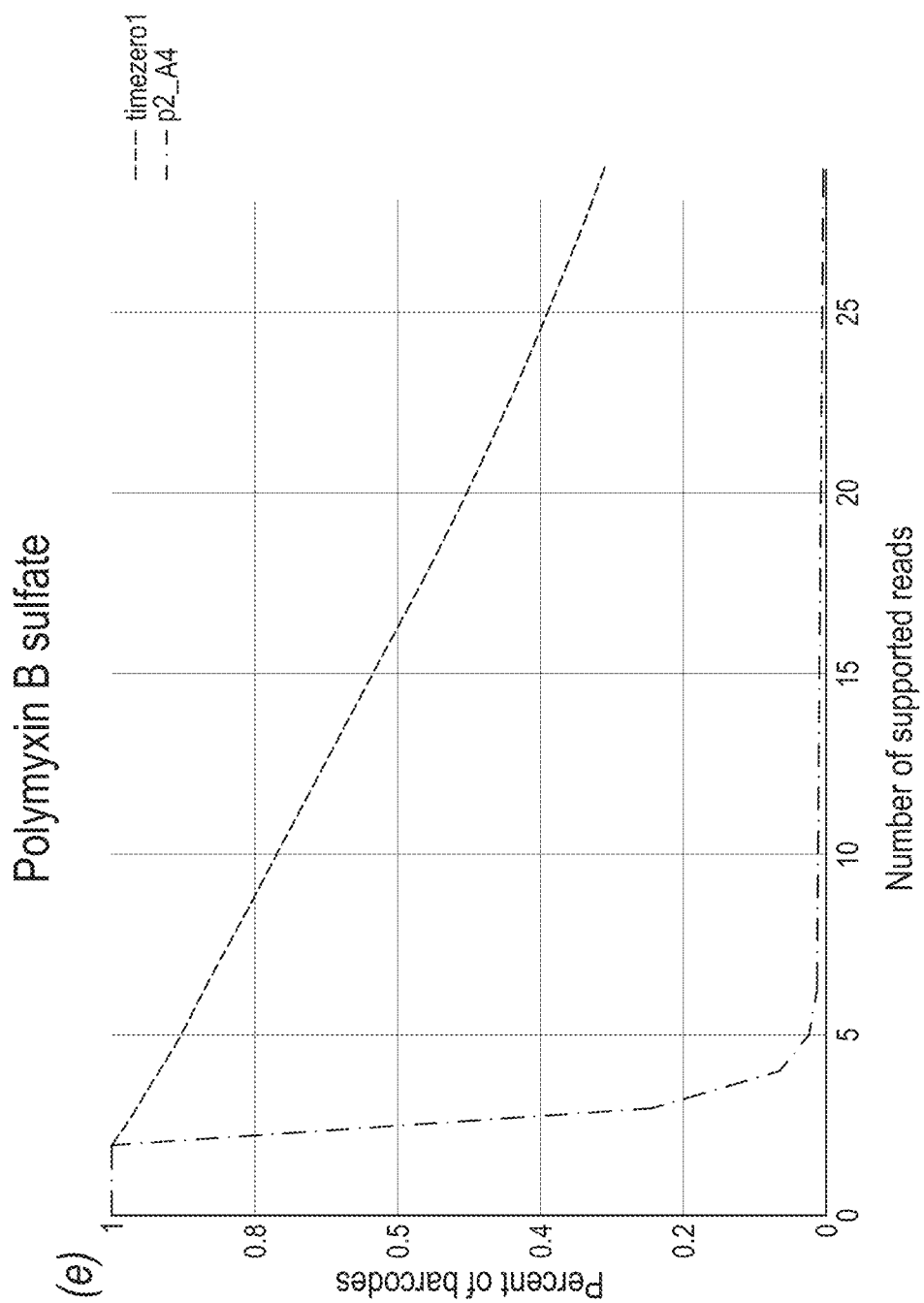
Figure 13:
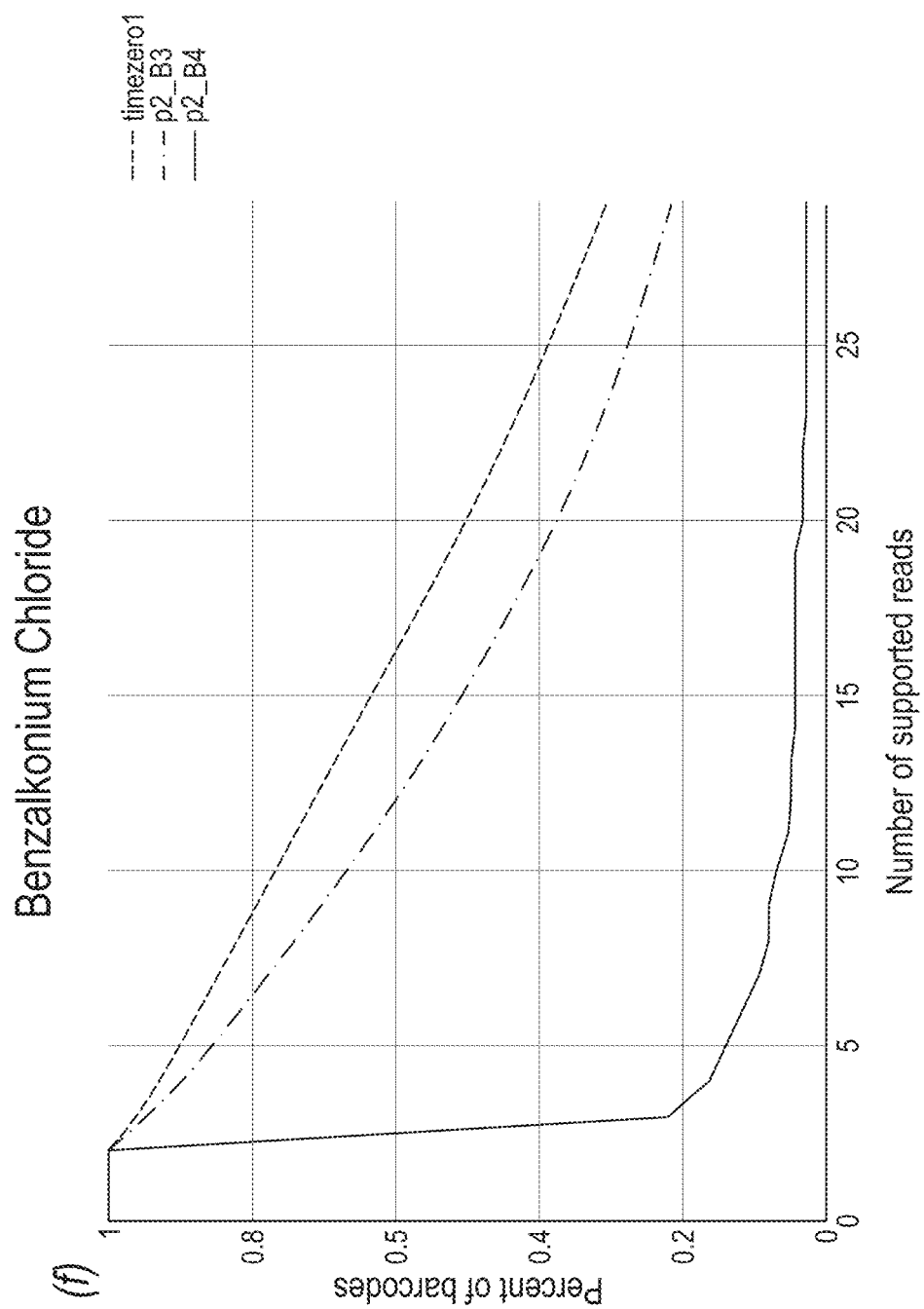
Figure 13:
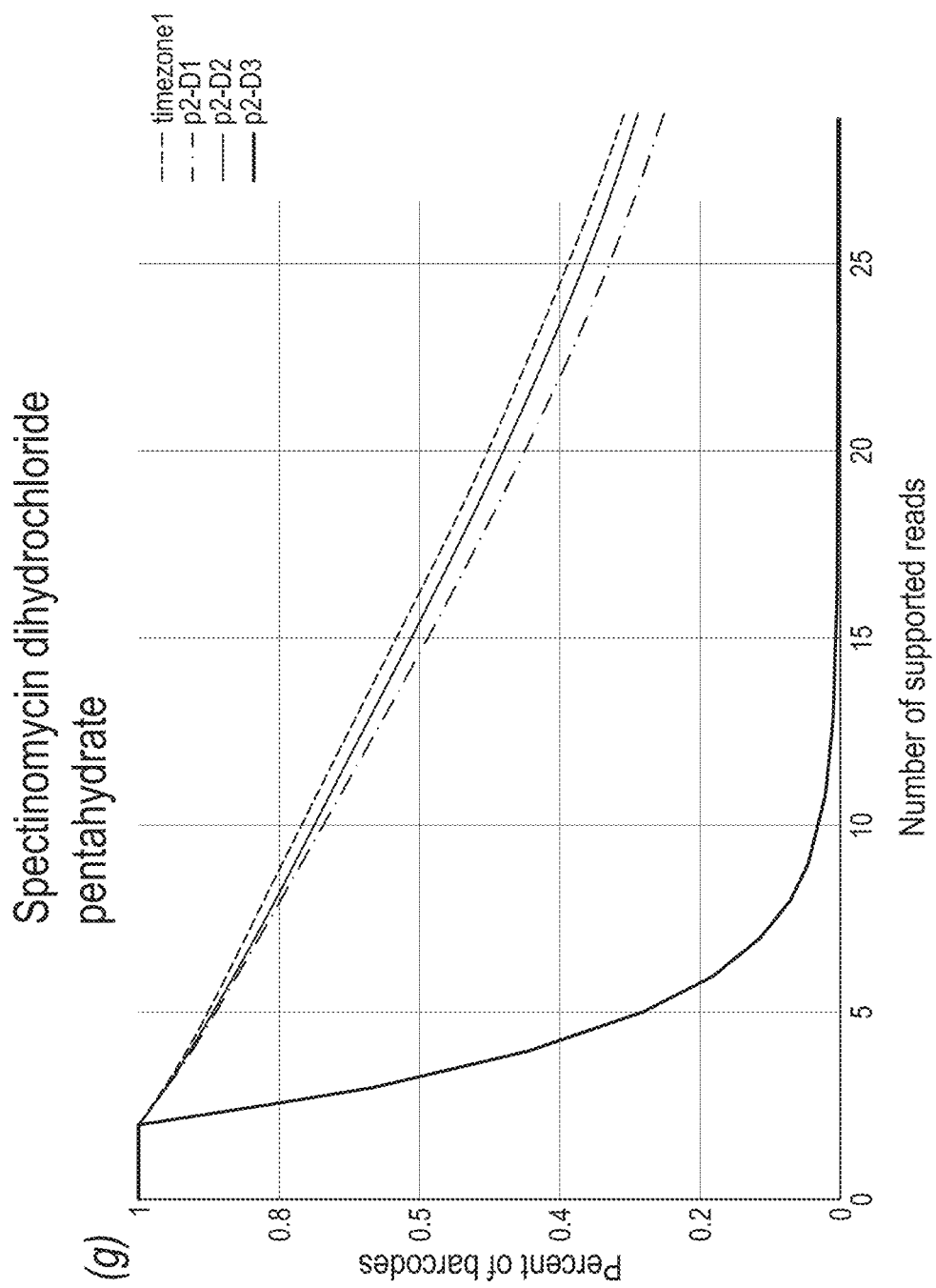

FIG. 13 panels (a)-(g) show test fitness assays using *E. coli* Dubseq library. Panel (a) Replicate experiment with no stress condition; Number of reads supporting barcode estimations for two biological replicates with Pearson correlation coefficient of 0.93. Panels (b)-(g) Quantifying Barseq data by plotting percentage of barcodes vs. number of reads in each experiment in 6 different stress conditions. Blue curve shows barcode and read count under no stress condition. Orange and Green curves show barcode and read counts for high and very high concentration of stresser respectively. As can be seen from the plots, as the stress condition is applied, most barcodes disappear (as corresponding cells die), but few survive due to tolerance to stress condition because of expression of a genomic fragment.

FIG. 14 panels (a)-(f) are non-limiting exemplary plots showing snapshot of fitness data of *E. coli* Dubseq library. A chosen few genes with highest fitness scores for each of 6 stress conditions are shown. Insets give general mechanism of stress tolerance or pathway involved. Genes involved in genomic fragments are shown.

Figure 15:
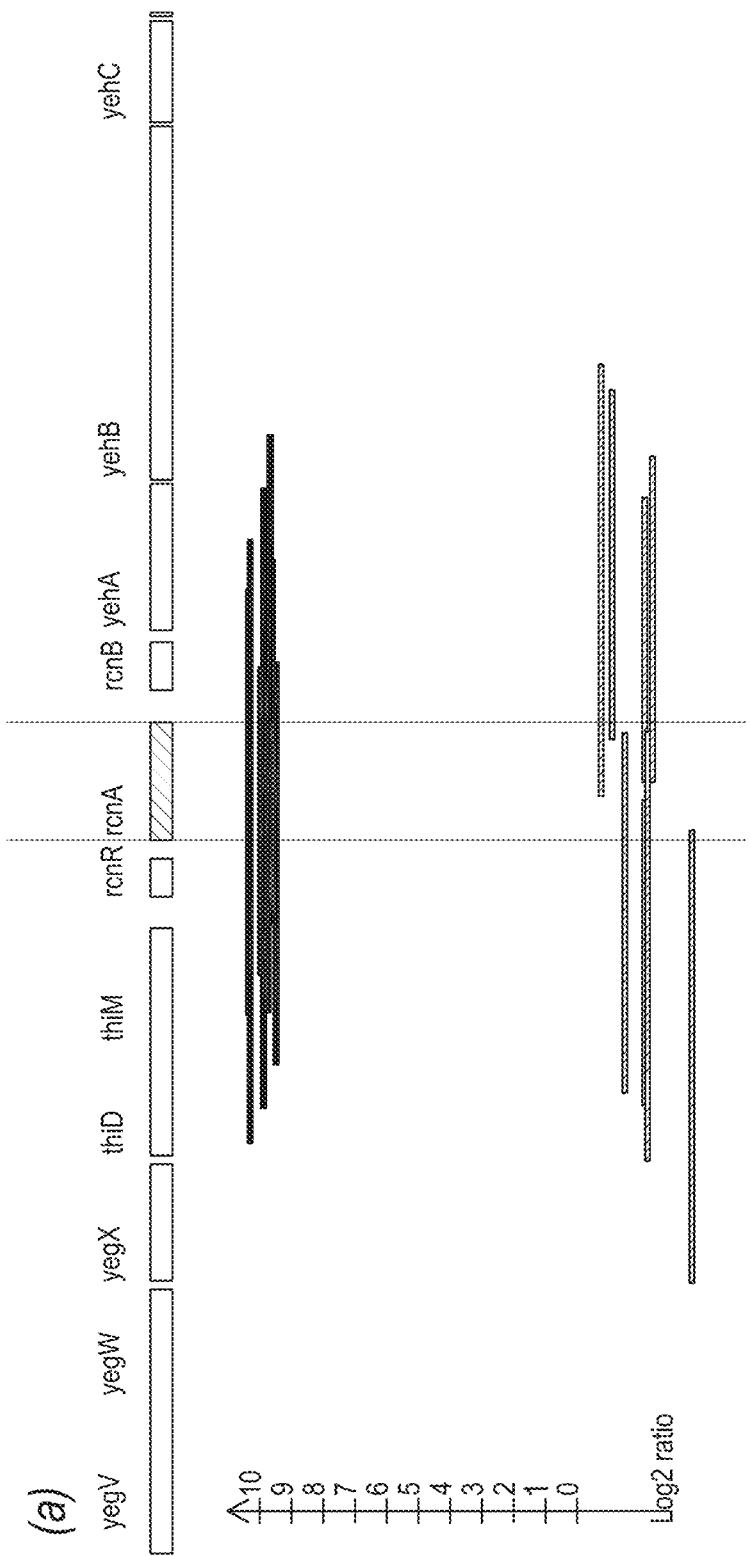
FIG. 15 panels (a)-(c) are non-limiting exemplary plots showing visualization for quantitative fitness data for *E. coli* Dubseq library and locus of genomic fragment yielding stronger phenotype.
Figure 15:
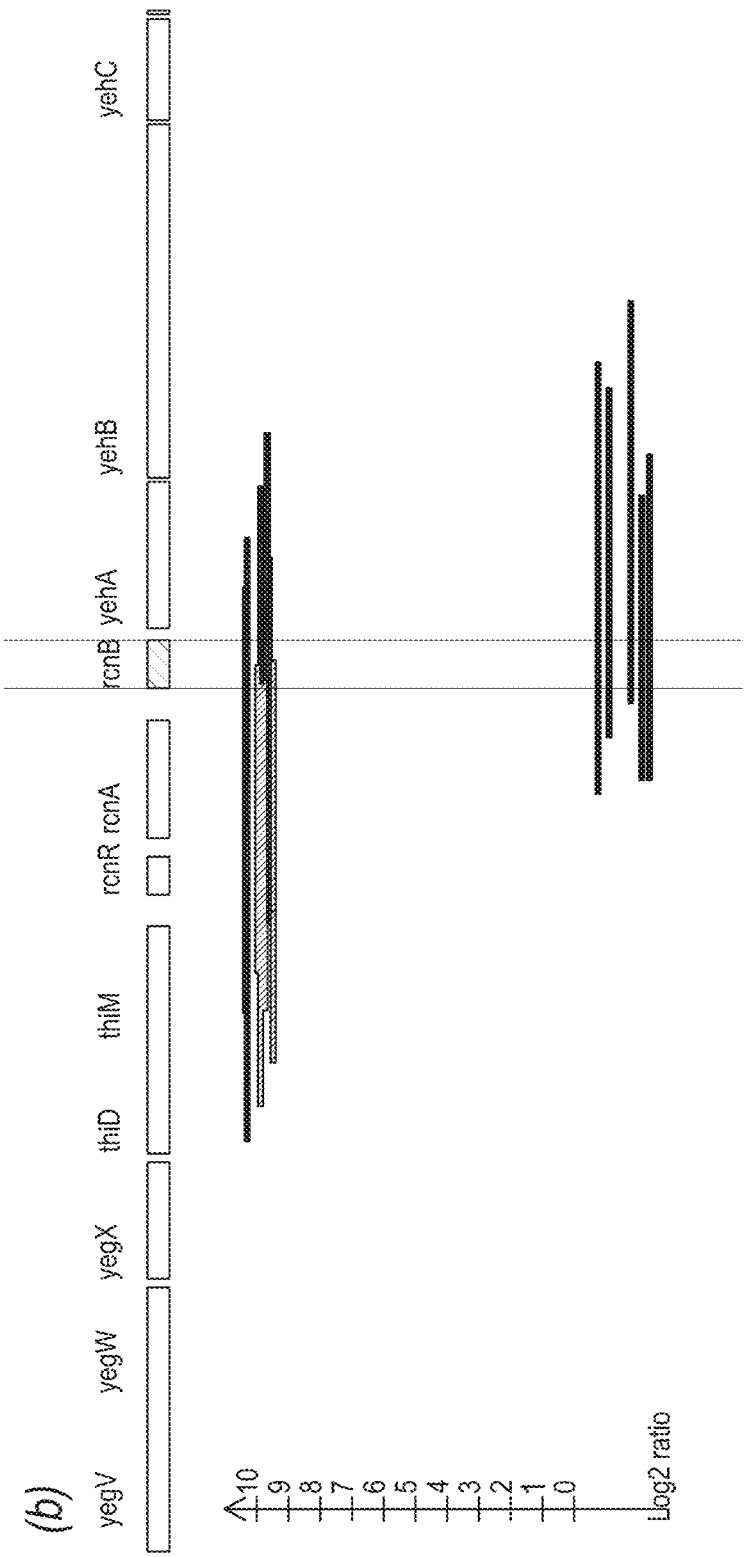
Figure 15:
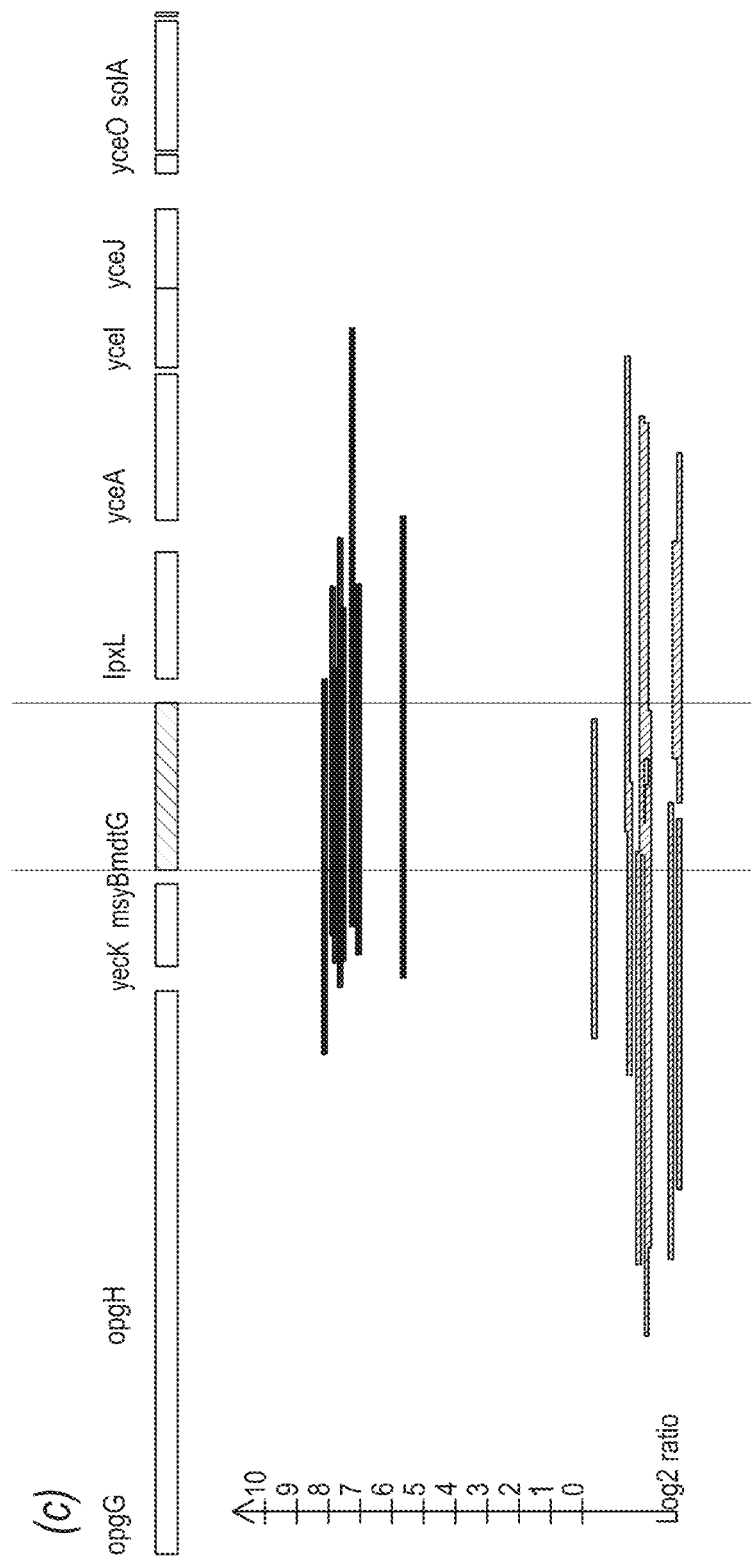

In addition to the data analytics pipeline, an easy to understand visualization tool was developed for displaying quantitative contribution of genomic fragment in particular stress condition. FIG. 15 panels (a)-(c) are non-limiting exemplary plots showing visualization for quantitative fitness data for *E. coli* Dubseq library and locus of genomic fragment yielding stronger phenotype. Panel (a) Fitness profile (Nickel stress): rcnA—gene with highest score (green) as an example of the true positive prediction. Panel (b) Fitness profile (Nickel stress): rcnB—false positive as it has Dubseq regions with high score that covers it only partially, as well as DubSeq regions with low fitness value that cover it completely. Panel (c) Fitness profile (Nickel stress): mdtG—the second strongest gene.

Figure 16:
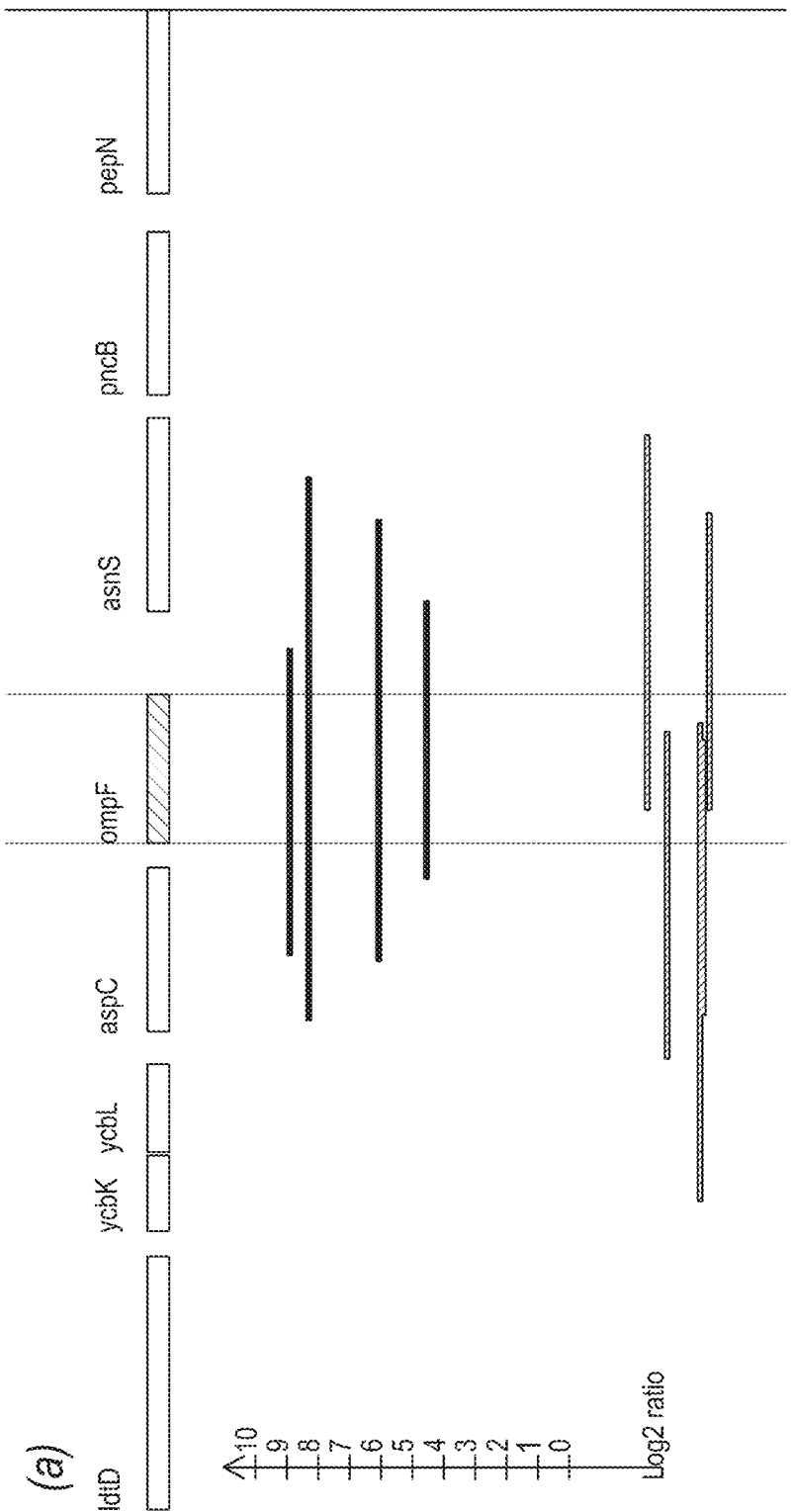
FIG. 16 panels (a)-(b) are non-limiting exemplary plots showing visualization for quantitative fitness data for *E. coli* Dubseq library and locus of genomic fragment yielding stronger phenotype.
Figure 16:
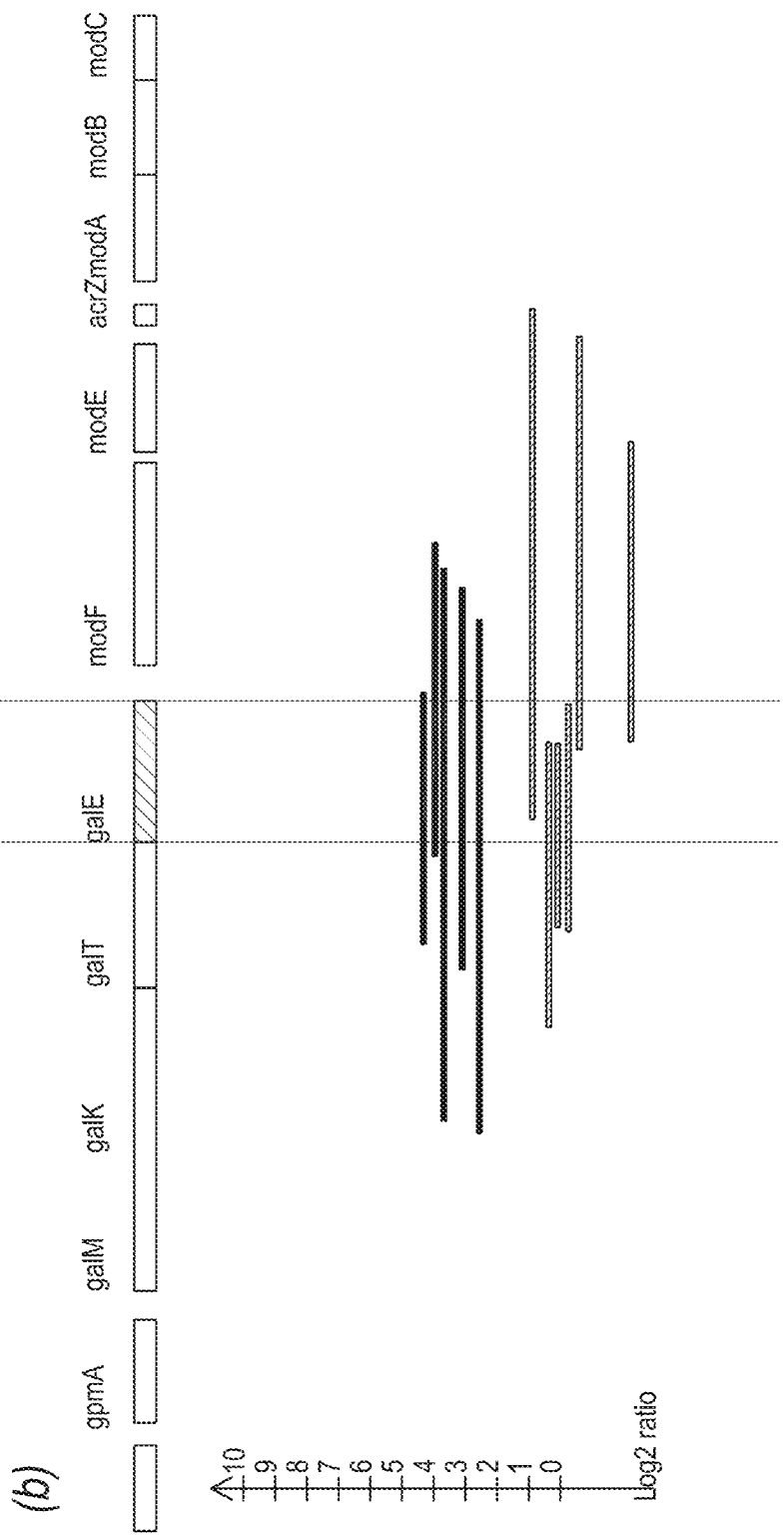

FIG. 16 panels (a)-(b) are non-limiting exemplary plots showing visualization for quantitative fitness data for *E. coli* Dubseq library and locus of genomic fragment yielding stronger phenotype. Panel (a) Fitness profile (Copper stress): ompF—gene with highest score (green) as an example of the true positive prediction. Panel (b) Fitness profile (Benzalkonium stress): galE shows stronger fitness phenotype.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method, comprising:
   providing a plurality of genomic nucleic acid fragments;
   providing a plurality of vectors each comprising a first barcode and a second barcode;
   inserting the plurality of genomic nucleic acid fragments into the plurality of vectors to generate a plurality of expression vectors, wherein each of the plurality of expression vectors comprises a genomic nucleic acid fragment from the plurality of genomic nucleic acid fragments flanked by the first barcode and the second barcode; and
   sequencing, for each of the plurality of expression vectors, the first barcode using a first primer set and the second barcode using a second primer set by amplifying the first barcode and a portion of the genomic nucleic acid fragment adjacent to the first barcode using the first primer set and amplifying the second barcode and a portion of the genomic nucleic acid fragment adjacent to the second barcode using the second primer set, thereby obtaining a sequence of the genomic nucleic acid fragment, a sequence of the first barcode and a sequence of the second barcode in the expression vector,
   linking the sequence of the first barcode and the sequence of the second barcode with the sequence of the genomic nucleic acid fragment, transforming the plurality of expression vectors into a host organism, subjecting the transformed organism to a stress condition, collecting the plurality of expression vectors from the transformed host organism subjected to the stress condition, and identifying a genomic nucleic acid fragment or a product thereof that yields tolerance to the stress condition by performing a quantitative analysis of the first barcode and the second barcode from the collected plurality of expression vectors prior to and after subjecting the transformed organism to the stress condition.

2. The method of claim 1, wherein the host organism is selected from bacteria, yeast, fungi, insect cells, mammalian cells, and plant cells.

3. The method of claim 1, wherein the plurality of genomic nucleic acid fragments is from a single cell, a plurality of cells, a tissue sample, a virus, a fungus, or any combination thereof.

4. The method of claim 1, wherein the plurality of genomic nucleic acid fragments comprises a sequenced genome, a single cell genome, a viral genome, a bacterial genome, a metagenome, or any combination thereof.

5. The method of claim 1, wherein the plurality of genomic nucleic acid fragments has an average size of 100 bp to 300 kb.

6. The method of claim 1, wherein the first barcode and the second barcode are randomly generated or selected from a set of diverse barcodes.

7. The method of claim 6, wherein the set of diverse barcodes comprises at least 100, 1000, or 10000 unique barcodes.

8. The method of claim 1, wherein each of the plurality of vectors comprises a promoter exogenous to the plurality of genomic nucleic acid fragments.

9. The method of claim 8, wherein the promoter is selected from the group consisting of a constitutive promoter, a synthetic promoter, an inducible promoter, a promoter having a sequence endogenous to a host organism, a promoter having a sequence exogenous to the host organism, and any combination thereof.

10. The method of claim 1, wherein one of the plurality of vectors comprises a plasmid, a viral vector, a cosmid, a fosmid, or an artificial chromosome.

11. The method of claim 1, wherein one of the plurality of vectors comprises IncQ, IncW, IncP, or pBBR1.

12. The method of claim 1, wherein the host organism is *E. coli*, *Pseudomonas* sp., *Cupriavidus* sp., or *Acidovorax* sp.

13. The method of claim 1, wherein a primer of the first primer set comprises a sequence capable of binding to the first barcode and a primer of the second primer set comprises a sequence capable of binding to the second barcode.

14. The method of claim 1, wherein the plurality of genomic nucleic acid fragments comprises at least 1 fold genomic coverage of a donor organism.

* * * * *